United States Patent
Bergeron et al.

(10) Patent No.: US 9,951,128 B2
(45) Date of Patent: Apr. 24, 2018

(54) CANINIZED ANTI-NGF ANTIBODIES AND METHODS THEREOF

(71) Applicant: ZOETIS SERVICES LLC, Parsippany, NJ (US)

(72) Inventors: Lisa Marie Bergeron, East Grand Rapids, MI (US); Graeme Bainbridge, Kalamazoo, MI (US); Steven Dunham, Kalamazoo, MI (US); Minghua Dai, Plymouth, MN (US)

(73) Assignee: Zoetis Services LLC, Parsippany, NJ (US)

(*) Notice: Subject to any disclaimer, the term of this patent is extended or adjusted under 35 U.S.C. 154(b) by 0 days.

(21) Appl. No.: 15/287,082

(22) Filed: Oct. 6, 2016

(65) Prior Publication Data

US 2017/0158756 A1    Jun. 8, 2017

Related U.S. Application Data

(62) Division of application No. 14/405,959, filed as application No. PCT/US2013/044430 on Jun. 6, 2013, now Pat. No. 9,617,334.

(60) Provisional application No. 61/656,056, filed on Jun. 6, 2012.

(51) Int. Cl.
*A61K 39/395* (2006.01)
*C07K 16/22* (2006.01)
*A61K 39/00* (2006.01)

(52) U.S. Cl.
CPC .......... *C07K 16/22* (2013.01); *A61K 39/3955* (2013.01); *A61K 2039/505* (2013.01); *C07K 2317/24* (2013.01); *C07K 2317/31* (2013.01); *C07K 2317/35* (2013.01); *C07K 2317/54* (2013.01); *C07K 2317/55* (2013.01); *C07K 2317/56* (2013.01); *C07K 2317/569* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,230,691 A | 10/1980 | Young |
| 4,554,101 A | 11/1985 | Hopp |
| 4,676,980 A | 6/1987 | Segal et al. |
| 4,816,567 A | 3/1989 | Cabilly et al. |
| 4,946,778 A | 8/1990 | Ladner et al. |
| 4,980,286 A | 12/1990 | Morgan et al. |
| 5,128,326 A | 7/1992 | Balasz et al. |
| 5,130,311 A | 7/1992 | Guillaumet et al. |
| 5,147,294 A | 9/1992 | Smith et al. |
| 5,223,409 A | 6/1993 | Ladner et al. |
| 5,225,539 A | 7/1993 | Winter |
| 5,258,498 A | 11/1993 | Huston |
| 5,290,540 A | 3/1994 | Prince et al. |
| 5,342,942 A | 8/1994 | Jaen et al. |
| 5,350,576 A | 9/1994 | Payne et al. |
| 5,403,484 A | 4/1995 | Ladner et al. |
| 5,409,944 A | 4/1995 | Black et al. |
| 5,427,908 A | 6/1995 | Dower et al. |
| 5,436,265 A | 7/1995 | Black et al. |
| 5,500,362 A | 3/1996 | Robinson et al. |
| 5,510,368 A | 4/1996 | Lau et al. |
| 5,516,637 A | 5/1996 | Huang et al. |
| 5,530,101 A | 6/1996 | Queen et al. |
| 5,536,752 A | 7/1996 | Ducharme et al. |
| 5,545,806 A | 8/1996 | Lonberg et al. |
| 5,545,807 A | 8/1996 | Surani et al. |
| 5,550,142 A | 8/1996 | Ducharme et al. |
| 5,552,422 A | 9/1996 | Gauthier et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,639,780 A | 6/1997 | Lau et al. |
| 5,648,260 A | 7/1997 | Winter et al. |
| 5,656,435 A | 8/1997 | Nakahama et al. |
| 5,658,727 A | 8/1997 | Barbas et al. |

(Continued)

FOREIGN PATENT DOCUMENTS

WO    WO 1989/009225 A1    10/1989
WO    WO 1990/02809 A1    3/1990

(Continued)

OTHER PUBLICATIONS

Apfel, S.C. et al., Neurology, 51 : 695-702(1998).
Azzazy et al., Clin. Biochem., 35: 425-445 (2002).
Altschul et al.
Braun, et al., Eur. J Immunol., 28:3240-3251 (1998).
Calissano et al., Cell Death and Differentiation, 17: 1126-1133 (2010).
Chothia et al., J. Mol. Biol., 227:799 (1992).
Devereux et al., Nucl Acid. Res., 12:387 (1984).
Giege, R. and Ducruix, A. Barrett, Crystallization of Nucleic Acids and Proteins, a Practical Approach, 2nd ea., pp. 20 1 -216, Oxford University Press, New York, New York, (1999).
Hoogenboom et al., Immunology Today, 21: 371-378 (2000).
Hoogenboom, TIB Tech., 15: 62-70 (1997).
Jonsson, et al. Ann. Biol. Clin. 51: 19-26 (1993).
Kabat et al., Ann. NY Acad, Sci., 190:382-391 (1971).

(Continued)

*Primary Examiner* — Robert C Hayes
(74) *Attorney, Agent, or Firm* — Kelly M. Sullivan

(57) ABSTRACT

The present disclosure describes novel caninized anti-NGF antibodies, antigen binding proteins and polynucleotides encoding the same. The disclosure further describes use of the novel antibodies, antigen binding proteins and/or nucleotides of the invention for the treatment and/or prevention of NGF related disorders, particularly for the management of canine pain.

3 Claims, 20 Drawing Sheets

(56) References Cited

U.S. PATENT DOCUMENTS

| | | |
|---|---|---|
| 5,679,377 A | 10/1997 | Bernstein et al. |
| 5,693,761 A | 12/1997 | Queen et al. |
| 5,693,762 A | 12/1997 | Queen et al. |
| 5,698,426 A | 12/1997 | Huse |
| 5,712,100 A | 1/1998 | Nakahama et al. |
| 5,714,352 A | 2/1998 | Jakobovits |
| 5,723,323 A | 3/1998 | Kauffman et al. |
| 5,733,743 A | 3/1998 | Johnson et al. |
| 5,750,373 A | 5/1998 | Garrard et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,821,337 A | 10/1998 | Carter et al. |
| 5,824,514 A | 10/1998 | Kauffman et al. |
| 5,843,942 A | 12/1998 | Breault et al. |
| 5,844,092 A | 12/1998 | Presta et al. |
| 5,852,183 A | 12/1998 | Maeda |
| 5,855,913 A | 1/1999 | Hanes |
| 5,866,692 A | 2/1999 | Shitara et al. |
| 5,874,064 A | 2/1999 | Edwards et al. |
| 5,877,016 A | 3/1999 | Presta et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jakobovits et al. |
| 6,017,878 A | 1/2000 | Saragovi et al. |
| 6,019,968 A | 2/2000 | Platz et al. |
| 6,027,927 A | 2/2000 | Presta et al. |
| 6,054,297 A | 4/2000 | Carter et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,153,189 A | 11/2000 | Presta et al. |
| 6,180,370 B1 | 1/2001 | Queen et al. |
| 6,180,377 B1 | 1/2001 | Morgan et al. |
| 6,194,167 B1 | 2/2001 | Browse et al. |
| 6,204,023 B1 | 3/2001 | Robinson et al. |
| 6,265,150 B1 | 7/2001 | Terstappen et al. |
| 6,291,247 B1 | 9/2001 | Riopelle et al. |
| 6,350,861 B1 | 2/2002 | Co et al. |
| 6,399,780 B1 | 6/2002 | Hudkins |
| 6,492,380 B1 | 12/2002 | Ross et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,656,465 B2 | 12/2003 | Clary et al. |
| 6,699,658 B1 | 3/2004 | Wittrup et al. |
| 6,774,107 B1 | 8/2004 | Strittmatter et al. |
| 6,790,639 B2 | 9/2004 | Brown et al. |
| 6,797,492 B2 | 9/2004 | Daugherty et al. |
| 6,919,426 B2 | 7/2005 | Boone et al. |
| 7,022,484 B2 | 4/2006 | High et al. |
| 7,029,872 B2 | 4/2006 | Gerngross |
| 7,117,096 B2 | 10/2006 | Luo et al. |
| 7,220,840 B2 | 5/2007 | Ruben et al. |
| 7,252,822 B2 | 8/2007 | Shelton et al. |
| 7,255,860 B2 | 8/2007 | Shelton et al. |
| 7,261,890 B2 | 8/2007 | Krah, III et al. |
| 7,393,648 B2 | 7/2008 | Rother et al. |
| 7,425,329 B2 | 9/2008 | Shelton et al. |
| 7,449,308 B2 | 11/2008 | Gerngross et al. |
| 7,449,616 B2 | 11/2008 | Pons et al. |
| 7,569,364 B2 | 8/2009 | Rosenthal et al. |
| 7,601,352 B1 | 10/2009 | Novak |
| 7,612,181 B2 | 11/2009 | Wu et al. |
| 7,655,231 B2 | 2/2010 | Shelton et al. |
| 7,655,232 B2 | 2/2010 | Pons et al. |
| 7,727,527 B2 | 6/2010 | Shelton |
| 8,007,800 B2 | 8/2011 | Shelton et al. |
| 8,034,346 B2 | 10/2011 | Shelton et al. |
| 8,088,384 B2 | 1/2012 | Pons et al. |
| 8,142,776 B2 | 3/2012 | Liu et al. |
| 2003/0031671 A1 | 2/2003 | Welt et al. |
| 2013/0330348 A1 | 12/2013 | Lacy et al. |

FOREIGN PATENT DOCUMENTS

| | | |
|---|---|---|
| WO | WO 1990/010700 A1 | 9/1990 |
| WO | WO 1990/14424 A1 | 11/1990 |
| WO | WO 1990/14443 A1 | 11/1990 |
| WO | WO 1991/05548 A1 | 5/1991 |
| WO | WO 1991/009966 A1 | 7/1991 |
| WO | WO 1991/09967 A1 | 7/1991 |
| WO | WO 1991/10737 A1 | 7/1991 |
| WO | WO 1991/10741 A1 | 7/1991 |
| WO | WO 1991/14430 A1 | 10/1991 |
| WO | WO 1991/17271 A1 | 11/1991 |
| WO | WO 1992/01047 A1 | 1/1992 |
| WO | WO 1992/02551 A1 | 2/1992 |
| WO | WO 1992/03461 A1 | 3/1992 |
| WO | WO 1992/009631 A1 | 6/1992 |
| WO | WO 1992/09690 A2 | 6/1992 |
| WO | WO 1992/11272 A1 | 7/1992 |
| WO | WO 1992/15679 A1 | 9/1992 |
| WO | WO 1992/18619 A1 | 10/1992 |
| WO | WO 1992/19244 A1 | 11/1992 |
| WO | WO 1992/20791 A1 | 11/1992 |
| WO | WO 1992/22324 A1 | 12/1992 |
| WO | WO 1993/01288 A1 | 1/1993 |
| WO | WO 1993/06213 A1 | 4/1993 |
| WO | WO 1993/006213 A1 | 4/1993 |
| WO | WO 1993/11236 A1 | 6/1993 |
| WO | WO 1994/02602 A1 | 2/1994 |
| WO | WO 1994/18219 A1 | 8/1994 |
| WO | WO 1995/15982 A1 | 6/1995 |
| WO | WO 1995/20401 A1 | 8/1995 |
| WO | WO 1995/025795 A1 | 9/1995 |
| WO | WO 1996/20698 A1 | 7/1996 |
| WO | WO 1996/33735 A1 | 10/1996 |
| WO | WO 1996/34096 A1 | 10/1996 |
| WO | WO 1997/015593 A1 | 5/1997 |
| WO | WO 1997/20032 A1 | 6/1997 |
| WO | WO 1997/021732 A1 | 6/1997 |
| WO | WO 1997/29131 A1 | 8/1997 |
| WO | WO 1997/32572 A1 | 9/1997 |
| WO | WO 1997/44013 A1 | 11/1997 |
| WO | WO 1998/06048 A2 | 2/1998 |
| WO | WO 1998/16654 A1 | 4/1998 |
| WO | WO 1998/017278 A1 | 4/1998 |
| WO | WO 1998/24893 A1 | 6/1998 |
| WO | WO 1998/31346 A1 | 7/1998 |
| WO | WO 1998/31700 A1 | 7/1998 |
| WO | WO 1998/50433 A2 | 11/1998 |
| WO | WO 1999/06834 A2 | 2/1999 |
| WO | WO 1999/15154 A1 | 4/1999 |
| WO | WO 1999/20253 A1 | 4/1999 |
| WO | WO 1999/45031 A1 | 9/1999 |
| WO | WO 1999/53049 A1 | 10/1999 |
| WO | WO 1999/053055 A2 | 10/1999 |
| WO | WO 1999/058572 A1 | 11/1999 |
| WO | WO 1999/66903 A2 | 12/1999 |
| WO | WO 2000/09560 A2 | 2/2000 |
| WO | WO 2000/37504 A2 | 6/2000 |
| WO | WO 2000/56772 A1 | 9/2000 |
| WO | WO 2000/069828 A1 | 11/2000 |
| WO | WO 2000/073344 A2 | 12/2000 |
| WO | WO 2001/064247 A2 | 9/2001 |
| WO | WO 2001/077332 A2 | 10/2001 |
| WO | WO 2001/078698 A2 | 10/2001 |
| WO | WO 2001/83525 A2 | 11/2001 |
| WO | WO 2002/072636 A2 | 9/2002 |
| WO | WO 2002/096458 A1 | 12/2002 |

(56) References Cited

FOREIGN PATENT DOCUMENTS

| WO | WO 2002/102232 A2 | 12/2002 |
|---|---|---|
| WO | WO 2003/022261 A1 | 3/2003 |
| WO | WO 2003/029456 A1 | 4/2003 |
| WO | WO 2003/060080 A2 | 7/2003 |
| WO | WO 2004/026329 A1 | 4/2004 |
| WO | WO 2004/032852 A2 | 4/2004 |
| WO | WO 2004/032870 A2 | 4/2004 |
| WO | WO 2004/056385 A2 | 7/2004 |
| WO | WO 2004/058184 A2 | 7/2004 |
| WO | WO 2004/065560 A2 | 8/2004 |
| WO | WO 2004/073653 A2 | 9/2004 |
| WO | WO 2004/096122 A2 | 11/2004 |
| WO | WO 2005/000194 A2 | 1/2005 |
| WO | WO 2005/019266 A2 | 3/2005 |
| WO | WO 2005/061540 A2 | 7/2005 |
| WO | WO 2005/111077 A2 | 11/2005 |
| WO | WO 2005/035575 A3 | 4/2006 |
| WO | WO 2006/077441 A1 | 7/2006 |
| WO | WO 2006/110883 A2 | 10/2006 |
| WO | WO 2006/121558 A2 | 11/2006 |
| WO | WO 2006/131951 A2 | 12/2006 |
| WO | WO 2006/131952 A1 | 12/2006 |
| WO | WO 2008/046033 A2 | 8/2008 |
| WO | WO 2009/023540 A1 | 2/2009 |
| WO | WO 2009/077993 A2 | 6/2009 |
| WO | WO 2009/091972 A2 | 7/2009 |
| WO | WO 2009/150623 A1 | 12/2009 |
| WO | WO 2010/027488 A2 | 3/2010 |
| WO | WO 2010/110838 A2 | 9/2010 |
| WO | WO 2010/128398 A1 | 11/2010 |
| WO | WO 2011/049758 A1 | 4/2011 |
| WO | WO 2011/116090 A1 | 9/2011 |
| WO | WO 2012/009254 A1 | 1/2012 |
| WO | WO 2012/024650 A2 | 2/2012 |

OTHER PUBLICATIONS

Kassel, et al., Clin, Exp. Allergy, 31 : 1432-40 (2001).
Kellermann et al., Current Opinion in Biotechnology, 13: 593-597 (2002).
Kipriyanov, et al., Mol. Immunol., 31: 1047-1058 (1994).
Kipriyanov, S.M., et al., Human Antibodies and Hybridomas, 6: 93-101 (1995).
Kryger, et al., J. Hand Surg. (Am.), 26: 635-644 (2001).
Lefranc et al., Nucleic Acids Res, 27:209-212 (1999).
Levi-Montalcini, Science 187: 113 (1975).
Little et al., Immunology Today 21 : 364-370 (2000).
MacCallum.,J Mol Biol 262(5):732-45 (1996).
Marchalonis et al., Adv Exp MedBiol 484: 13-30 (2001).
Martin, et al., Proc. Natl. Acad. Sci. USA, 86:9268-9272 (1989).
Okragly, et al., J. Urology 6: 438-441 (1999).
Padlan FASEB J. 9: 133-139 (1995).
Pearce, et al., J. Physiol, 372:379-393 (1986).
Saragovi, et al., Trends Pharmacol Sci. 21 : 93-98 (2000).
Schwartz, et al., J Photochem. Photobiol., B66: 195-200 (2002).
Shapiro et al., Crit. Rev. Immunol. 22(3): 183-200 (2002).
SIAM J. Applied Math., 48:1073-1082, Carrillo et al. (1988).
Steiner, et al., Am. J. Physiol., 261 :F792-798 (1991).
Taylor, L. D., et al. Nucl. Acids Res. 20:6287-6295 (1992).
Winnaker, From Genes to Clones (Verlagsgesellschaft, Weinheim, Germany (1987).
Zhu, Z. et al., J Clin. Oncol., 17: 241-228 (1999).
Adley et al. Phage Display of Peptides and Proteins : 277-291 (1996).
Aley et al., Neuroscience 71: 1083-1090 (1996).
Al-Lazikani et al., J. Mol. Biol. 273-927-948 (1997).
Aloe, et al., Arch. Rheum. 35:351-355 (1992).
Aloe, Clin and Exp Rheum 10: 203-204 (1992).
Aloe et al., Growth Factors 9: 149-155 (1993).
Aloe et al., Int. J. Tiss. Reac. XV(4) 139-143 (1993).
Aloe et al., Rheumatol. Int. 14: 249-252 (1995).
Aloe, Clin. Exp. Theumatol. 17: 632-633 (1999).
Amann et al., Pain 64: 323-329 (1995).
Andreev et al., Pain 63: 109-115 (1995).
Apfel et al., Mol. and Cell. Neuro. 7: 134-142 (1996).
Armour et al., Eur. J. Immunol. 29: 2613-2624 (1999).
Balint et al., Gene 137: 109-118 (1993).
Bellamy et al., J. Rheumatol. 15: 1833-1840 (1988).
Bellamy, N., Semin. Arthritis Rheum. 18: 14-17 (1989).
Bellini and Viola, Intern. J. Neuroscience 51: 329-330 (1990).
Berrera et al., Biophys J. 91: 2063-2071 (2006).
Bibel et al., Genes Dev. 14(23): 2919-2937 (2000).
Bird et al., Science 242: 423-426 (1988).
Bischoff et al., Blood 79: 2662-2669 (1992).
Boerner et al., J. Immuno. 147: 86-95 (1991).
Borsani et al., Nucleic Acids Research 18(13):4020 (1990).
BracciLaudiero, et al, Neurosci. Lett. 147:9-12 (1992).
Bracci-Laudiero, et al., Neuroreport 4:563-565 (1993).
Braun et al., Eur. J. Immunol. 28:3240-3251 (1998).
Brennan et al., Pain 64: 493-501 (1996).
Brennan, Soc. Neurosci. Abstract 349.4 (1998).
Brennan et al., Anesthesiology Clin. N. Am. 23: 1-20 (2005).
Brennan et al., ILAR Journal 40(3): 129-136 (1999).
Brosseau et al., The Cochrane Database of Systematic Reviews 4: Art No. CD004522 (2003).
Brown et al., Cancer Res. 47: 3577-3583 (1987).
Buchman et al., Development 118: 989-1001 (1993).
Capel et al., Immunomethods, 4:25-34 (1994).
Caraceni, J. Pain Symptom Management 23: 239-255 (2002).
Chao et al, Science 232:518-521 (1986).
Chaplan et al., J. Neuro. Methods 53: 55-63 (1994).
Choi et al., Life Sciences 73: 471-485 (2003).
Chothia et al. Nature 342:877-883 (1989).
Chothia and Lesk J. Mol. Biol. 196:901-917 (1987).
Chun et al., J. Cell Biol. 75: 705-711 (1977).
Christensen and Hulsebosch, Experimental Neurology 147(2):463-475 (1997).
Clackson et al., Nature 352:624-628 (1991).
Clohisy et al., Clin. Ortho. and Rel. Res. 415S: S279-S288 (2003).
Clynes et al., 1998, PNAS (USA), 95:652-656 (1998).
Covaceuzach et al., PLoS One 7: 1-12 (2012).
Covaceuzach et al., J. Mol. Biol. 4: 881-896 (2008).
Cromartie et al., J. Exp. Med. 146: 1585-1602 (1977).
Crowley et al. (1994) Cell 76:1001-1011 (1994).
Daughtery, Nucleic Acids Research 19: 2471-2476 (1991).
de Haas et al., J. Lab. Clin. Med., 126:330-41 (1995).
DeKock et al., Pain 92:373-380 (2001).
Dicou et al., J. Neuroimmun. 47:159-167 (1993).
Dicou et al., NeuroReport 5: 321-324 (1993).
Dicou et al., J. Neuroimmun. 49: 224 (1994).
Dicou et al., Autoimmunity 24: 1-9 (1996).
Dicou et al., J. Neuroimmun. 75: 200-203 (1997).
DiMarco et al. J. Biol Chem 268(30) 22838-22846 (1993).
Donnerer et al. Neuroscience 49(3): 693-698 (1992).
Eide et al., J. Neuroscience 16(10) 3123-3129 (1996).
Falcini et al., Ann. Rheum. Dis. 55: 745-748 (1996).
Felson et al., Arthritis Rheumatism 36: 729-740 (1993).
Fjell et al., J. Neurophysiol. 81: 803-810 (1999).
Foote and Winter, J. Mol. Biol. 224: 487-499 (1992).
Foster et al., J. Pathol. 197: 245-255 (2002).
Fries J., Rheumatol. 9:789-793 (1982).
Garaci et al., PNAS 96(24) 14013-14018 (1999).
Garcia-Castellano et al., Iowa Orthop. J. 20: 49-58 (2000).
Garrett et al., Neurosci. Lett. 230: 5-8 (1997).
Gavilondo and Larrick, BioTechniques 29: 128-145 (2000).
Gould et al., Brain Research 854: 19-29 (2000).
Griffiths et al., EMBO 12(2): 725-734 (1993).
Grosschedl et al., 41 Cell 885-897 (1985).
Gwak et al., Neurosci. Lett. 336: 117-120 (2003).
Halvorson et al., Cancer Res. 65: 9426-9435 (2005).
Haynes et al., Clinical Immunology 105(3): 315-325 (2002).
Hein, J., Meth. Enzymol. 183: 626-645 (1990).
Hefti et al., Trends in Pharmacological Sciences 27(2): 85-91 (2006).

(56) References Cited

OTHER PUBLICATIONS

Higgins and Sharp, CABIOS Comm. 5: 151-153 (1989).
Hill et al., Trends Pharmacol Sci 21(7): 244-246 (2000).
Holliger et al., PNAS 90:6444-6448 (1993).
Hongo et al., Hybridoma 19(3): 215-227 (2000).
Honore et al., Nature Med. 6: 521-528 (2000).
Honore et al., Neuroscience 98(3): 585-598 (2000).
Honore et al., Prog. Brain Res. 129: 389-397(2000).
Hoogenboom and Winter, J. Mol. Biol. 227: 381-388 (1992).
Horigome, et al., J. Biol. Chem. 268:14881-14887 (1993).
Huang and Reichardt, Ann. Rev. Neurosci. 24: 677-736 (2001).
Huse et al.,Intern. Rev. Immunol. 10: 129-137 (1993).
Iannone et al., Rheumatology 41: 1413-1418 (2002).
Jefferis, Chem. Immunol. 65: 111-128 (1997).
Johnson and Chiswell, Curr. Opin. Structural Biol. 3: 564-571 (1993).
Jones et al., Nature 321: 522-525 (1986).
Jones et al., Pain 79: 21-29 (1999).
Katz and Melzack, Surg. Clin. North Am. 79: 231-252 (1999).
Kawamoto et al., J. Immunol. 168: 6412-6419 (2002).
Kazemier et al., J. Immunol. Methods 194: 201-209 (1996).
Kidd et al, Br. J. Anaesthesia 87 (1) 3-11 (2001).
Kim et al., Eur. J. Immunol. 24: 2429-2434 (1994).
Klein et al, Cell 61: 647-656 (1990).
Knusel et al., J. Neurochem. 57: 955-962 (1990).
Knusel et al., J. Neurochem. 59: 715-721 (1990).
Koizumi et al., J. Neurosci. 8: 715-721 (1988).
Kuzuna and Kawai, Chem. Pharm. Bulletin 23: 1184-1191 (1975).
Lamballe et al., EMBO J. 12(8): 3083-3094 (1993).
Lane, N., Osteoarthritis and Cartilage Abstracts 20: S1-S9(2012).
Lane, et al., Arth. Rheum. 52(9): s461 (2005).
Lane et al., New England Journal of Medicine 363: 1521-1531 (2010).
Leon et al., PNAS 81: 3739-3743 (1994).
Levi-Montalcini and Angeletti, Physiol. Rev. 48; 534-569 (1968).
Lewin et al., J. Neuroscience 13: 2136-2148 (1993).
Lewin et al Eur. J. Neuroscience 6: 1903-1912 (1994).
Li et al., PNAS 95: 10884-10889 (1998).
Lindholm, et al., Eur. J. Neurosci. 2:795-801 (1990).
Lindsay, R., J Neuroscience 8(7): 2394-2405 (1988).
Lindsay, et al, Nature 337:362-364 (1989).
LoBuglio et al., PNAS 86: 4220-4224 (1989).
Lonberg et al., In. Tev. Immunol. 13:65-93 (1995).
Luger et al. Cancer Research 61: 4038-4047 ( (2001).
Mach et al., Neuroscience 113(1): 155-166 (2002).
Manni et al., Rheumatol. Int. 18: 97-102 (1998).
Mantyh et al., Nature Reviews Cancer 2(3): 201-209 (2002).
Marks et al., J. Mol. Biol. 222:581 597 (1991).
Marks et al., Bio Technol. 10:779-783 (1992).
Matsuda et al., PNAS 85(17):6508-6512 (1988).
McCafferty et al., Nature 348:552-554 (1990).
McDonald et al., Nature 354:411-414 (1991).
McMahon et al., Nature Medicine 1:774-780 (1995).
McMahon et al., Phil. Trans R. Soc. Land B 351(1338):431-440 (1996).
Meenan et al., Arthritis Rheumatism 25: 1048-1053 (1982).
Milstein., Nature 305: 537-540 (1983).
Moiniche et al., Anesthesiology 96: 725-741 (2002).
Molander and Grant, J. Comp. Neuro. 260: 246-255 (1987).
Molnar et al., Eur. J. Neuro. 10:3127-3140 (1998).
Morrison et al., PNAS 81: 6851-6855 (1984).
Muyldermans, Rev. Mol. Biotech. 74: 277-302 (2001).
Myers and Miller, CABIOS 4: 11-17 (1988).
Nanduri et al., J. Neuro. Res. 37: 433-444 (1994).
Niissalo et al., Ann. NY Acad. Sci. 966:384-399 (2002).
Otten et al., PNAS 86: 10059-10063 (1989).
Otten et al., Eur. J. Pharm. 106(1): 199-201 (1985).
Owens et al, J. Immunol. Methods 168(2):149-165 (1994).
Paulus et al., Arthritis and Rheumatism 33(4): 477-485 (1990).
Pearson., Arthritis-Rheum 2: 440-459 (1959).
Pelat et al., mAbs 1: 377-381 (2009).
Petersen et al., Neuroscience 83: 161-168 (1998).
Petty et al., Annals Neuro 36: 244-246 (1994).
Poljak, R.J., Structure 15(2): 1121-1123 (1994).
Pollock, J. Immunol. Meth. 231: 147-157 (1999).
Pons et al., Protein Science 8: 958-968 (1999).
Pozza et al., J Rheumatol 27(5): 1121-1127 (2000).
Presta, Current Opin. Immunol. 5-6: 640-656 (2006).
Prodromou and Pearl, Protein Engineering 5(8) 827-829 (1992).
Puigdellivol-Sanchez et al., Neuro. Lett. 251(3): 169-172 (1998).
Ramer and Bisby, Eur. J. Neuro. 11:837-846 (1999).
Ravetch and Kinet, 1991, Ann. Rev. Immunol., 9:457-492.
Raychaudhuri, Acta Derm Venereol. 78: 84-86 (1998).
Riechmann et al., Nature 332: 323-327 (1988).
Ro et al., Pain 79: 265-274 (1999).
Ro et al., Neuro. Letters 218:87-90 (1996).
Rosok et al., J. Biol. Chem. 271:22611-22618 (1996).
Roubenoff et al., J. Clin. Invest. 93: 2379-2386 (1994).
Roubenoff et al., Arthritis Rheum. 40(3): 534-539 (1997).
Ruberti et al., Cell. Molec. Neurobiol. 13(5): 559-568 (1993).
Rudikoff et al., PNAS 79: 1979-1983 (1982).
Schwei et al., J. Neuro 19(24): 10886-10897 (1999).
Sevcik et al., Pain 115: 128-141 (2005).
Shaw et al., J. Immunol. 138(12): 4534-4538 (1987).
Sheets et al., PNAS 95: 6157-6162 (1998).
Shelton and Reichardt, PNAS 81: 7951-7955 (1984).
Shelton et al., Rest Neurol and Neuro 8: 99-100 (1995).
Shih et al., J. Biol. Chem. 269: 27679-27686 (1994).
Smeyne, et al, Nature 368:246-249 (1994).
Stanisz., Annals of NY Acad. Sci. 917(1): 268-272 (2000).
Szekanecz et al., Arth. Rheum. 43 (6): 1266-1277 (2000).
Taglialatela et al., J. Neurochem. 66: 1826-1835 (1996).
Torcia, et al, Cell 85:345-356 (1996).
Ueyama, et al, J. Hypertens. 11: 1061-1065 (1993).
Ullrich et al., Nature 303: 821-825 (1983).
Umana et al., Nature Biotech. 17:176-180 (1999).
Urfer et al., Biochemistry 36: 4775-4781 (1997).
Vajdos et al., J. Mol. Biol. 320: 415-428 (2002).
Vanderah et al., Pain 92: 5-9 (2001).
Vaughan et al., Nat. Biotech. 14: 309-314 (1996).
Verhoeyen et al., Science 239: 1534-1536 (1988).
Vigneti et al., Year Immunol. 7: 146-149 (2000).
Waterhouse et al., Nucleic Acids Res 21: 2265-2266 (1993).
Wiesmann et al., Nature 401: 184-188 (1999).
Wilbur and Lipman, PNAS 80: 726-730 (1983).
Winter et al., Arth. Rheum. 9: 394-404 (1966).
Winter and Milstein, Nature 349: 293-299 (1991).
Winter et al., Ann. Rev. Immunol. 12: 433-455 (1994).
Woolf et al, Neuroscience 62: 327-331 (1994).
Woolf et al., J. Neurosci. 16(8): 2716-2723 (1996).
Woolf et al., J. Neurosci. 21(3): 1047-1055 (2001).
Wright and Morrison, TibTech 15: 26-32(1997).
Wu et al., J. Mol. Biol. 294:151-162 (1999).
Wyss and Wagner, Curr. Opin. Biotech. 7: 409-416 (1996).
Yamamoto et al., Brain Res 909: 138-144 (2001).
Yan et al., Clinical Science 80: 565-569 (1991).
Yelton et al., J. Immunol. 155: 1994-2004 (1995).
Yu et al., J. Neurosci. Meth. 115: 107-113 (2002).
Zahn et al., Reg. Anesth. Pain Med. 27: 514-516 (2002).
Zahn et al., J. Pain 5(3): 157-163 (2004).

A    B

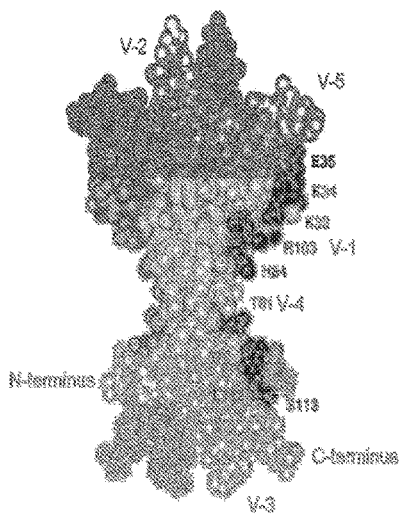

```
                1                              30
      dog  (1) SSSHPVFHRGEFSVCDSVSVWVGDKTTATD
      cat  (1) SSSHPVFHRGEFSVCDSVSVWVGDKTTATD
    human  (1) SSSHPIFHRGEFSVCDSVSVWVGDKTTATD
    mouse  (1) SSTHPVFHMGEFSVCDSVSVWVGDKTTATD
      rat  (1) SSTHPVFHMGEFSVCDSVSVWVGDKTTATD 31                             60
      dog (31) IKGKEVMVLGEVNINNSVFKQYFFETKCRD
      cat (31) IKGKEVMVLGEVNINNSVFKQYFFETKCRD
    human (31) IKGKEVMVLGEVNINNSVFKQYFFETKCRD
    mouse (31) IKGKEVTVLAEVNINNSVFRQYFFETKCRA
      rat (31) IKGKEVTVLGEVNINNSVFKQYFFETKCRA
```

```
         61                    90 91                   120
dog  (61) PTPVDSGCRGIDSKHWNSYCITTHTFVKAL TMDGKQAAWRFIRIDTACVCVLSRKAGRRA  (SEQ ID NO.52)
cat  (61) PTPVDSGCRGIDSKHWNSYCITTHTFVKAL TMDGKQAAWRFIRIDTACVCVLSRKAGRRA  (SEQ ID NO.53)
human(61) PNPVDSGCRGIDSKHWNSYCITTHTFVKAL TMDGKQAAWRFIRIDTACVCVLSRKAVRRA  (SEQ ID NO.54)
mouse(61) SNPVESGCRGIDSKHWNSYCITTHTFVKAL TTDEKQAAWRFIRIDTACVCVLSRKATRRG  (SEQ ID NO.55)
rat  (61) PNPVESGCRGIDSKHWNSYCITTHTFVKAL TTDDKQAAWRFIRIDTACVCVLSRKAARRG  (SEQ ID NO.56)
```

FIG. 6A and FIG. 6B

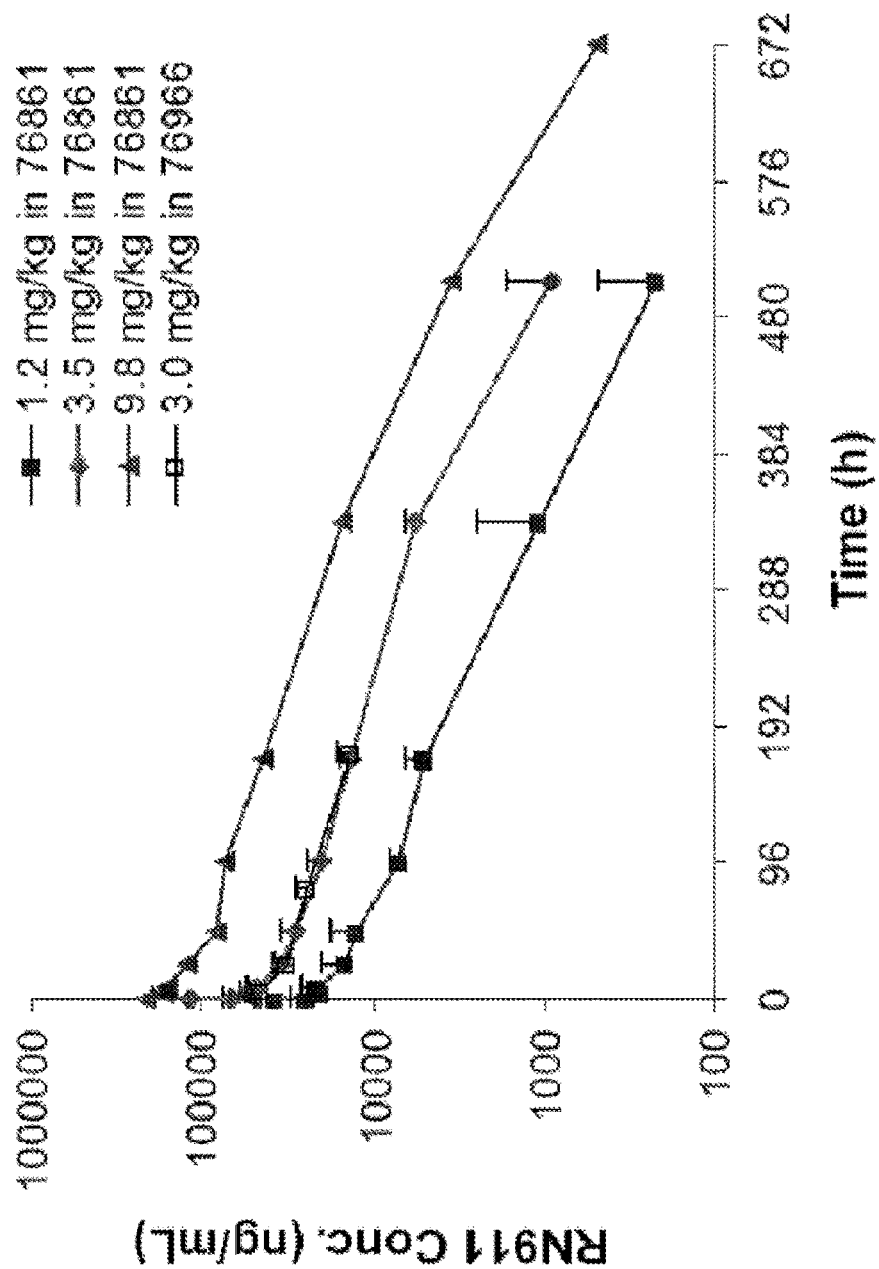

Bound RN911 After IV Administration to Dogs

Effects of Caninized Anti-NGF mAb PF-06442590 on Lameness in a Beagle Synovitis Pain Model Three treatment groups were compared:
1. Vehicle dosed SC;
2. PF-06442590 dosed at 5 mg/kg, IV
3. PF-06442590 dosed at 5 mg/kg, SC)
N= 8 beagles per treatment Group

SEQUENCE LISTING

```
<160> NUMBER OF SEQ ID NOS: 103

<210> SEQ ID NO 1
<211> LENGTH: 7
<212> TYPE: PRT
<213> ORGANISM: canine

<400> SEQUENCE: 1

Leu Ile Gly Tyr Asp Ile Asn
1               5

<210> SEQ ID NO 2
<211> LENGTH: 16
<212> TYPE: PRT
<213> ORGANISM: canine

<400> SEQUENCE: 2

Met Ile Trp Gly Asp Gly Thr Thr Asp Tyr Asn Ser Ala Leu Lys Ser
1               5                   10                  15

<210> SEQ ID NO 3
<211> LENGTH: 13
<212> TYPE: PRT
<213> ORGANISM: canine

<400> SEQUENCE: 3

Gly Gly Tyr Tyr Tyr Gly Thr Ser Tyr Tyr Phe Asp Tyr
1               5                   10

<210> SEQ ID NO 4
<211> LENGTH: 11
<212> TYPE: PRT
<213> ORGANISM: canine

<400> SEQUENCE: 4

Arg Ala Ser Gln Asp Ile Ser Asn His Leu Asn
1               5                   10

<210> SEQ ID NO 5
<211> LENGTH: 7
<212> TYPE: PRT
<213> ORGANISM: canine

<400> SEQUENCE: 5

Tyr Ile Ser Arg Phe His Ser
1               5

<210> SEQ ID NO 6
<211> LENGTH: 9
<212> TYPE: PRT
<213> ORGANISM: canine

<400> SEQUENCE: 6

Gln Gln Ser Lys Thr Leu Pro Tyr Thr
1               5

<210> SEQ ID NO 7
<211> LENGTH: 7
```

```
<212> TYPE: PRT
<213> ORGANISM: canine

<400> SEQUENCE: 7

Leu Ile Gln Tyr Asp Ile Asn
1               5

<210> SEQ ID NO 8
<211> LENGTH: 13
<212> TYPE: PRT
<213> ORGANISM: canine

<400> SEQUENCE: 8

Gly Gly Tyr Trp Tyr Ala Thr Ser Tyr Tyr Phe Asp Tyr
1               5                   10

<210> SEQ ID NO 9
<211> LENGTH: 13
<212> TYPE: PRT
<213> ORGANISM: canine

<400> SEQUENCE: 9

Gly Gly Tyr Trp Tyr Ala Thr Ser Tyr Tyr Phe Asp Tyr
1               5                   10

<210> SEQ ID NO 10
<211> LENGTH: 11
<212> TYPE: PRT
<213> ORGANISM: canine

<400> SEQUENCE: 10

Arg Ala Ser Gln Ser Ile Ser Asn Asn Leu Asn
1               5                   10

<210> SEQ ID NO 11
<211> LENGTH: 7
<212> TYPE: PRT
<213> ORGANISM: canine

<400> SEQUENCE: 11

Tyr Ile Ser Ser Phe His Ser
1               5

<210> SEQ ID NO 12
<211> LENGTH: 9
<212> TYPE: PRT
<213> ORGANISM: canine

<400> SEQUENCE: 12

Gln Gln Ser His Thr Leu Pro Tyr Thr
1               5

<210> SEQ ID NO 13
<211> LENGTH: 16
<212> TYPE: PRT
<213> ORGANISM: canine

<400> SEQUENCE: 13

Met Ile Trp Gly Thr Gly Thr Thr Asp Tyr Asn Ser Ala Leu Lys Ser
1               5                   10                  15

<210> SEQ ID NO 14
<211> LENGTH: 222
<212> TYPE: PRT
<213> ORGANISM: canine
```

<400> SEQUENCE: 14

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Gly Tyr
            20                  25                  30

Asp Ile Asn Trp Val Arg Gln Pro Pro Gly Lys Gly Leu Glu Trp Leu
        35                  40                  45

Gly Met Ile Trp Gly Asp Gly Thr Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Arg Thr Asp Asp Thr Ala Thr Tyr Ser Cys Ala
                85                  90                  95

Arg Gly Gly Tyr Tyr Tyr Gly Thr Ser Tyr Tyr Phe Asp Tyr Trp Gly
            100                 105                 110

Gln Gly Thr Thr Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp
    210                 215                 220

<210> SEQ ID NO 15
<211> LENGTH: 109
<212> TYPE: PRT
<213> ORGANISM: canine

<400> SEQUENCE: 15

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Tyr Gln Gln Lys Pro Asp Gly Thr Val Lys Leu Leu Ile
        35                  40                  45

Tyr Tyr Ile Ser Arg Phe His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Ser Lys Thr Leu Pro Tyr
                85                  90                  95

Thr Phe Gly Gly Gly Thr Lys Leu Glu Ile Lys Arg Ala
            100                 105

<210> SEQ ID NO 16
<211> LENGTH: 107
<212> TYPE: PRT
<213> ORGANISM: canine

<400> SEQUENCE: 16

Asp Ile Val Met Thr Gln Thr Pro Leu Ser Leu Ser Val Ser Pro Gly
1               5                   10                  15

Glu Thr Ala Ser Ile Ser Cys Arg Ala Ser Gln Asp Ile Ser Asn His
            20                  25                  30

Leu Asn Trp Phe Arg Gln Lys Pro Gly Gln Ser Pro Gln Arg Leu Ile
        35                  40                  45

Tyr Tyr Ile Ser Arg Phe His Ser Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Thr Gly Val Tyr Tyr Cys Gln Gln Ser Lys Thr Leu Pro Tyr
                85                  90                  95

Thr Phe Gly Ala Gly Thr Lys Leu Glu Ile Lys
            100                 105

<210> SEQ ID NO 17
<211> LENGTH: 121
<212> TYPE: PRT
<213> ORGANISM: canine

<400> SEQUENCE: 17

Glu Val Gln Leu Val Glu Ser Gly Gly Asp Leu Ala Arg Pro Gly Gly
1               5                   10                  15

Ser Leu Lys Leu Ser Cys Val Val Ser Gly Phe Ser Leu Ile Gly Tyr
            20                  25                  30

Asp Ile Asn Trp Val Arg Gln Ala Pro Gly Lys Gly Leu Gln Trp Val
        35                  40                  45

Thr Met Ile Trp Gly Asp Gly Thr Thr Asp Tyr Asn Ser Ala Leu Lys
    50                  55                  60

Ser Arg Phe Thr Val Ser Arg Asp Asn Ala Met Asn Thr Val Tyr Leu
65                  70                  75                  80

Gln Met Asn Ser Leu Arg Val Glu Asp Thr Ala Val Tyr Tyr Cys Ala
                85                  90                  95

Arg Gly Gly Tyr Tyr Gly Thr Ser Tyr Tyr Phe Asp Tyr Trp Gly
            100                 105                 110

Gln Gly Thr Leu Val Thr Val Ser Ser
        115                 120

<210> SEQ ID NO 18
<211> LENGTH: 107
<212> TYPE: PRT
<213> ORGANISM: canine

<400> SEQUENCE: 18

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Asp Ile Ser Asn His
            20                  25                  30

Leu Asn Trp Phe Arg Gln Lys Pro Gly Gln Ser Pro Gln Arg Leu Ile
        35                  40                  45

Tyr Tyr Ile Ser Arg Phe His Ser Gly Val Pro Ser Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Ser Lys Thr Leu Pro Tyr
                    85                  90                  95

Thr Phe Gly Gln Gly Thr Lys Leu Glu Ile Lys
            100                 105

<210> SEQ ID NO 19
<211> LENGTH: 107
<212> TYPE: PRT
<213> ORGANISM: canine

<400> SEQUENCE: 19

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Asp Ile Ser Asn His
            20                  25                  30

Leu Asn Trp Phe Arg Gln Lys Pro Asp Gly Thr Val Lys Leu Leu Ile
        35                  40                  45

Tyr Tyr Ile Ser Arg Phe His Ser Gly Val Pro Ser Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Ser Lys Thr Leu Pro Tyr
                    85                  90                  95

Thr Phe Gly Gln Gly Thr Lys Leu Glu Ile Lys
            100                 105

<210> SEQ ID NO 20
<211> LENGTH: 106
<212> TYPE: PRT
<213> ORGANISM: canine

<400> SEQUENCE: 20

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Asp Ile Ser Asn His
            20                  25                  30

Leu Asn Trp Tyr Gln Gln Lys Pro Asp Gly Thr Val Lys Leu Leu Ile
        35                  40                  45

Tyr Tyr Ile Ser Arg Phe His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Ser Lys Thr Leu Pro Tyr
                    85                  90                  95

Thr Phe Gly Gly Gly Thr Lys Leu Glu Ile
            100                 105

<210> SEQ ID NO 21
<211> LENGTH: 106
<212> TYPE: PRT
<213> ORGANISM: canine

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Phe Arg Gln Lys Pro Gly Gln Ser Pro Gln Arg Leu Ile

```
                35                  40                  45
Tyr Tyr Ile Ser Arg Phe His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Ser Lys Thr Leu Pro Tyr
                 85                  90                  95

Thr Phe Gly Gly Gly Thr Lys Leu Glu Ile
                100                 105

<210> SEQ ID NO 22
<211> LENGTH: 106
<212> TYPE: PRT
<213> ORGANISM: canine

<400> SEQUENCE: 22

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn His
                20                  25                  30

Leu Asn Trp Tyr Gln Gln Lys Pro Asp Gly Thr Val Lys Leu Leu Ile
             35                  40                  45

Tyr Tyr Ile Ser Arg Phe His Ser Gly Val Pro Ser Arg Phe Ser Gly
 50                  55                  60

Ser Gly Ser Gly Thr Asp Phe Thr Leu Arg Ile Ser Arg Val Glu Ala
 65                  70                  75                  80

Asp Asp Ala Gly Val Tyr Tyr Cys Gln Gln Ser Lys Thr Leu Pro Tyr
                 85                  90                  95

Thr Phe Gly Gly Gly Thr Lys Leu Glu Ile
                100                 105

<210> SEQ ID NO 23
<211> LENGTH: 106
<212> TYPE: PRT
<213> ORGANISM: canine

<400> SEQUENCE: 23

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn His
                20                  25                  30

Leu Asn Trp Tyr Gln Gln Lys Pro Asp Gly Thr Val Lys Leu Leu Ile
             35                  40                  45

Tyr Tyr Ile Ser Arg Phe His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Ser Lys Thr Leu Pro Tyr
                 85                  90                  95

Thr Phe Gly Gln Gly Thr Lys Leu Glu Ile
                100                 105

<210> SEQ ID NO 24
<211> LENGTH: 107
<212> TYPE: PRT
<213> ORGANISM: canine

<400> SEQUENCE: 24
```

```
Asp Ile Val Met Thr Gln Thr Pro Leu Ser Leu Ser Val Ser Pro Gly
1               5                   10                  15

Glu Thr Ala Ser Ile Ser Cys Arg Ala Ser Gln Ser Ile Ser Asn Asn
            20                  25                  30

Leu Asn Trp Phe Arg Gln Lys Pro Gly Gln Ser Pro Gln Arg Leu Ile
        35                  40                  45

Tyr Tyr Ile Ser Arg Phe His Ser Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Thr Gly Val Tyr Tyr Cys Gln Gln Ser His Thr Leu Pro Tyr
                85                  90                  95

Thr Phe Gly Ala Gly Thr Lys Leu Glu Ile Lys
            100                 105
```

<210> SEQ ID NO 25
<211> LENGTH: 121
<212> TYPE: PRT
<213> ORGANISM: canine

<400> SEQUENCE: 25

```
Glu Val Gln Leu Val Glu Ser Gly Gly Asp Leu Ala Arg Pro Gly Gly
1               5                   10                  15

Ser Leu Lys Leu Ser Cys Val Val Ser Gly Phe Ser Leu Ile Gly Tyr
            20                  25                  30

Asp Ile Asn Trp Val Arg Gln Ala Pro Gly Lys Gly Leu Gln Trp Val
        35                  40                  45

Thr Met Ile Trp Gly Asp Gly Thr Thr Asp Tyr Asn Ser Ala Leu Lys
    50                  55                  60

Ser Arg Phe Thr Val Ser Arg Asp Asn Ala Met Asn Thr Val Tyr Leu
65                  70                  75                  80

Gln Met Asn Ser Leu Arg Val Glu Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser
        115                 120
```

<210> SEQ ID NO 26
<211> LENGTH: 107
<212> TYPE: PRT
<213> ORGANISM: canine

<400> SEQUENCE: 26

```
Asp Ile Val Met Thr Gln Thr Pro Leu Ser Leu Ser Val Ser Pro Gly
1               5                   10                  15

Glu Thr Ala Ser Ile Ser Cys Arg Ala Ser Gln Ser Ile Ser Asn Asn
            20                  25                  30

Leu Asn Trp Phe Arg Gln Lys Pro Gly Gln Ser Pro Gln Arg Leu Ile
        35                  40                  45

Tyr Tyr Ile Ser Ser Phe His Ser Gly Val Pro Asp Arg Phe Ser Gly
    50                  55                  60

Ser Gly Ser Gly Thr Asp Phe Thr Leu Arg Ile Ser Arg Val Glu Ala
65                  70                  75                  80

Asp Asp Thr Gly Val Tyr Tyr Cys Gln Gln Ser His Thr Leu Pro Tyr
                85                  90                  95
```

```
Thr Phe Gly Ala Gly Thr Lys Leu Glu Ile Lys
            100                 105
```

<210> SEQ ID NO 27
<211> LENGTH: 121
<212> TYPE: PRT
<213> ORGANISM: canine

<400> SEQUENCE: 27

```
Glu Val Gln Leu Val Glu Ser Gly Gly Asp Leu Ala Arg Pro Gly Gly
1               5                   10                  15

Ser Leu Lys Leu Ser Cys Val Val Ser Gly Phe Ser Leu Ile Gln Tyr
            20                  25                  30

Asp Ile Asn Trp Val Arg Gln Ala Pro Gly Lys Gly Leu Gln Trp Val
        35                  40                  45

Thr Met Ile Trp Gly Asp Gly Thr Thr Asp Tyr Asn Ser Ala Leu Lys
    50                  55                  60

Ser Arg Phe Thr Val Ser Arg Asp Asn Ala Met Asn Thr Val Tyr Leu
65                  70                  75                  80

Gln Met Asn Ser Leu Arg Val Glu Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser
            115                 120
```

<210> SEQ ID NO 28
<211> LENGTH: 121
<212> TYPE: PRT
<213> ORGANISM: canine

<400> SEQUENCE: 28

```
Glu Val Gln Leu Val Glu Ser Gly Gly Asp Leu Ala Arg Pro Gly Gly
1               5                   10                  15

Ser Leu Lys Leu Ser Cys Val Val Ser Gly Phe Ser Leu Ile Glu Tyr
            20                  25                  30

Asp Ile Asn Trp Val Arg Gln Ala Pro Gly Lys Gly Leu Gln Trp Val
        35                  40                  45

Thr Met Ile Trp Gly Asp Gly Thr Thr Asp Tyr Asn Ser Ala Leu Lys
    50                  55                  60

Ser Arg Phe Thr Val Ser Arg Asp Asn Ala Met Asn Thr Val Tyr Leu
65                  70                  75                  80

Gln Met Asn Ser Leu Arg Val Glu Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser
            115                 120
```

<210> SEQ ID NO 29
<211> LENGTH: 121
<212> TYPE: PRT
<213> ORGANISM: canine

<400> SEQUENCE: 29

```
Glu Val Gln Leu Val Glu Ser Gly Gly Asp Leu Ala Arg Pro Gly Gly
1               5                   10                  15
```

Ser Leu Lys Leu Ser Cys Val Val Ser Gly Phe Ser Leu Ile Glu Tyr
            20                  25                  30

Asp Ile Asn Trp Val Arg Gln Ala Pro Gly Lys Gly Leu Gln Trp Val
             35                  40                  45

Thr Met Ile Trp Gly Thr Gly Thr Asp Tyr Asn Ser Ala Leu Lys
 50                  55                  60

Ser Arg Phe Thr Val Ser Arg Asp Asn Ala Met Asn Thr Val Tyr Leu
65                  70                  75                  80

Gln Met Asn Ser Leu Arg Val Glu Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser
            115                 120

<210> SEQ ID NO 30
<211> LENGTH: 107
<212> TYPE: PRT
<213> ORGANISM: canine

<400> SEQUENCE: 30

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Ser Ile Ser Asn Asn
            20                  25                  30

Leu Asn Trp Phe Arg Gln Lys Pro Asp Gly Thr Val Lys Leu Leu Ile
            35                  40                  45

Tyr Tyr Ile Ser Ser Phe His Ser Gly Val Pro Ser Arg Phe Ser Gly
        50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Ser His Thr Leu Pro Tyr
                85                  90                  95

Thr Phe Gly Gln Gly Thr Lys Leu Glu Ile Lys
            100                 105

<210> SEQ ID NO 31
<211> LENGTH: 321
<212> TYPE: DNA
<213> ORGANISM: canine

<400> SEQUENCE: 31
gacatccaga tgacccagac caccagcagc ctgagcgcca gcctgggcga cagagtgacc      60
atcagctgcc gggccagcca ggacatcagc aaccacctga actggtatca gcagaaaccc     120
gacggcaccg tgaagctgct gatctactac atcagccggt tccacagcgg cgtgcccagc     180 agatttctg gcagcggcag cggcaccgac tacagcctga ccatctccaa cctggaacag     240
gaagatatcg ccacctactt ttgccagcag agcaagaccc tgccctacac cttcggcgga    300
ggtaccaagc tggagatcaa g                                               321

<210> SEQ ID NO 32
<211> LENGTH: 363
<212> TYPE: DNA
<213> ORGANISM: canine

<400> SEQUENCE: 32
caggtgcagc tgaaagagtc cggccctggc ctggtggctc ctagccagag cctgagcatc      60

```
acctgtaccg tgtccggctt cagcctgatc ggctacgaca tcaactgggt gcgccagcct      120
cctggaaagg gcctggaatg gctgggcatg atctggggcg acggcaccac cgactacaac      180
agcgccctga gtcccggct gagcatcagc aaggacaaca gcaagagcca ggtgttcctg       240
aagatgaaca gcctgcggac cgacgatacc gccacctaca gctgcgccag aggcggctac      300
tactacggca ccagctacta cttcgactac tggggccagg ggacaacgct caccgtctcg      360
agc                                                                    363

<210> SEQ ID NO 33
<211> LENGTH: 321
<212> TYPE: DNA
<213> ORGANISM: canine

<400> SEQUENCE: 33
gacatcgtga tgacccagac cccccctgagc ctgagcgtgt ccctggcga  dacagccagc     60 atcagctgcc gggccagcca ggacatcagc aaccacctga actggttccg gcagaagccc      120
ggccagagcc cccagagact gatctactac atcagccggt ccacagcgg cgtgcccgac      180 agatttccg gcagcggctc cggcaccgac ttcaccctgc ggatcagccg ggtggaagcc       240
gacgacaccg gcgtgtacta ctgccagcag agcaagaccc tgccctacac ctttggcgcc     300
ggtaccaagc tggagatcaa g                                                321

<210> SEQ ID NO 34
<211> LENGTH: 363
<212> TYPE: DNA
<213> ORGANISM: canine

<400> SEQUENCE: 34
gaggtgcagc tggtggaatc tggcggcgac ctggccagac ctggcggcag cctgaagctg      60
agctgcgtgg tgtccggctt cagcctgatc ggctacgaca tcaactgggt ccgccaggcc      120
cctggcaagg gcctgcagtg gtcacaatg atctggggcg acggcaccac cgactacaac       180
agcgccctga gtcccggtt caccgtgtct cgggacaacg ccatgaacac cgtgtacctg       240
cagatgaaca gcctgcgggt ggaagatacc gccgtgtact actgcgccag aggcggctac      300
tactacggca ccagctacta cttcgactac tggggccagg gcacactggt cacagtctcg      360
agc                                                                    363

<210> SEQ ID NO 35
<211> LENGTH: 321
<212> TYPE: DNA
<213> ORGANISM: canine

<400> SEQUENCE: 35
gacatcgtga tgacccagac acctctgtca ctgagcgtgt ccccagggga acccgcctct      60
atcagttgcc gggctagtca ggatatttca aaccacctga attggttcag acagaagcca      120
gggcagagcc cccagagact gatctactat attagcaggt tccattccgg agtgccctct     180
cgcttttcag gcagcgggtc cggaacagac tttactctgc ggatctccag agtggaagcc      240
gacgatgctg gcgtgtacta ttgccagcag tctaaaaccc tgccctacac cttcggccag      300
ggtaccaagc tggagatcaa g                                                321

<210> SEQ ID NO 36
<211> LENGTH: 321
<212> TYPE: DNA
```

<213> ORGANISM: canine

<400> SEQUENCE: 36

| | | | | | |
|---|---|---|---|---|---|
| gacatcgtga | tgacccagac | acctctgtca | ctgagcgtgt | ccccagggga | acccgcctct | 60 |
| atcagttgcc | gggctagtca | ggatatttca | aaccacctga | actggttcag | acagaagcca | 120 |
| gatgggaccg | tcaagctact | gatctactat | attagcaggt | tccattccgg | agtgccctct | 180 |
| cgcttttcag | gcagcgggtc | cggaacagac | tttactctgc | ggatctccag | agtggaagcc | 240 |
| gacgatgctg | gcgtgtacta | ttgccagcag | tctaaaaccc | tgccctacac | attcggccag | 300 |
| ggtaccaagc | tggagatcaa | g | | | | 321 |

<210> SEQ ID NO 37
<211> LENGTH: 321
<212> TYPE: DNA
<213> ORGANISM: canine

<400> SEQUENCE: 37

| | | | | | |
|---|---|---|---|---|---|
| gacatcgtga | tgacccagac | cccctgagc | ctgagcgtgt | ccctggcga | gacagccagc | 60 |
| atcagctgcc | gggccagcca | gagcatcagc | aacaacctga | actggttccg | gcagaagccc | 120 |
| ggccagagcc | cccagagact | gatctactac | atcagcggt | tccacagcgg | cgtgcccgac | 180 |
| agattttccg | gcagcggctc | cggcaccgac | ttcaccctgc | ggatcagccg | ggtggaagcc | 240 |
| gacgacaccg | gcgtgtacta | ctgccagcag | agccacaccc | tgccctacac | ctttggcgcc | 300 |
| ggtaccaagc | tggaaatcaa | g | | | | 321 |

<210> SEQ ID NO 38
<211> LENGTH: 363
<212> TYPE: DNA
<213> ORGANISM: canine

<400> SEQUENCE: 38

| | | | | | |
|---|---|---|---|---|---|
| gaggtgcagc | tggtggaatc | tggcggcgac | ctggccagac | ctggcggcag | cctgaagctg | 60 |
| agctgcgtgg | tgtccggctt | cagcctgatc | ggctacgaca | tcaactgggt | ccgccaggcc | 120 |
| cctggcaagg | gcctgcagtg | ggtcacaatg | atctggggcg | acggcaccac | cgactacaac | 180 |
| agcgccctga | agtcccggtt | caccgtgtct | cgggacaacg | ccatgaacac | cgtgtacctg | 240 |
| cagatgaaca | gcctgcgggt | ggaagatacc | gccgtgtact | actgcgccag | aggcggctac | 300 |
| tggtacgcca | ccagctacta | cttcgactac | tggggccagg | gcacactggt | cacagtctcg | 360 |
| agc | | | | | | 363 |

<210> SEQ ID NO 39
<211> LENGTH: 321
<212> TYPE: DNA
<213> ORGANISM: canine

<400> SEQUENCE: 39

| | | | | | |
|---|---|---|---|---|---|
| gacatcgtga | tgacccagac | cccctgagc | ctgagcgtgt | ccctggcga | gacagccagc | 60 |
| atcagctgcc | gggccagcca | gagcatcagc | aacaacctga | actggttccg | gcagaagccc | 120 |
| ggccagagcc | cccagagact | gatctactac | atcagctcgt | tccacagcgg | cgtgcccgac | 180 |
| agattttccg | gcagcggctc | cggcaccgac | ttcaccctgc | ggatcagccg | ggtggaagcc | 240 |
| gacgacaccg | gcgtgtacta | ctgccagcag | agccacaccc | tgccctacac | ctttggcgcc | 300 |
| ggtaccaagc | tggaaatcaa | g | | | | 321 |

```
<210> SEQ ID NO 40
<211> LENGTH: 363
<212> TYPE: DNA
<213> ORGANISM: canine

<400> SEQUENCE: 40
gaggtgcagc tggtggaatc tggcggcgac ctggccagac ctggcggcag cctgaagctg      60
agctgcgtgg tgtccggctt cagcctgatc cagtacgaca tcaactgggt ccgccaggcc     120
cctggcaagg gcctgcagtg ggtcacaatg atctggggcg acggcaccac cgactacaac     180
agcgccctga agtcccggtt caccgtgtct cgggacaacg ccatgaacac cgtgtacctg     240
cagatgaaca gcctgcgggt ggaagatacc gccgtgtact actgcgccag aggcggctac     300
tggtacgcca ccagctacta cttcgactac tggggccagg gcacactggt cacagtctcg     360
agc                                                                    363

<210> SEQ ID NO 41
<211> LENGTH: 363
<212> TYPE: DNA
<213> ORGANISM: canine

<400> SEQUENCE: 41
gaggtgcagc tggtggaatc tggcggcgac ctggccagac ctggcggcag cctgaagctg      60
agctgcgtgg tgtccggctt cagcctgatc gaatacgaca tcaactgggt ccgccaggcc     120
cctggcaagg gcctgcagtg ggtcacaatg atctggggcg acggcaccac cgactacaac     180
agcgccctga agtcccggtt caccgtgtct cgggacaacg ccatgaacac cgtgtacctg     240
cagatgaaca gcctgcgggt ggaagatacc gccgtgtact actgcgccag aggcggctac     300
tggtacgcca ccagctacta cttcgactac tggggccagg gcacactggt cacagtctcg     360
agc                                                                    363

<210> SEQ ID NO 42
<211> LENGTH: 363
<212> TYPE: DNA
<213> ORGANISM: canine

<400> SEQUENCE: 42
gaggtgcagc tggtggaatc tggcggcgac ctggccagac ctggcggcag cctgaagctg      60
agctgcgtgg tgtccggctt cagcctgatc gaatacgaca tcaactgggt ccgccaggcc     120
cctggcaagg gcctgcagtg ggtcacaatg atctggggca ccggcaccac cgactacaac     180
agcgccctga agtcccggtt caccgtgtct cgggacaacg ccatgaacac cgtgtacctg     240
cagatgaaca gcctgcgggt ggaagatacc gccgtgtact actgcgccag aggcggctac     300
tggtacgcca ccagctacta cttcgactac tggggccagg gcacactggt cacagtctcg     360
agc                                                                    363

<210> SEQ ID NO 43
<211> LENGTH: 321
<212> TYPE: DNA
<213> ORGANISM: canine

<400> SEQUENCE: 43
gacatcgtga tgacccagac acctctgtca ctgagcgtgt ccccagggga acccgcctct      60
atcagttgcc gggccagcca gagcatcagc aacaacctga actggttcag acagaagcca     120
gatgggaccg tcaagctact gatctactac atcagctcgt tccacagcgg agtgccctct     180
```

```
cgcttttcag gcagcgggtc cggaacagac tttactctgc ggatctccag agtggaagcc      240
gacgatgctg gcgtgtacta ttgccagcag agccacaccc tgccctacac cttcggccag      300
ggtaccaagc tggaaatcaa g                                                 321
```

<210> SEQ ID NO 44
<211> LENGTH: 335
<212> TYPE: PRT
<213> ORGANISM: canine

<400> SEQUENCE: 44

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Ala Ala Gly Ala Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335
```

<210> SEQ ID NO 45

<211> LENGTH: 1005
<212> TYPE: DNA
<213> ORGANISM: canine

<400> SEQUENCE: 45

| | | | | | |
|---|---|---|---|---|---|
| gcctcaacaa | ctgctcctag | cgtgtttccc | ctggcccta | gctgcggaag | tacctcaggc | 60 |
| agcacagtgg | ccctggcttg | tctggtgtct | ggatatttcc | ctgagccagt | gaccgtgagt | 120 |
| tggaacagcg | gctctctgac | ctccggggtg | cacacatttc | catctgtgct | gcagtctagt | 180 |
| ggcctgtact | ccctgtcaag | catggtgact | gtgccttcct | ctaggtggcc | atcagaaact | 240 |
| ttcacctgca | acgtggccca | tcccgccagc | aagaccaaag | tggacaagcc | cgtgcctaaa | 300 |
| agggagaatg | gaagggtgcc | aagaccacct | gattgcccta | gtgtccagc | tccagaagcg | 360 |
| gcgggagcac | caagcgtgtt | catctttcca | cccaagccca | agacacact | gctgattgct | 420 |
| agaactcccg | aggtgacctg | cgtggtggtg | gacctggatc | cagaggaccc | cgaagtgcag | 480 |
| atctcctggt | tcgtggatgg | gaagcagatg | cagacagcca | aaactcagcc | tcggaggaa | 540 |
| cagtttaacg | gaacctatag | agtggtgtct | gtgctgccaa | ttggacacca | ggactggctg | 600 |
| aagggcaaac | agtttacatg | caaggtgaac | aacaaggccc | tgcctagtcc | aatcgagagg | 660 |
| actatttcaa | aagctagggg | acaggctcat | cagccttccg | tgtatgtgct | gcctccatcc | 720 |
| cgggaggaac | tgtctaagaa | cacagtgagt | ctgacttgtc | tgatcaaaga | tttctttccc | 780 |
| cctgacattg | atgtggagtg | gcagagcaat | gggcagcagg | agccagaatc | caagtacaga | 840 |
| accacaccac | cccagctgga | cgaagatggc | tcctatttcc | tgtacagtaa | gctgtcagtg | 900 |
| gacaaatcta | ggtggcagcg | cggggatacc | tttatctgcg | ccgtgatgca | cgaggctctg | 960 |
| cacaatcatt | acacacaaga | aagtctgtca | catagccccg | gcaag | | 1005 |

<210> SEQ ID NO 46
<211> LENGTH: 106
<212> TYPE: PRT
<213> ORGANISM: canine

<400> SEQUENCE: 46

Arg Asn Asp Ala Gln Pro Ala Val Tyr Leu Phe Gln Pro Ser Pro Asp
1               5                   10                  15

Gln Leu His Thr Gly Ser Ala Ser Val Val Cys Leu Leu Asn Ser Phe
            20                  25                  30

Tyr Pro Lys Asp Ile Asn Val Lys Trp Lys Val Asp Gly Val Ile Gln
        35                  40                  45

Asp Thr Gly Ile Gln Glu Ser Val Thr Glu Asp Lys Asp Ser Thr
    50                  55                  60

Tyr Ser Leu Ser Ser Thr Leu Thr Met Ser Ser Thr Glu Tyr Leu Ser
65                  70                  75                  80

His Glu Leu Tyr Ser Cys Glu Ile Thr His Lys Ser Leu Pro Ser Thr
                85                  90                  95

Leu Ile Lys Ser Phe Gln Arg Ser Glu Cys
            100                 105

<210> SEQ ID NO 47
<211> LENGTH: 318
<212> TYPE: DNA
<213> ORGANISM: canine

<400> SEQUENCE: 47

| | | | | | |
|---|---|---|---|---|---|
| aggaacgacg | cccagcctgc | tgtgtatctg | tttcagccct | cccctgatca | gctgcacact | 60 |

-continued

```
ggctctgcta gtgtggtgtg tctgctgaac agcttctacc caaaggatat caatgtgaag    120
tggaaagtgg acggcgtgat ccaggatact gggattcagg agtccgtgac cgaacaggac    180
aaagattcaa catatagcct gagctccact ctgaccatgt ctagtaccga gtacctgagc    240
cacgaactgt attcctgcga gatcactcat aagtccctgc cctctaccct gatcaagagc    300
ttccagagat cagagtgt                                                  318
```

<210> SEQ ID NO 48
<211> LENGTH: 1008
<212> TYPE: DNA
<213> ORGANISM: canine

<400> SEQUENCE: 48

```
gcctcaacaa ctgctcctag cgtgtttccc ctggccccta gctgcggaag tacctcaggc     60
agcacagtgg ccctggcttg tctggtgtct ggatatttcc ctgagccagt gaccgtgagt    120
tggaacagcg gctctctgac ctccggggtg cacacatttc catctgtgct gcagtctagt    180
ggcctgtact ccctgtcaag catggtgact gtgccttcct ctaggtggcc atcagaaact    240
ttcacctgca acgtgcccca tcccgccagc aagaccaaag tggacaagcc cgtgcctaaa    300
agggagaatg gaagggtgcc aagaccacct gattgcccta gtgtccagc tccagaaatg     360 ctggaggac aagcgtgtt catctttcca cccaagccca agacacact gctgattgct       420 agaactcccg aggtgacctg cgtggtggtg gacctggatc cagaggaccc cgaagtgcag    480
atctcctggt tcgtggatgg gaagcagatg cagacagcca aaactcagcc tcgggaggaa    540
cagtttaacg gaacctatag agtggtgtct gtgctgccaa ttggacacca ggactggctg    600
aagggcaaac agtttacatg caaggtgaac aacaaggccc tgcctagtcc aatcgagagg    660
actatttcaa aagctagggg acaggctcat cagccttccg tgtatgtgct gcctccatcc    720
cgggaggaac tgtctaagaa cacagtgagt ctgacttgtc tgatcaaaga tttctttccc    780
cctgacattg atgtggagtg gcagagcaat gggcagcagg agccagaatc caagtacaga    840
accacaccac cccagctgga cgaagatggc tcctatttcc tgtacagtaa gctgtcagtg    900
gacaaatcta ggtggcagcg cggggatacc tttatctgcg ccgtgatgca cgaggctctg    960
cacaatcatt acacacaaga aagtctgtca catagccccg gcaagtag              1008
```

<210> SEQ ID NO 49
<211> LENGTH: 335
<212> TYPE: PRT
<213> ORGANISM: canine

<400> SEQUENCE: 49

```
Ala Ser Thr Thr Ala Pro Ser Val Phe Pro Leu Ala Pro Ser Cys Gly
 1               5                  10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
```

```
            100                 105                 110
Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
        130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                    165                 170                 175

Pro Arg Glu Glu Gln Phe Asn Gly Thr Tyr Arg Val Val Ser Val Leu
                180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
        210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                    245                 250                 255

Asp Phe Phe Pro Pro Asp Ile Asp Val Glu Trp Gln Ser Asn Gly Gln
                260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
        290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                    325                 330                 335

<210> SEQ ID NO 50
<211> LENGTH: 201
<212> TYPE: PRT
<213> ORGANISM: canine

<400> SEQUENCE: 50

Gln His Ser Leu Asp Thr Ala Leu Arg Arg Ala Arg Ser Ala Pro Ala
1               5                   10                  15

Gly Ala Ile Ala Ala Arg Val Thr Gly Gln Thr Arg Asn Ile Thr Val
            20                  25                  30

Asp Pro Lys Leu Phe Lys Lys Arg Arg Leu Arg Ser Pro Arg Val Leu
        35                  40                  45

Phe Ser Thr His Pro Pro Val Ala Ala Asp Ala Gln Asp Leu Asp
    50                  55                  60

Leu Glu Ala Gly Ser Thr Ala Ser Val Asn Arg Thr His Arg Ser Lys
65                  70                  75                  80

Arg Ser Ser Ser His Pro Val Phe His Arg Gly Glu Phe Ser Val Cys
                    85                  90                  95

Asp Ser Val Ser Val Trp Val Gly Asp Lys Thr Thr Ala Thr Asp Ile
                100                 105                 110

Lys Gly Lys Glu Val Met Val Leu Gly Glu Val Asn Ile Asn Asn Ser
            115                 120                 125

Val Phe Lys Gln Tyr Phe Phe Glu Thr Lys Cys Arg Asp Pro Thr Pro
        130                 135                 140
```

Val Asp Ser Gly Cys Arg Gly Ile Asp Ser Lys His Trp Asn Ser Tyr
145                 150                 155                 160

Cys Thr Thr Thr His Thr Phe Val Lys Ala Leu Thr Met Asp Gly Lys
                165                 170                 175

Gln Ala Ala Trp Arg Phe Ile Arg Ile Asp Thr Ala Cys Val Cys Val
            180                 185                 190

Leu Ser Arg Lys Ala Gly Arg Arg Ala
        195                 200

<210> SEQ ID NO 51
<211> LENGTH: 778
<212> TYPE: DNA
<213> ORGANISM: canine

<400> SEQUENCE: 51
atgtccatgt tgttctacac tctgatcaca gctcttctga tcggcatccg ggcagaaccg     60
catccagaga gccatgtccc agcaggacac gccatccccc acgcccactg gactaagctt    120
cagcattccc ttgacacagc cctccgcaga gcccgcagcg ccccggccgg ggcaatagct    180
gccagggtga cagggcagac cgcaacatc actgtggatc ccaaactctt taaaaagcgg    240
cgactgcgtt cgccccgcgt gctgttcagc acgcaccccc cacctgtggc tgcggacgct    300
caggacctgg acctggaggc cggcagcacc gcctccgtca acaggactca caggagcaag    360
cggtcttcgt cccaccctgt cttccaccgg ggggagttct cggtgtgcga cagcgtcagc    420
gtgtgggtgg gcgacaagac cacagccacc gacatcaagg caaggaggt gatggtgctg    480 ggagaggtga acattaacaa cagtgtgttc aaacagtact ctttgagac caagtgccgg    540 gaccccaccc ccgtggacag cgggtgcagg ggcatcgact ccaagcactg gaactcctac    600
tgcaccacca cccacacctt cgtcaaggcg ctgaccatgg acggcaagca ggctgcctgg    660
cggttcatcc ggatcgacac ggcctgcgtg tgcgtgctca gcaggaaggc cgggagacga    720
gcctgacctg cgggccggcc cccacccctcc ccgcgccccc ctccacactc tcctgggc    778

<210> SEQ ID NO 52
<211> LENGTH: 120
<212> TYPE: PRT
<213> ORGANISM: CANINE

<400> SEQUENCE: 52

Ser Ser Ser His Pro Val Phe His Arg Gly Glu Phe Ser Val Cys Asp
1               5                   10                  15

Ser Val Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Thr Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Gly Arg Arg Ala
        115                 120

```
<210> SEQ ID NO 53
<211> LENGTH: 120
<212> TYPE: PRT
<213> ORGANISM: FELINE

<400> SEQUENCE: 53

Ser Ser Ser His Pro Val Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Thr Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Gly Arg Ala
        115                 120

<210> SEQ ID NO 54
<211> LENGTH: 120
<212> TYPE: PRT
<213> ORGANISM: HUMAN

<400> SEQUENCE: 54

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 55
<211> LENGTH: 120
<212> TYPE: PRT
<213> ORGANISM: MURINE

<400> SEQUENCE: 55

Ser Ser Thr His Pro Val Phe His Met Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Thr Val Leu Ala Glu Val Asn Ile Asn Asn Ser Val
        35                  40                  45
```

```
Phe Arg Gln Tyr Phe Phe Glu Thr Lys Cys Arg Ala Ser Asn Pro Val
    50                  55                  60

Glu Ser Gly Cys Arg Gly Ile Asp Ser Lys His Trp Asn Ser Tyr Cys
65                  70                  75                  80

Thr Thr Thr His Thr Phe Val Lys Ala Leu Thr Thr Asp Glu Lys Gln
                85                  90                  95

Ala Ala Trp Arg Phe Ile Arg Ile Asp Thr Ala Cys Val Cys Val Leu
            100                 105                 110

Ser Arg Lys Ala Thr Arg Arg Gly
            115                 120

<210> SEQ ID NO 56
<211> LENGTH: 120
<212> TYPE: PRT
<213> ORGANISM: RAT

<400> SEQUENCE: 56

Ser Ser Thr His Pro Val Phe His Met Gly Glu Phe Ser Val Cys Asp
1               5                   10                  15

Ser Val Ser Val Trp Val Gly Asp Lys Thr Thr Ala Thr Asp Ile Lys
                20                  25                  30

Gly Lys Glu Val Thr Val Leu Gly Glu Val Asn Ile Asn Asn Ser Val
            35                  40                  45

Phe Lys Gln Tyr Phe Phe Glu Thr Lys Cys Arg Ala Pro Asn Pro Val
    50                  55                  60

Glu Ser Gly Cys Arg Gly Ile Asp Ser Lys His Trp Asn Ser Tyr Cys
65                  70                  75                  80

Thr Thr Thr His Thr Phe Val Lys Ala Leu Thr Thr Asp Asp Lys Gln
                85                  90                  95

Ala Ala Trp Arg Phe Ile Arg Ile Asp Thr Ala Cys Val Cys Val Leu
            100                 105                 110

Ser Arg Lys Ala Ala Arg Arg Gly
            115                 120

<210> SEQ ID NO 57
<211> LENGTH: 107
<212> TYPE: PRT
<213> ORGANISM: HUMAN

<400> SEQUENCE: 57

Asp Ile Trp Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
                20                  25                  30

Leu Asn Trp Tyr Gln Gln Lys Pro Asp Gly Thr Val Lys Leu Leu Ile
            35                  40                  45

Thr Thr Ile Ser Arg Gly Phe Ser Gly Val Pro Ser Arg Phe Phe Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Ser Lys Thr Leu Pro Tyr
                85                  90                  95

Thr Phe Gly Gly Gly Thr Lys Leu Glu Ile Lys
            100                 105

<210> SEQ ID NO 58
```

```
<211> LENGTH: 78
<212> TYPE: PRT
<213> ORGANISM: CANINE

<400> SEQUENCE: 58

Asp Ile Val Met Thr Gln Thr Pro Leu Ser Leu Ser Val Ser Pro Gly
1               5                   10                  15

Glu Pro Ala Ser Ile Ser Cys Trp Phe Arg Gln Lys Pro Gly Gln Ser
            20                  25                  30

Pro Gln Arg Leu Ile Thr Gly Asx Pro Ser Arg Phe Gly Ser Gly Ser
        35                  40                  45

Gly Thr Asp Phe Thr Leu Arg Ile Ser Arg Val Glu Ala Asp Asp Ala
50                  55                  60

Gly Val Tyr Cys Phe Gly Gln Gly Thr Lys Leu Glu Ile Lys
65                  70                  75

<210> SEQ ID NO 59
<211> LENGTH: 105
<212> TYPE: PRT
<213> ORGANISM: CANINE

<400> SEQUENCE: 59

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Ile Ser Asn His Leu
            20                  25                  30

Asn Trp Phe Arg Gln Lys Pro Asp Gly Thr Val Lys Leu Leu Ile Tyr
        35                  40                  45

Tyr Ile Ser Arg Phe His Ser Gly Val Pro Ser Arg Phe Gly Ser Gly
    50                  55                  60

Ser Gly Thr Asp Phe Thr Leu Arg Ile Ser Arg Val Glu Ala Asp Asp
65                  70                  75                  80

Ala Gly Val Tyr Tyr Cys Gln Gln Ser Lys Thr Leu Pro Tyr Thr Phe
                85                  90                  95

Gly Gln Gly Thr Lys Leu Glu Ile Lys
            100                 105

<210> SEQ ID NO 60
<211> LENGTH: 107
<212> TYPE: PRT
<213> ORGANISM: CANINE

<400> SEQUENCE: 60

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Asp Ile Ser Asn His
            20                  25                  30

Leu Asn Trp Phe Arg Gln Lys Pro Asp Gly Thr Val Lys Leu Leu Ile
        35                  40                  45

Thr Thr Ile Ser Arg Phe His Ser Gly Val Pro Ser Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Ser Lys Thr Leu Pro Tyr
                85                  90                  95

Thr Phe Gly Gln Gly Thr Lys Leu Glu Ile Lys
            100                 105
```

```
<210> SEQ ID NO 61
<211> LENGTH: 107
<212> TYPE: PRT
<213> ORGANISM: ARTIFICIAL
<220> FEATURE:
<223> OTHER INFORMATION: PROTEIN SEQUENCE FOR GENERATED ANTIBODY

<400> SEQUENCE: 61

Asp Ile Val Met Thr Gln Thr Pro Leu Ser Leu Ser Val Ser Pro Gly
1               5                   10                  15

Glu Pro Ala Ser Ile Ser Cys Arg Ala Ser Gln Asp Ile Ser Asn His
            20                  25                  30

Leu Asn Trp Phe Arg Gln Lys Pro Gly Gln Ser Val Gln Arg Leu Ile
        35                  40                  45

Thr Thr Ile Ser Arg Phe His Ser Gly Val Pro Ser Arg Phe Ser Gly
    50                  55                  60

Ser Gly Ser Gly Thr Asp Phe Thr Leu Arg Ile Ser Arg Val Glu Ala
65                  70                  75                  80

Asp Asp Ala Gly Val Tyr Tyr Cys Gln Gln Ser Lys Thr Leu Pro Tyr
                85                  90                  95

Thr Phe Gly Gln Gly Thr Lys Leu Glu Ile Lys
            100                 105

<210> SEQ ID NO 62
<211> LENGTH: 30
<212> TYPE: PRT
<213> ORGANISM: ARTIFICIAL
<220> FEATURE:
<223> OTHER INFORMATION: PROTEIN SEQUENCE FOR GENERATED ANTIBODY

<400> SEQUENCE: 62

Tyr Ile Ser Arg Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 63
<211> LENGTH: 30
<212> TYPE: PRT
<213> ORGANISM: ARTIFICIAL
<220> FEATURE:
<223> OTHER INFORMATION: PROTEIN SEQUENCE FOR GENERATED ANTIBODY

<400> SEQUENCE: 63

Tyr Ile Ser Arg Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 64
<211> LENGTH: 30
<212> TYPE: PRT
<213> ORGANISM: CANINE

<400> SEQUENCE: 64

Tyr Ile Ser Arg Phe His Ser Leu Ile Gly Tyr Asp Ile Asn Met Ile
1               5                   10                  15

Trp Gly Asp Gly Thr Thr Asp Tyr Asn Ser Asn Leu Lys Ser
            20                  25                  30

<210> SEQ ID NO 65
```

-continued

```
<211> LENGTH: 30
<212> TYPE: PRT
<213> ORGANISM: CANINE

<400> SEQUENCE: 65

Tyr Ile Ser Arg Phe His Ser Leu Ile Gly Tyr Asp Ile Asn Met Ile
1               5                   10                  15

Trp Gly Asp Gly Thr Thr Asp Tyr Asn Ser Asn Leu Lys Ser
            20                  25                  30

<210> SEQ ID NO 66
<211> LENGTH: 8
<212> TYPE: PRT
<213> ORGANISM: CANINE

<400> SEQUENCE: 66

Tyr Ile Ser Arg Phe His Ser Ser
1               5

<210> SEQ ID NO 67
<211> LENGTH: 30
<212> TYPE: PRT
<213> ORGANISM: CANINE

<400> SEQUENCE: 67

Tyr Ile Ser Arg Trp His Ser Leu Ile Gly Tyr Asp Ile Pro Met Ile
1               5                   10                  15

Trp Gly Asp Gly Thr Thr Asp Tyr Asn Ser Ala Leu Lys Ser
            20                  25                  30

<210> SEQ ID NO 68
<211> LENGTH: 30
<212> TYPE: PRT
<213> ORGANISM: CANINE

<400> SEQUENCE: 68

Tyr Val Ser Arg Phe His Ser Leu Ile Gly Tyr Asp Ile Pro Met Ile
1               5                   10                  15

Trp Gly Asp Gly Thr Thr Asp Tyr Asn Ser Ala Leu Trp Ser
            20                  25                  30

<210> SEQ ID NO 69
<211> LENGTH: 30
<212> TYPE: PRT
<213> ORGANISM: CANINE

<400> SEQUENCE: 69

Tyr Val Ser Arg Val His Ser Leu Ile Gly Tyr Asp Ile Asn Met Ile
1               5                   10                  15

Trp Gly Asp Gly Thr Thr Asp Tyr Asn Ser Ala Leu Trp Ser
            20                  25                  30

<210> SEQ ID NO 70
<211> LENGTH: 30
<212> TYPE: PRT
<213> ORGANISM: CANINE

<400> SEQUENCE: 70

Tyr Ile Ser Arg Val His Ser Leu Ile Gly Tyr Asp Ile Asn Met Ile
1               5                   10                  15

Trp Gly Asp Gly Thr Thr Asp Tyr Asn Lys Ala Leu Lys Ser
            20                  25                  30
```

<210> SEQ ID NO 71
<211> LENGTH: 30
<212> TYPE: PRT
<213> ORGANISM: CANINE

<400> SEQUENCE: 71

Tyr Ile Ser Arg Phe His Ser Leu Ile Gly Tyr Asp Ile Tyr Met Ile
1               5                   10                  15

Trp Gly Asp Gly Thr Thr Asp Tyr Asn Ser Ala Leu Lys Ser
            20                  25                  30

<210> SEQ ID NO 72
<211> LENGTH: 30
<212> TYPE: PRT
<213> ORGANISM: CANINE

<400> SEQUENCE: 72

Tyr Ile Ser Arg Phe His Ser Leu Ile Gly Tyr Asp Ile Tyr Met Ile
1               5                   10                  15

Trp Gly Asp Gly Thr Thr Asp Tyr Asn Ser Ala Leu Lys Ser
            20                  25                  30

<210> SEQ ID NO 73
<211> LENGTH: 30
<212> TYPE: PRT
<213> ORGANISM: CANINE
<220> FEATURE:
<221> NAME/KEY: misc_feature
<222> LOCATION: (11)..(11)
<223> OTHER INFORMATION: Xaa can be any naturally occurring amino acid

<400> SEQUENCE: 73

Tyr Ile Arg Arg Phe His Ser Leu Ile Gly Xaa Asp Ile Asn Met Ile
1               5                   10                  15

Trp Gly Asp Gly Thr Thr Asp Lys Asn Ser Ala Leu Lys Ser
            20                  25                  30

<210> SEQ ID NO 74
<211> LENGTH: 30
<212> TYPE: PRT
<213> ORGANISM: CANINE

<400> SEQUENCE: 74

Tyr Ile Ser Gln Phe His Ser Leu Ile Gly Tyr Asp Ile Asn Met Ile
1               5                   10                  15

Trp Gly Asp Ile Thr Thr Asp Tyr Asn Ser Ala Leu Lys Ser
            20                  25                  30

<210> SEQ ID NO 75
<211> LENGTH: 30
<212> TYPE: PRT
<213> ORGANISM: CANINE

<400> SEQUENCE: 75

Tyr Ile Ser Arg Phe His Ser Leu Ile Gly Tyr Asp Ile Tyr Met Ile
1               5                   10                  15

Trp Gly Asp Gly Thr Thr Asp Tyr Asn Ser Ala Leu Lys Ser
            20                  25                  30

<210> SEQ ID NO 76
<211> LENGTH: 7
<212> TYPE: PRT
<213> ORGANISM: CANINE

-continued

<400> SEQUENCE: 76

Tyr Ile Ser Arg Phe His Ser
1               5

<210> SEQ ID NO 77
<211> LENGTH: 30
<212> TYPE: PRT
<213> ORGANISM: CANINE

<400> SEQUENCE: 77

Tyr Asn Ser Arg Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 78
<211> LENGTH: 7
<212> TYPE: PRT
<213> ORGANISM: CANINE

<400> SEQUENCE: 78

Tyr Ile Ser Arg Phe His Ser
1               5

<210> SEQ ID NO 79
<211> LENGTH: 7
<212> TYPE: PRT
<213> ORGANISM: CANINE

<400> SEQUENCE: 79

Tyr Ile Arg Arg Phe His Ser
1               5

<210> SEQ ID NO 80
<211> LENGTH: 7
<212> TYPE: PRT
<213> ORGANISM: CANINE

<400> SEQUENCE: 80

Tyr Ile Ser Arg Phe His Ser
1               5

<210> SEQ ID NO 81
<211> LENGTH: 7
<212> TYPE: PRT
<213> ORGANISM: CANINE

<400> SEQUENCE: 81

Tyr Ile Ser Arg Phe His Ser
1               5

<210> SEQ ID NO 82
<211> LENGTH: 30
<212> TYPE: PRT
<213> ORGANISM: CANINE

<400> SEQUENCE: 82

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30

-continued

```
<210> SEQ ID NO 83
<211> LENGTH: 30
<212> TYPE: PRT
<213> ORGANISM: CANINE

<400> SEQUENCE: 83

Tyr Ile Ser Arg Phe His Ser Leu Ile Gly Tyr Asp Ile Asn Met Ile
1               5                   10                  15

Trp Gly Asp Ile Thr Thr Asp Tyr Asn Ser Ala Leu Lys Ser
            20                  25                  30

<210> SEQ ID NO 84
<211> LENGTH: 30
<212> TYPE: PRT
<213> ORGANISM: CANINE

<400> SEQUENCE: 84

Tyr Ile Ser Arg Phe His Ser Leu Ile Glu Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 85
<211> LENGTH: 30
<212> TYPE: PRT
<213> ORGANISM: CANINE

<400> SEQUENCE: 85

Tyr Ile Ser Arg Phe His Ser Leu Ile Gly Tyr Asp Ile Asn Met Ile
1               5                   10                  15

Trp Gly Asp Gly Thr Thr Asp Gln Asn Ser Ala Leu Lys Ser
            20                  25                  30

<210> SEQ ID NO 86
<211> LENGTH: 30
<212> TYPE: PRT
<213> ORGANISM: CANINE

<400> SEQUENCE: 86

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30

<210> SEQ ID NO 87
<211> LENGTH: 30
<212> TYPE: PRT
<213> ORGANISM: CANINE

<400> SEQUENCE: 87

Tyr Ile Ser Ser Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 88
<211> LENGTH: 30
<212> TYPE: PRT
<213> ORGANISM: CANINE

<400> SEQUENCE: 88

Tyr Ile Ser Ser Phe His Ser Leu Ile Gly Tyr Asp Ile Asn Met Ile
1               5                   10                  15
```

Trp Gly Thr Gly Thr Thr Asp Tyr Asn Ser Ala Leu Lys Ser
            20                  25                  30

<210> SEQ ID NO 89
<211> LENGTH: 30
<212> TYPE: PRT
<213> ORGANISM: CANINE

<400> SEQUENCE: 89

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30

<210> SEQ ID NO 90
<211> LENGTH: 30
<212> TYPE: PRT
<213> ORGANISM: CANINE

<400> SEQUENCE: 90

Tyr Ile Ser Arg Phe His Ser Leu Ile Gly Tyr His Ile Asn Met Ile
1               5                   10                  15

Trp Gly Asp Gly Thr Thr Asp Tyr Asn Ser Ala Leu Lys Ser
            20                  25                  30

<210> SEQ ID NO 91
<211> LENGTH: 30
<212> TYPE: PRT
<213> ORGANISM: CANINE

<400> SEQUENCE: 91

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30

<210> SEQ ID NO 92
<211> LENGTH: 30
<212> TYPE: PRT
<213> ORGANISM: CANINE

<400> SEQUENCE: 92

Tyr Ile Ser Arg Phe His Ser Leu Ile Glu Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 93
<211> LENGTH: 30
<212> TYPE: PRT
<213> ORGANISM: CANINE

<400> SEQUENCE: 93

Tyr Ile Ser Arg Phe His Ser Leu Ile Gly Tyr Asp Ile Asn Met Ile
1               5                   10                  15

Trp Gly Asp Ile Thr Thr Asp Tyr Asn Ser Ala Leu Lys Ser
            20                  25                  30

<210> SEQ ID NO 94
<211> LENGTH: 30
<212> TYPE: PRT
<213> ORGANISM: CANINE

```
<400> SEQUENCE: 94

Tyr Ile Ser Arg Phe His Ser Leu Ile Gly Tyr Asp Ile Asn Met Ile
1               5                   10                  15

Trp Gly Ser Gly Thr Thr Asp Tyr Asn Ser Ala Leu Lys Ser
            20                  25                  30

<210> SEQ ID NO 95
<211> LENGTH: 30
<212> TYPE: PRT
<213> ORGANISM: CANINE

<400> SEQUENCE: 95

Tyr Ile Ser Lys Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 96
<211> LENGTH: 30
<212> TYPE: PRT
<213> ORGANISM: CANINE

<400> SEQUENCE: 96

Tyr Ile Ser Arg Phe His Ser Leu Ile Gly Tyr Asp Ile Asn Met Ile
1               5                   10                  15

Trp Gly Asp Gly Thr Thr Asp Tyr Asn Ser Ala Ile Lys Ser
            20                  25                  30

<210> SEQ ID NO 97
<211> LENGTH: 30
<212> TYPE: PRT
<213> ORGANISM: CANINE

<400> SEQUENCE: 97

Tyr Ile Ser Ser Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 98
<211> LENGTH: 30
<212> TYPE: PRT
<213> ORGANISM: CANINE

<400> SEQUENCE: 98

Tyr Ile Ser Arg Phe His Ser Leu Ile Gly Tyr Asp Gln Asn Met Ile
1               5                   10                  15

Trp Gly Asp Gly Thr Thr Asp Tyr Asn Ser Ala Leu Lys Ser
            20                  25                  30

<210> SEQ ID NO 99
<211> LENGTH: 30
<212> TYPE: PRT
<213> ORGANISM: CANINE

<400> SEQUENCE: 99

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30
```

```
<210> SEQ ID NO 100
<211> LENGTH: 30
<212> TYPE: PRT
<213> ORGANISM: CANINE

<400> SEQUENCE: 100

Tyr Ile Arg Arg Phe His Ser Leu Ile Gly Tyr Asp Ile Asn Met Ile
1               5                   10                  15

Trp Gly Asp Gly Thr Thr Asp Tyr Asn Ser Ala Leu Lys Ser
            20                  25                  30

<210> SEQ ID NO 101
<211> LENGTH: 30
<212> TYPE: PRT
<213> ORGANISM: CANINE

<400> SEQUENCE: 101

Tyr Ile Ser Arg Phe His Ser Leu Ile Gly Tyr Asp Ile Asn Met Ile
1               5                   10                  15

Trp Gly Thr Gly Thr Thr Asp Tyr Asn Ser Ala Leu Lys Ser
            20                  25                  30

<210> SEQ ID NO 102
<211> LENGTH: 23
<212> TYPE: PRT
<213> ORGANISM: CANINE

<400> SEQUENCE: 102

Leu Ile Gly Tyr Asp Ile Asn Met Ile Trp Gly Asp Gly Thr Thr Asp
1               5                   10                  15

Tyr Asn Ser Ala Leu Lys Ser
            20

<210> SEQ ID NO 103
<211> LENGTH: 30
<212> TYPE: PRT
<213> ORGANISM: CANINE

<400> SEQUENCE: 103

Tyr Ile Ser Arg Phe His Ser Leu Ile Gly Tyr Asp Gln Asn Met Ile
1               5                   10                  15

Trp Gly Asp Gly Thr Thr Asp Tyr Asn Ser Ala Leu Lys Ser
            20                  25                  30
```

CANINIZED ANTI-NGF ANTIBODIES AND METHODS THEREOF

CROSS REFERENCE TO RELATED APPLICATIONS

This application claims priority from U.S. Provisional Application No. 61/656,056 filed Jun. 6, 2012 which is incorporated by reference in its entirety.

FIELD OF THE INVENTION

The present invention relates to the field of immunology. More specifically, the present invention relates to anti-NGF antigen binding proteins or antibodies that have been modified to become non-immunogenic in canines, particularly chimeric antibodies and caninized antibodies that specifically bind to canine NGF. The invention further concerns use of such antigen binding proteins or antibodies in the treatment and/or prevention of NGF related disorders, particularly pain, in canines.

BACKGROUND OF THE INVENTION

Nerve growth factor (NGF) was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne, et al., *Nature* 368:246-249 (1994) and Crowley, et al., *Cell* 76: 1001-101 I (1994)). NGF upregulates expression of neuropeptides in sensory neurons (Lindsay, et al, *Nature* 337:362-364 (1989)), and its activity is mediated through two different membrane-bound receptors, the TrkA tyrosine kinase receptor and the p75 common neurotrophin receptor (sometimes termed "high affinity" and "low affinity" NGF receptors, respectively) which is structurally related to other members of the tumor necrosis factor receptor family (Chao, et al., *Science* 232: 518-521 (1986)).

In addition to its effects in the nervous system, NGF has been increasingly implicated in processes outside of the nervous system. For example, NGF has been shown to enhance vascular permeability (Otten, et al., *Eur J Pharmacol.* 106: 199-201 (1984)), enhance T- and B-cell immune responses (Otten, et al., *Proc. Natl. Acad. Sci. USA* 86:10059-10063 (1989)), induce lymphocyte differentiation and mast cell proliferation and cause the release of soluble biological signals from mast cells (Matsuda, et al., *Proc. Natl. Acad. Sci. USA* 85:6508-6512 (1988); Pearce, et al., *J. Physiol.* 372:379-393 (1986); Bischoff, et al., *Blood* 79:2662-2669 (1992); Horigome, et al., *J. Bioi. Chem.* 268:14881-14887 (1993)).

NGF is produced by a number of cell types including mast cells (Leon, et al., *Proc. Natl. Acad. Sci. USA* 91:3739-3743 (1994)), B-lymphocytes (Torcia, et al., *Cell* 85:345-356 (1996), keratinocytes (Di Marco, et al., J. Biol. Chem. 268: 22838-22846)), smooth muscle cells (Ueyama, et al., *J. Hypertens.* 11: 1061-1065 (1993)), fibroblasts (Lindholm, et al., *Eur. J. Neurosci.* 2:795-801 (1990)), bronchial epithelial cells (Kassel, et al., *Clin, Exp. Allergy* 31:1432-40 (2001)), renal mesangial cells (Steiner, et al., *Am. J. Physiol.* 261: F792-798 (1991)) and skeletal muscle myotubes (Schwartz, et al., *J Photochem. Photobiol.* B66: 195-200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., *Neuroreport* 4:563-565 (1993)), multiple sclerosis (BracciLaudiero, et al, Neurosci. Lett. 147:9-12 (1992)), psoriasis (Raychaudhuri, et al., *Acta Dern. l'enereol.* 78:84-86 (1998)), arthritis (Falcim, et al., *Ann. Rheum. Dis.* 55:745-748 (1996)), interstitial cystitis (Okragly, et al., *J. Urology* 161: 438-441 (1999)) and asthma (Braun, et al., *Eur. J Immunol.* 28:3240-3251 (1998)).

Consistently, an elevated level of NGF in peripheral tissues is associated with hyperalgesia and inflammation and has been observed in a number of forms of arthritis. The synovium of patients affected by rheumatoid arthritis expresses high levels of NGF while in non-inflamed synovium NGF has been reported to be undetectable (Aloe, et al., *Arch. Rheum.* 35:351-355 (1992)). Similar results were seen in rats with experimentally induced rheumatoid arthritis (Aloe, et al., *Clin. Exp. Rheumatol.* 10:203-204 (1992)). Elevated levels of NGF have been reported in transgenic arthritic mice along with an increase in the number of mast cells (Aloe, et al., *Int. J. Tissue Reactions-Exp. Clin. Aspects* 15:139-143 (1993)).

Osteoarthritis (OA) is one of the most common chronic musculoskeletal diseases in dogs, affecting 20% of the canine population over one year of age. The development of OA is mainly secondary to trauma, joint instability, and diseases such as hip dysplasia. Osteoarthritis is a disease condition of the entire joint, and both inflammatory and degenerative changes of all articular structures result in disability and clinical signs of lameness and pain. Pain is the most important clinical manifestation of canine OA and it is the result of a complex interplay between structural joint changes, biochemical and molecular alterations, as well as peripheral and central pain-processing mechanisms. Within this network, the activation and sensitization of peripheral nociceptors by inflammatory and hyperalgesic mediators (e.g. cytokines, prostaglandins and neuromediators) is one of the main peripheral mechanisms responsible for the joint pain. Nerve growth factor (NGF) is one of the neuromediators that has received broader attention as a key regulator involved in both inflammatory and neuropathic pain. (Isola et al. Vet Comp Orthop Traumatol 4: 2011 pgs 279-284)

SUMMARY OF THE INVENTION

The invention provides a novel caninized anti-NGF antigen binding protein (such as caninized anti-NGF antagonist antibodies), and polynucleotides encoding the same. The invention further provides use of said antigen binding proteins and/or nucleotides in the treatment and/or prevention of NGF related disorders, particularly pain.

In one embodiment the present invention provides an isolated antigen binding protein or antibody fragment that specifically binds to canine NGF. In some embodiments the antigen binding protein is selected from the group consisting of: a monoclonal antibody, a chimeric antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')$_2$ fragment, an Fv fragment, an ScFv fragment, an Fd fragment, a single domain antibody, a dAb fragment, a small modular immunopharmaceutical (SMIP) a nanobody, and IgNAR molecule. In some embodiments said antibody is a monoclonal antibody. In some embodiments said antibody is chimeric. In one or more embodiments the antigen binding protein of the invention is caninized. In one or more embodiments the antigen binding protein of the invention is a canine antibody.

In one or more embodiments the antigen binding protein that specifically binds to canine NGF prevents canine NGF from binding to canine TrkA and to a lesser extent p75 thus inhibiting signaling through canine TrkA and p75, which has been shown to reduce the signaling through sensory neurons thus reducing levels of pain. In one or more embodiments, the antigen binding protein of the invention has no significant adverse effect on the immune system of a canine.

In one or more embodiments the isolated antigen binding protein that specifically binds to canine NGF treats an NGF related disorder in a canine. In some embodiments the NGF related disorder in a canine and is selected from the group consisting of: cardiovascular diseases, atherosclerosis, obesity, diabetes, metabolic syndrome, pain and inflammation. In some embodiments the NGF related disorder is pain. In some embodiments the type of pain is selected from the group consisting of: chronic pain; inflammatory pain, postoperative incision pain, neuropathic pain, fracture pain, osteoporotic fracture pain, post-herpetic neuralgia, cancer pain, pain resulting from burns, pain associated with wounds, pain associated with trauma, neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders and peripheral neuropathy. In some embodiments the type of pain is chronic pain. In some embodiments, the type of pain is osteoarthritis pain.

In one or more embodiments, the present invention provides an isolated antigen binding protein and comprising at least one selected from the group consisting of:

a variable heavy chain (VH) comprising a complementary determining region (CDR 1) having the amino acid sequence LIGYDIN (SEQ ID NO.1); LIQYDIN (SEQ ID NO. 7) or LIEYDIN (SEQ ID NO. 8);

a variable heavy chain (VH) comprising a complementary determining region (CDR2) having the amino acid sequence MIWGDGTTDYNSALKS (SEQ ID NO.2); or MIWGTGTTDYNSALKS (SEQ ID NO.13);

a variable heavy chain (VH) comprising a complementary determining region (CDR3) having the amino acid sequence GGYYYGTSYYFDY (SEQ ID NO.3); or GGYWYATSYYFDY (SEQ ID NO. 9); and a variant thereof having one or more conservative amino acid substitutions in at least one of CDR1, CDR2 or CDR3.

In one or more embodiments, the present invention provides an isolated antigen binding protein comprising at least one selected from the group consisting of:

a variable heavy chain (VL) comprising a complementary determining region (CDR 1) having the amino acids sequence RASQDISNHLN (SEQ ID NO. 4); or RASQSISNNLN (SEQ ID NO. 10);

a variable heavy chain (VL) comprising a complementary determining region (CDR 2) having the amino acids sequence YISRFHS (SEQ ID NO. 5) or YISSFHS (SEQ ID NO. 11);

a variable heavy chain (VL) comprising a complementary determining region (CDR 3) having the amino acids sequence QQSKTLPYT (SEQ ID NO.6) or QQSHTLPYT (SEQ ID NO. 12); and a variant thereof having one or more conservative amino acid substitutions in at least one of CDR1, CDR2 or CDR3. In some embodiments the present invention provides a isolated antigen binding protein having at least one of the variable light chain CDRs described above, and can further include at least one of the following variable heavy chain CDRs selected from the group consisting of:

a variable heavy chain (VH) comprising a complementary determining region (CDR 1) having the amino acid sequence LIGYDIN (SEQ ID NO.1); LIQYDIN (SEQ ID NO. 7) or LIEYDIN (SEQ ID NO. 8);

a variable heavy chain (VH) comprising a complementary determining region (CDR2) having the amino acid sequence MIWGDGTTDYNSALKS (SEQ ID NO.2); or MIWGTGTTDYNSALKS (SEQ ID NO.13);

a variable heavy chain (VH) comprising a complementary determining region (CDR3) having the amino acid sequence GGYYYGTSYYFDY (SEQ ID NO.3); or GGYWYATSYYFDY (SEQ ID NO. 9); and a variant thereof having one or more conservative amino acid substitutions in at least one of CDR1, CDR2 or CDR3.

In one or more embodiments, the antigen binding protein of the present invention may include at least one of the following:

a variable heavy chain comprising:

QVQLKESGPGLVAPSQSLSITCTVSGFSLIGYDINWVRQPPGKGLEWLGM

IWGDGTTDYNSALKSRLSISKDNSKSQVFLKMNSLRTDDTATYSCARGGY

YYGTSYYFDYWGQGTTLTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRD (SEQ ID NO. 14;

MU-RN911-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

YYGTSYYFDYWGQGTLVTVSS (SEQ ID NO: 17;

CAN-N2G9-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 25;

CAN-LTM109-VH);

EVQLVESGGDLARPGGSLKLSCVVSGFSLIQYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 27;

CAN-SSM57-VH);

EVQLVESGGDLARPGGSLKLSCVVSGFSLIEYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 28;

CAN-SSM58-VH);

EVQLVESGGDLARPGGSLKLSCVVSGFSLIEYDINWVRQAPGKGLQWVTM

IWGTGTTDYNSALKSRFTVSRDNAMNTVYLQMNSLRVEDTAVYYCARGGY

WYATSYYFDYWGQGTLVTVSS (SEQ ID NO: 29;

CAN-SSM66-VH);

and variants thereof having one or more conservative amino acid substitutions.

In one or more embodiments, the isolated antigen binding protein of the invention may include at least one of the following:
a variable light chain comprising:

DIQMTQTTSSLSASLGDRVTISCRASQDISNHLNWYQQKPDGTVKLLIYY
ISRFHSGVPSRFSGSGSGTDYSLTISNLEQEDIATYFCQQSKTLPYTFGG
GTKLEIKRA (SEQ ID NO. 15; MU-RN911-VL);

DIVMTQTPLSLSVSPGETASISCRASQDISNHLNWFRQKPGQSPQRLIYY
ISRFHSGVPDRFSGGSGTDFTLRISRVEADDTGVYYCQQSKTLPYTFGAG
TKLEIK (SEQ ID NO. 16; CAN-E3M-VL));

DIVMTQTPLSLSVSPGEPASISCRASQDISNHLNWFRQKPGQSPQRLIYY
ISRFHSGVPSRFSGSGSGTDFTLRISRVEADDAGVYYCQQSKTLPYTFGQ
GTKLEIK (SEQ ID NO. 18; CAN-618-VL));

DIVMTQTPLSLSVSPGEPASISCRASQDISNHLNWFRQKPDGTVKLLIYY
ISRFHSGVPSRFSGSGSGTDFTLRISRVEADDAGVYYCQQSKTLPYTFGQ
GTKLEIK (SEQ ID NO. 19; CAN-QC23-VL));

DIVMTQTPLSLSVSPGEPASISCRASQDISNHLNWYQQKPDGTVKLLIYY
ISRFHSGVPSRFSGSGSGTDYSLTISNLEQEDIATYFCQQSKTLPYTFGG
GTKLEI (SEQ ID NO. 20; CAN-618FW1-VL);

DIQMTQTTSSLSASLGDRVTISCRASQDISNHLNWFRQKPGQSPQRLIYY
ISRFHSGVPSRFSGSGSGTDYSLTISNLEQEDIATYFCQQSKTLPYTFGG
GTKLEI (SEQ ID NO. 21; CAN-618FW2-VL);

DIQMTQTTSSLSASLGDRVTISCRASQDISNHLNWYQQKPDGTVKLLIYY
ISRFHSGVPSRFSGSGSGTDFTLRISRVEADDAGVYYCQQSKTLPYTFGQ
GTKLEI (SEQ ID NO. 22; CAN-618FW3-VL);

DIQMTQTTSSLSASLGDRVTISCRASQDISNHLNWYQQKPDGTVKLLIYY
ISRFHSGVPSRFSGSGSGTDYSLTISNLEQEDIATYFCQQSKTLPYTFGQ
GTKLEI (SEQ ID NO. 23; CAN-618FW4-VL);

DIVMTQTPLSLSVSPGETASISCRASQSISNNLNWFRQKPGQSPQRLIYY
ISRFHSGVPDRFSGSGSGTDFTLRISRVEADDTGVYYCQQSHTLPYTFGA
GTKLEIK (SEQ ID NO. 24; CAN-LTM109-VL);

DIVMTQTPLSLSVSPGETASISCRASQSISNNLNWFRQKPGQSPQRLIYY
ISSFHSGVPDRFSGSGSGTDFTLRISRVEADDTGVYYCQQSHTLPYTFGA
GTKLEIK (SEQ ID NO. 26; CAN-SSME3M-VL);

DIVMTQTPLSLSVSPGEPASISCRASQSISNNLNWFRQKPDGTVKLLIYY
ISSFHSGVPSRFSGSGSGTDFTLRISRVEADDAGVYYCQQSHTLPYTFGQ
GTKLEIK (SEQ ID NO. 30; CAN-SSMQC23-VL); , and
variants thereof having one or more conservative amino acid substitutions. In some embodiments the present invention provides an isolated antigen binding protein having at least one of the variable light chain described above, and can further include at least one of the following variable heavy chain of the isolated antibody or antigen binding portion thereof selected from the group consisting of:

QVQLKESGPGLVAPSQSLSITCTVSGFSLIGYDINWVRQPPGKGLEWLGM

IWGDGTTDYNSALKSRLSISKDNSKSQVFLKMNSLRTDDTATYSCARGGY

YYGTSYYFDYWGQGTTLTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRD (SEQ ID NO. 14;

MU-RN911-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

YYGTSYYFDYWGQGTLVTVSS (SEQ ID NO: 17;

CAN-N2G9-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 25;

CAN-LTM109-VH);

EVQLVESGGDLARPGGSLKLSCVVSGFSLIQYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 27;

CAN-SSM57-VH);

EVQLVESGGDLARPGGSLKLSCVVSGFSLIEYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 28;

CAN-SSM58-VH);

EVQLVESGGDLARPGGSLKLSCVVSGFSLIEYDINWVRQAPGKGLQWVTM

IWGTGTTDYNSALKSRFTVSRDNAMNTVYLQMNSLRVEDTAVYYCARGGY

WYATSYYFDYWGQGTLVTVSS (SEQ ID NO: 29;

CAN-SSM66-VH);

and variants thereof having one or more conservative amino acid substitutions.

In one or more embodiments, the isolated antigen binding protein of the invention can include at least one of the following:
a) a variable light chain comprising:

DIQMTQTTSSLSASLGDRVTISCRASQDISNHLNWYQQKPDGTVKLLIYY
ISRFHSGVPSRFSGSGSGTDYSLTISNLEQEDIATYFCQQSKTLPYTFGG
GTKLEIKRA (SEQ ID NO. 15; MU-RN911-VL);

DIVMTQTPLSLSVSPGETASISCRASQDISNHLNWFRQKPGQSPQRLIYY
ISRFHSGVPDRFSGGSGTDFTLRISRVEADDTGVYYCQQSKTLPYTFGAG
TKLEIK (SEQ ID NO. 16; CAN-E3M-VL));

DIVMTQTPLSLSVSPGEPASISCRASQDISNHLNWFRQKPGQSPQRLIYY
ISRFHSGVPSRFSGSGSGTDFTLRISRVEADDAGVYYCQQSKTLPYTFGQ
GTKLEIK (SEQ ID NO. 18; CAN-618-VL));

DIVMTQTPLSLSVSPGEPASISCRASQDISNHLNWFRQKPDGTVKLLIYY
ISRFHSGVPSRFSGSGSGTDFTLRISRVEADDAGVYYCQQSKTLPYTFGQ
GTKLEIK (SEQ ID NO. 19; CAN-QC23-VL));

DIVMTQTPLSLSVSPGEPASISCRASQDISNHLNWYQQKPDGTVKLLIYY
ISRFHSGVPSRFSGSGSGTDYSLTISNLEQEDIATYFCQQSKTLPYTFGG
GTKLEI (SEQ ID NO. 20; CAN-618FW1-VL);

DIQMTQTTSSLSASLGDRVTISCRASQDISNHLNWFRQKPGQSPQRLIYY
ISRFHSGVPSRFSGSGSGTDYSLTISNLEQEDIATYFCQQSKTLPYTFGG
GTKLEI (SEQ ID NO. 21; CAN-618FW2-VL);

DIQMTQTTSSLSASLGDRVTISCRASQDISNHLNWYQQKPDGTVKLLIYY
ISRFHSGVPSRFSGSGSGTDFTLRISRVEADDAGVYYCQQSKTLPYTFGQ
GTKLEI (SEQ ID NO. 22; CAN-618FW3-VL);

DIQMTQTTSSLSASLGDRVTISCRASQDISNHLNWYQQKPDGTVKLLIYY
ISRFHSGVPSRFSGSGSGTDYSLTISNLEQEDIATYFCQQSKTLPYTFGQ
GTKLEI (SEQ ID NO. 23; CAN-618FW4-VL);

DIVMTQTPLSLSVSPGETASISCRASQSISNNLNWFRQKPGQSPQRLIYY
ISRFHSGVPDRFSGSGSGTDFTLRISRVEADDTGVYYCQQSHTLPYTFGA
GTKLEIK (SEQ ID NO. 24; CAN-LTM109-VL);

-continued

```
DIVMTQTPLSLSVSPGETASISCRASQSISNNLNWFRQKPGQSPQRLIYY
ISSFHSGVPDRFSGSGSGTDFTLRISRVEADDTGVYYCQQSHTLPYTFGA
GTKLEIK (SEQ ID NO. 26; CAN-SSME3M-VL);

DIVMTQTPLSLSVSPGEPASISCRASQSISNNLNWFRQKPDGTVKLLIYY
ISSFHSGVPSRFSGSGSGTDFTLRISRVEADDAGVYYCQQSHTLPYTFGQ
GTKLEIK (SEQ ID NO. 30; CAN-SSMQC23-VL); ,
``` and variants thereof having one or more conservative amino acid substitutions; and b) a variable heavy chain comprising:

```
QVQLKESGPGLVAPSQSLSITCTVSGFSLIGYDINWVRQPPGKGLEWLGM

IWGDGTTDYNSALKSRLSISKDNSKSQVFLKMNSLRTDDTATYSCARGGY

YYGTSYYFDYWGQGTTLTVSSAKTTPPSVYPLAPGSAAQTNSMVTLGCLV

KGYFPEPVTVTWNSGSLSSGVHTFPAVLQSDLYTLSSSVTVPSSTWPSET

VTCNVAHPASSTKVDKKIVPRD (SEQ ID NO. 14;

MU-RN911-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

YYGTSYYFDYWGQGTLVTVSS (SEQ ID NO: 17;

CAN-N2G9-VH);

EVQLVESGGDLARPGGSLKLSCVVSGFSLIGYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 25;

CAN-LTM109-VH);

EVQLVESGGDLARPGGSLKLSCVVSGFSLIQYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 27;

CAN-SSM57-VH);

EVQLVESGGDLARPGGSLKLSCVVSGFSLIEYDINWVRQAPGKGLQWVTM

IWGDGTTDYNSALKSRFTVSRDNAMNTVYLQMNSLRVEDTAVYYCARGGY

WYATSYYFDYWGQGTLVTVSS (SEQ ID NO: 28;

CAN-SSM58-VH);

EVQLVESGGDLARPGGSLKLSCVVSGFSLIEYDINWVRQAPGKGLQWVTM

IWGTGTTDYNSALKSRFTVSRDNAMNTVYLQMNSLRVEDTAVYYCARGGY

WYATSYYFDYWGQGTLVTVSS (SEQ ID NO: 29;

CAN-SSM66-VH);
``` and variants thereof having one or more conservative amino acid substitutions.

In one or more embodiments, the present invention provides an isolated antigen binding protein wherein the variable light chain comprises SEQ ID NO. 16 (CAN-E3M-VL) and the variable heavy chain comprises SEQ ID NO. 17 (CAN-N2G9-VH).

In one or more embodiments, the present invention provides an isolated antigen binding protein comprising a variable light chain comprising SEQ ID NO. 26 (CAN-SSME3M-VL) and the variable heavy chain comprising SEQ ID NO. 27 (CAN-SSM57-VH).

In one or more embodiments, the present invention provides an isolated antigen binding protein comprising a variable light chain comprising SEQ ID NO. 30 (CAN-SSMQC23-VL) and a variable heavy chain comprising SEQ ID NO. 27 (CAN-SSM57-VH).

In one or more embodiments, the present invention provides a veterinary composition comprising a therapeutically effective amount of any one or more of the isolated antigen binding proteins of the present invention.

In one or more embodiment the veterinary composition of the invention has no significant adverse effect on the immune system of a canine.

In one or more embodiments, the present invention provides a host cell that produces any one or more of the antigen binding proteins of the present invention.

In one embodiment, the invention provides an isolated nucleic acid that comprises a nucleic acid sequence encoding a caninized antigen binding protein selected from the group consisting of:

nucleic acids encoding a variable heavy chain (VH) selected from the group consisting of: SEQ ID NO. 32 (MU-RN911-VHnt); SEQ ID NO: 34 (CAN-N2G9-VHnt); SEQ ID NO: 38 (CAN-LTM109-VHnt); SEQ ID NO: 40 (CAN-SSM57-VHnt); SEQ ID NO: 41 (CAN-SSM58-VHnt); SEQ ID NO: 42 (CAN-SSM66-VHnt); and variants thereof having one or more conservative nucleic acid substitutions.

In one or more embodiments, the invention provides an isolated nucleic acid that comprises a nucleic acid sequence encoding a caninized antigen binding protein selected from the group consisting of:

nucleic acids encoding a variable light chain (VL) selected from the group consisting of: SEQ ID NO. 31 (MU-RN911-VLnt); SEQ ID NO: 33 (CAN-E3M-VLnt); SEQ ID NO: 35 (CAN-618-VLnt); SEQ ID NO: 36 (CAN-QC23-VLnt); SEQ ID NO: 37 (CAN-LTM109-VLnt); SEQ ID NO: 39 (CAN-SSME3M-VLnt); SEQ ID NO: 43 (CAN-SSMQC23-VLnt); and variants thereof having one or more conservative nucleic acid substitutions.

In some embodiments the invention further comprises nucleic acids encoding a variable heavy chain (VH) selected from the group consisting of: SEQ ID NO. 32 (MU-RN911-VHnt); SEQ ID NO: 34 (CAN-N2G9-VHnt); SEQ ID NO: 38 (CAN-LTM109-VHnt); SEQ ID NO: 40 (CAN-SSM57-VHnt); SEQ ID NO: 41 (CAN-SSM58-VHnt); or SEQ ID NO: 42 (CAN-SSM66-VHnt); and variants thereof having one or more conservative nucleic acid substitutions.

In one or more embodiments, the present invention provides isolated nucleic acid wherein the nucleic acid encodes the variable light chain of a caninized anti-NGF antigen binding protein which comprises SEQ ID NO. 33 (CAN-E3M-VLnt) and the nucleic acid encoding the variable heavy chain which comprises SEQ ID NO. 34 (CAN-N2G9-VHnt).

In one or more embodiments, the present invention provides isolated nucleic acid wherein the nucleic acid encodes the variable light chain which comprises SEQ ID NO: 39 (CAN-SSME3M-VLnt) and the nucleic acid encoding the variable heavy chain which comprises SEQ ID NO: 40 (CAN-SSM57-VHnt).

In one or more embodiments, the present invention provides isolated nucleic acid wherein the nucleic acid encodes the variable light chain which comprises SEQ ID SEQ ID NO: 43 (CAN-SSMQC23-VLnt) and the nucleic acid encoding the variable heavy chain which comprises SEQ ID NO: 40 (CAN-SSM57-VHnt).

In one or more embodiments, the invention provides a vector comprising the any one or more of the nucleic acids of the present invention.

In one or more embodiments, the invention provides a host cell comprising the any one or more of the nucleic acids of the present invention.

In one or more embodiments, the invention provides a host cell comprising the vector that comprises any one or more of the nucleic acids of the present invention.

In one embodiment, the invention provides a method of producing an antigen binding protein comprising culturing any of the host cells of the present invention as described herein, under conditions that result in production of the caninized antigen binding protein, and isolating the caninized antibody antigen binding protein from the host cell or culture medium of the host cell.

In one embodiment, the present invention provides a method of treating a canine for an NGF related disorder comprising administering a therapeutically effective amount of the veterinary composition of the invention. In some embodiments, the NGF related disorder is selected from the group consisting of: cardiovascular diseases, atherosclerosis, obesity, diabetes, metabolic syndrome, pain and inflammation. In some embodiments of the present invention the type of pain is selected from the group consisting of: chronic pain; inflammatory pain, post-operative incision pain, neuropathic pain, fracture pain, osteoporotic fracture pain, post-herpetic neuralgia, cancer pain, pain resulting from burns, pain associated with wounds, pain associated with trauma, neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders and peripheral neuropathy. In some embodiments, the type of pain is osteoarthritis pain.

In one or more embodiments, the present invention provides a method of inhibiting NGF activity in a canine by administering the veterinary composition of the present invention.

In one embodiment, the present invention provides a method of detecting or quantitating NGF levels in a biological sample, the method comprising:
(a) incubating a clinical or biological sample containing NGF in the presence of any one of the caninized antibody, antigen binding protein or fragments of the present invention; and
(b) detecting the antigen binding protein or fragments which are bound to NGF in the sample.

In some embodiments the antigen binding protein or fragments is detectably labeled. In some embodiments the antigen binding protein or fragments is unlabelled is used in combination with a second antigen binding protein or fragments which is detectably labeled. In one embodiment the invention comprises a kit comprising the antigen binding protein of the invention.

BRIEF DESCRIPTION OF THE FIGURES

FIG. 6. (A) Molecular modeling of the RN 911 epitope on mature human B-NGF. NGF typically is homodimerized. Each monomer of NGF is differentiated by the light and medium grey designations, and residues identified that affect RN911 binding are shown in black. Each of the variable regions that impact binding of the various murine mAbs is labeled accordingly. (B) Amino acid sequence conservation across species of the RN911 binding epitope on B-NGF. Amino acids critical for RN911 binding to NGF are shaded in gray. SEQ ID NOs 52-54 describing the amino acid sequences of dog, cat, human, mouse and rat NGF are noted.

FIG. 7 is a graphical representation of serum levels of free RN911 after IV administration to beagle dogs.

FIG. 8 is a graphical representation of serum levels of "bound NGF" (i.e., NGF bound to RN911) after IV administration to beagle dogs.

FIG. 9: is a graphical representation of the effect of RN911 (3 mg/kg, IV) on lameness in a beagle (LPS-induced) synovitis pain model. *$P<0.1$ as compared with PBS vehicle.

FIG. 10 is a schematic representation of an example of framework substitutions made to light chains to regain expression and retain binding. SEQ ID NOs 57-61 describing the sequences are noted FIG. 11 summarizes the results of the expression and the mutations of the caninized derivatives using different framework sequences.

FIGS. 12A and B is a graphical representation of affinity data of caninized mAb (left). (Right) trkA inhibition data with pre-incubated mAb+NGF. (Bottom)

FIG. 13 is a graphical representation of affinity data of the caninized mAb determined by cell-based assay using trkA expressing cell line to determine EC50 of each mAb.

FIG. 14 is a graphical representation of the effects of caninized Anti-NGF mAb PF 06442590 (CANSSM57-VH/CAN SSME3M-VL)

FIG. 15 is an illustration of the library design used for Look-Through-Mutagenesis (LTM) and Site-saturation mutagenesis (SSM)

FIG. 16 is a graphical representation of a pharmacokinetics (PK) study of anti-NGF monoclonal antibodies in dogs as measured for thirty-five days.

FIG. 17 is a schematic depiction of inflammation induction by intra-articular injection of MIA used to reproduce OA-like lesions in rat (MIA rat pain model).

FIGS. 18 and 19 is a graphical representation of results after pain treatment (morphine, monoclonal antibodies) in the MIA rat pain model

BRIEF DESCRIPTION OF THE SEQUENCES

SEQ ID NO: 1 is the amino acid sequence for the variable heavy chain CDR1 referred to herein as RN911-VH-CDR1

SEQ ID NO: 2 is the amino acid sequence for the variable heavy chain CDR2 referred to herein as RN911-VH-CDR2

SEQ ID NO: 3 is the amino acid sequence for the variable heavy chain CDR2 referred to herein as RN911-VH-CDR3

SEQ ID NO: 4 is the amino acid sequence for the variable light chain CDR 1 referred to herein as RN911-VL-CDR1

SEQ ID NO: 5 is the amino acid sequence for the variable light chain CDR2 referred to herein as RN911-VL-CDR2

SEQ ID NO: 6 is the amino acid sequence for the variable light chain CDR3 referred to herein as RN911-VL-CDR3

SEQ ID NO: 7 is the amino acid sequence for the variable heavy chain CDR1 referred to herein as SSM57-VH-CDR1

Figure 1:
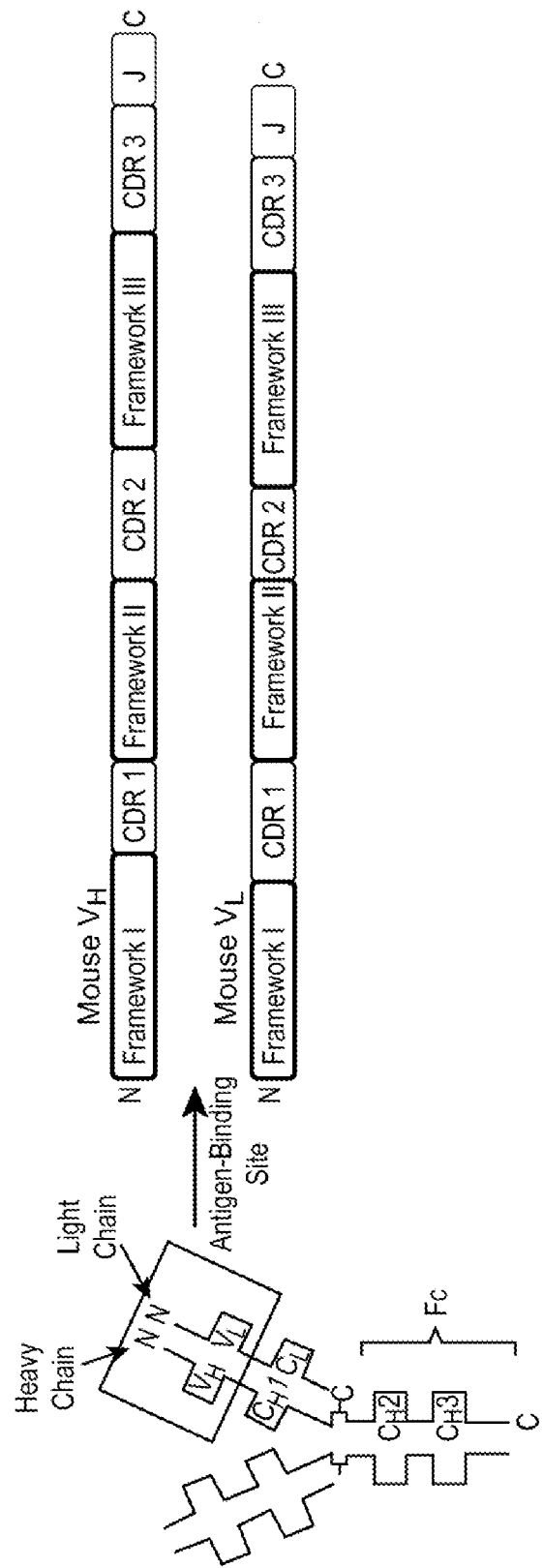
FIG. 1: is a schematic representation of the general structure of a mouse immunoglobulin G (IgG) molecule highlighting the antigen binding site.

SEQ ID NO: 8 is the amino acid sequence for the variable heavy chain CDR1 referred to herein as SSM58-VH-CDR1

SEQ ID NO: 9 is the amino acid sequence for the variable heavy chain CDR3 referred to herein as LTM109-VH-CDR3 and SSM57-VH CDR3

SEQ ID NO: 10 is the amino acid sequence for the variable light chain CDR1 referred to herein as LTM109-VL-CDR1

SEQ ID NO: 11 is the amino acid sequence for the variable light chain CDR2 referred to herein as SSM57-VL-CDR2

SEQ ID NO: 12 is the amino acid sequence for the variable light chain CDR3 referred to herein as LTM109-VL-CDR3

SEQ ID NO: 13 is the amino acid sequence for the variable light chain CDR2 referred to herein as SSM66-VH-CDR2 and SSM57-VH CDR2

SEQ ID NO: 14 is the amino acid sequence for the variable heavy chain referred to herein as MU-RN911-VH SEQ ID NO: 15 is the amino acid sequence for the variable light chain referred to herein as MU-RN911-VL SEQ ID NO: 16 is the amino acid sequence for the variable heavy chain referred to herein as CAN-E3M-VL SEQ ID NO: 17 is the amino acid sequence for the variable heavy chain referred to herein as CAN-N2G9-VH SEQ ID NO: 18 is the amino acid sequence for the variable light chain referred to herein as CAN-618-VL SEQ ID NO: 19 is the amino acid sequence for the variable light chain referred to herein as CAN-QC23-VL SEQ ID NO: 20 is the amino acid sequence for the variable light chain referred to herein as CAN-618FW1-VL SEQ ID NO: 21 is the amino acid sequence for the variable light chain referred to herein as CAN-618FW2-VL SEQ ID NO: 22 is the amino acid sequence for the variable light chain referred to herein as CAN-618FW3-VL SEQ ID NO: 23 is the amino acid sequence for the variable light chain referred to herein as CAN-618FW4-VL SEQ ID NO: 24 is the amino acid sequence for the variable light chain referred to herein as CAN-LTM109-VL SEQ ID NO: 25 is the amino acid sequence for the variable heavy chain referred to herein as CAN-LTM109-VH)

SEQ ID NO: 26 is the amino acid sequence for the variable light chain referred to herein as CAN-SSME3M-VL)

SEQ ID NO: 27 is the amino acid sequence for the variable heavy chain referred to herein as CAN-SSM57-VH SEQ ID NO: 28 is the amino acid sequence for the variable heavy chain referred to herein as CAN-SSM58-VH SEQ ID NO: 29 is the amino acid sequence for the variable heavy chain referred to herein as CAN-SSM66-VH SEQ ID NO: 30 is the amino acid sequence for the variable heavy chain referred to herein as CAN-SSMQC23-VL SEQ ID NO: 31 is the nucleotide sequence encoding the variable light chain referred to herein as MU-RN911-VLnt SEQ ID NO: 32 is the nucleotide sequence encoding the variable heavy chain referred to herein as MU-RN911-VHnt)

SEQ ID NO: 33 is the nucleotide sequence encoding the variable light chain referred to herein as CAN-E3M-VLnt SEQ ID NO: 34 is the nucleotide sequence encoding the variable heavy chain referred to herein as CAN-N2G9-VHnt SEQ ID NO: 35 is the nucleotide sequence encoding the variable light chain referred to herein as CAN-618-VLnt SEQ ID NO: 36 is the nucleotide sequence encoding the variable light chain referred to herein as CAN-QC23-VLnt SEQ ID NO: 37 is the nucleotide sequence encoding the variable light chain referred to herein as CAN-LTM109-VLnt SEQ ID NO: 38 is the nucleotide sequence encoding the variable heavy chain referred to herein as CAN-LTM109-VHnt SEQ ID NO: 39 is the nucleotide sequence encoding the variable light chain referred to herein as CAN-SSME3M-VLnt SEQ ID NO: 40 is the nucleotide sequence encoding the variable heavy chain referred to herein as CAN-SSM57-VHnt SEQ ID NO: 41 is the nucleotide sequence encoding the variable heavy chain referred to herein as CAN-SSM58-VHnt SEQ ID NO: 42 is the nucleotide sequence encoding the variable heavy chain referred to herein as CAN-SSM66-VHnt SEQ ID NO: 43 is the nucleotide sequence encoding the variable light chain referred to herein as CAN-SSMQC23-VLnt SEQ ID NO: 44 is the amino acid sequence for the canine heavy chain constant region referred to herein as CAN-65E-HC SEQ ID NO: 45 is the nucleotide sequence encoding the canine heavy chain constant region referred to herein as CAN-65E-HCnt)

SEQ ID NO: 46 is the amino acid sequence for the canine kappa constant light chain region and referred to herein as CAN-KAPPA-LC SEQ ID NO: 47 is the nucleotide sequence for the canine kappa constant light chain region and referred to herein as CAN-KAPPA-LCnt SEQ ID NO: 48 is the nucleotide sequence for the canine heavy chain constant region referred to herein as CAN-65 HCnt SEQ ID NO. 49 is the amino acid sequence for the canine heavy chain constant region referred to herein as CAN-65 HC SEQ ID NO. 50 is the amino acid sequence of Canis lupus familiaris Nerve Growth Factor Genbank Accession No. AAY16195

SEQ ID NO. 51 is the nucleotide sequence of Canis lupus familiaris Nerve Growth Factor SEQ ID NO. 52 is the amino acid sequence of Canine Nerve Growth Factor, partial sequence as seen in FIG. 6B SEQ ID NO. 53 is the amino acid sequence of Feline Nerve Growth Factor, partial sequence as seen in FIG. 6B SEQ ID NO. 54 is the amino acid sequence of Human Nerve Growth Factor, partial sequence as seen in FIG. 6B SEQ ID NO. 55 is the amino acid sequence of Murine Nerve Growth Factor, partial sequence as seen in FIG. 6B SEQ ID NO. 56 is the amino acid sequence of Rat Nerve Growth Factor, partial sequence as seen in FIG. 6B SEQ ID NO. 57 is the amino acid sequence of framework substitutions made to light chain variable region to regain expression and retain binding of RN911.

SEQ ID NO. 58 is the amino acid sequence of framework substitutions made to light chain variable region to regain expression and retain binding of Can911_gapped.

SEQ ID NO. 59 is the amino acid sequence of framework substitutions made to light chain variable region to regain expression and retain binding Can911.

SEQ ID NO. 60 is the amino acid sequence of framework substitutions made to light chain variable region to regain expression and retain binding of QC23LC SEQ ID NO. 61 is the consensus amino acid sequence of the light chain variable region after framework substitutions of SEQ ID NOs 57-60.

SEQ ID NO.62 is the amino acid sequence of the RN911 heavy chain variable region SEQ ID NO.63 is the amino acid sequence of the E3 heavy chain variable region SEQ ID NO.64 is the amino acid sequence of the A01 heavy chain variable region SEQ ID NO.65 is the amino acid sequence of the B01 heavy chain variable region SEQ ID NO.66 is the amino acid sequence of the B06 heavy chain variable region SEQ ID NO.67 is the amino acid sequence of the F03 heavy chain variable region SEQ ID NO.68 is the amino acid sequence of the F06 heavy chain variable region SEQ ID NO.69 is the amino acid sequence of the D10 heavy chain variable region SEQ ID NO.70 is the amino acid sequence of the E07 heavy chain variable region SEQ ID NO.71 is the amino acid sequence of the C07 heavy chain variable region SEQ ID NO.72 is the amino acid sequence of the C09 heavy chain variable region SEQ ID NO.73 is the amino acid sequence of the A02 heavy chain variable region SEQ ID NO.74 is the amino acid sequence of the D08 heavy chain variable region SEQ ID NO.75 is the amino acid sequence of the D09 heavy chain variable region SEQ ID NO.76 is the amino acid sequence of the A11 heavy chain variable region SEQ ID NO.77 is the amino acid sequence of the C12 heavy chain variable region SEQ ID NO.78 is the amino acid sequence of the H11 heavy chain variable region SEQ ID NO.79 is the amino acid sequence of the F11 heavy chain variable region SEQ ID NO.80 is the amino acid sequence of the A08 heavy chain variable region SEQ ID NO.81 is the amino acid sequence of the C06 heavy chain variable region SEQ ID NO.82 is the amino acid sequence of the ImP2_E06 heavy chain variable region SEQ ID NO.83 is the amino acid sequence of the ImP2_C08 heavy chain variable region SEQ ID NO.84 is the amino acid sequence of the ImP2_H06 heavy chain variable region SEQ ID NO.85 is the amino acid sequence of the ImP1_G12 heavy chain variable region SEQ ID NO.86 is the amino acid sequence of the ImP1_B02 heavy chain variable region SEQ ID NO.87 is the amino acid sequence of the ImP2_G12 heavy chain variable region SEQ ID NO.88 is the amino acid sequence of the ImP2_G02 heavy chain variable region SEQ ID NO.89 is the amino acid sequence of the ImmRB11 heavy chain variable region SEQ ID NO. 90 is the amino acid sequence of the ImmRD07 heavy chain variable region SEQ ID NO.91 is the amino acid sequence of the ImmRC08 heavy chain variable region SEQ ID NO.92 is the amino acid sequence of the ImmRE08 heavy chain variable region SEQ ID NO.93 is the amino acid sequence of the ImmRA06 heavy chain variable region SEQ ID NO.94 is the amino acid sequence of the ImmRA10 heavy chain variable region SEQ ID NO.95 is the amino acid sequence of the ImmRH02 heavy chain variable region SEQ ID NO.96 is the amino acid sequence of the ImmRG09 heavy chain variable region SEQ ID NO.97 is the amino acid sequence of the ImmRD12 heavy chain variable region SEQ ID NO.98 is the amino acid sequence of the ImmRE04 heavy chain variable region SEQ ID NO.99 is the amino acid sequence of the ImmRC06 heavy chain variable region SEQ ID NO.100 is the amino acid sequence of the ImmRG02 heavy chain variable region SEQ ID NO.101 is the amino acid sequence of the ImmRA11 heavy chain variable region SEQ ID NO.102 is the amino acid sequence of the ImmRC02 heavy chain variable region SEQ ID NO.103 is the amino acid sequence of the ImmRG03 heavy chain variable region

DETAILED DESCRIPTION OF THE INVENTION

The invention disclosed herein provides caninized anti-NGF antigen binding proteins that bind canine NGF with high affinity. The invention further provides caninized antigen binding proteins and polypeptides that also bind to canine NGF that are variants of said antigen binding proteins as well as methods of making and using these antigen binding proteins. In some embodiments, the invention also provides polynucleotides encoding said antigen binding proteins and/or polypeptide. The invention disclosed herein also provides methods for preventing and/or treating pain in a canine by administration of a therapeutically effective amount of the caninized anti-NGF antigen binding proteins.

General Techniques

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

All patents and other publications identified are expressly incorporated herein by reference for the purpose of describing and disclosing, for example, the methodologies described in such publications that might be used in connection with the present invention. These publications are provided solely for their disclosure prior to the filing date of the present application Standard techniques are used for recombinant DNA, oligonucleotide synthesis, and tissue culture and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described, but not limited to the various general and more specific references that are cited and discussed throughout the present specification, See e.g., Sambrook et al. MOLECULAR CLONING: LAB. MANUAL (3$^{rd}$ ed., Cold Spring Harbor Lab. Press, Cold Spring Harbor, N.Y., 2001) and Ausubel et al. Current Protocols in Molecular Biology (New York: Greene Publishing Association J Wiley Interscience), Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. 1. Freshney, ed. 1987); *Introduction to Cell and Tissue Culture* (l. P. Mather and P. E. Roberts, 1998) Plenum Press; *Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (Y. T. DeVita et al., eds., J.B. Lippincott Company, 1993).

Other than in the operating examples, or where otherwise indicated, all numbers expressing quantities of ingredients or reaction conditions used herein should be understood as modified in all instances by the term "about."

Definitions

Before describing the present invention in detail, several terms used in the context of the present invention will be defined. In addition to these terms, others are defined elsewhere in the specification as necessary. Unless otherwise expressly defined herein, terms of art used in this specification will have their art-recognized meanings.

As used in the specification and claims, the singular form "a", "an" and "the" includes plural references unless the context clearly dictates otherwise. For example, reference to "an antibody" includes a plurality of such antibodies.

As used herein, the term "comprising" is intended to mean that the compositions and methods include the recited elements, but not excluding others.

As used herein, the term "nerve growth factor" and "NGF" refers to nerve growth factor and variants thereof that retain at least part of the biological activity of NGF.

"NGF receptor" refers to a polypeptide that is bound by or activated by NGF. NGF receptors include the TrkA receptor and to a lesser extent the p75 receptor of canines.

"Biological activity" of NGF generally refers to the ability to bind NGF receptors and/or activate NGF receptor signaling pathways. Without limitation, a biological activity includes anyone or more of the following: the ability to bind an NGF receptor (such as TrkA and/or p75); the ability to promote TrkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; the ability to promote survival of mouse E13.5 trigeminal neurons; and the ability to mediate pain, including post-surgical pain.

As used herein, an "anti-NGF antigen binding protein" (interchangeably termed "anti-NGF antibody" and "anti-NGF antagonist antibody") refers to an antigen binding protein which is able to bind to NGF and inhibit NGF biological activity and/or downstream pathway(s) mediated by NGF signaling. An anti-NGF antagonist antibody encompasses antibodies that block, antagonize, suppress or reduce (including significantly) NGF biological activity, including downstream pathways mediated by NGF signaling and/or inhibit NGF from binding to its receptor trkA, such as receptor binding and/or elicitation of a cellular response to NGF. For purpose of the present invention, it will be explicitly understood that the term "anti-NGF antagonist antibody" encompass all the previously identified terms, titles, and functional states and characteristics whereby the NGF itself, an NGF biological activity (including but not limited to its ability to ability to mediate any aspect of post-surgical pain), or the consequences of the biological activity, are substantially nullified, decreased, or neutralized in any meaningful degree. In some embodiments, an anti-NGF antagonist antibody binds NGF and prevent NGF dimerization and/or binding to an NGF receptor (such as TrkA and/or p75). In other embodiments, an anti-NGF antibody binds NGF and prevents TrkA receptor dimerization and/or TrkA autophosphorylation. Examples of anti-NGF antagonist antibodies are provided herein.

As used herein, the term "antigen binding protein", "antibody" and the like, which may be used interchangeably, refers to a polypeptide, or fragment thereof, comprising an antigen binding site. In one embodiment of the present invention the antigen binding protein of the invention further provides an intact immunoglobulin capable of specific binding to a target, such as a carbohydrate, polynucleotide, lipid, polypeptide, etc., through at least one antigen recognition site located in the variable region of the immunoglobulin molecule. An intact antibody has two light and two heavy chains. Thus a single isolated intact antibody may be a polyclonal antibody, a monoclonal antibody, a synthetic antibody, a recombinant antibody, a chimeric antibody, a heterochimeric antibody. The term "antigen binding protein" "antibody' preferably refers to monoclonal antibodies and fragments thereof, and immunologic binding equivalents thereof that can bind to the NGF protein and fragments thereof. The term antibody and antigen binding protein are used to refer to a homogeneous molecular, or a mixture such as a serum product made up of a plurality of different molecular entities. As used herein, the term encompasses not only intact polyclonal or monoclonal antibodies, but also fragments thereof. For the purposes of the present invention, "antibody" and "antigen binding protein" also includes antibody fragments, unless otherwise stated. Exemplary antibody fragments include Fab, Fab', F(ab')2, Fv, scFv, Fd, dAb, diabodies, their antigen-recognizing fragments, small modular immunopharmaceuticals (SMIPs) nanobodies, IgNAR molecules and the like all recognized by one of skill in the art to be an antigen binding protein or antibody fragment and any of above mentioned fragments and their chemically or genetically manipulated counterparts, as well as other antibody fragments and mutants thereof, fusion proteins comprising an antibody portion, and any other modified configuration of the immunoglobulin molecule that comprises an antigen recognition site. Antibodies and antigen binding proteins can be made, for example, via traditional hybridoma techniques (Kohler et al., Nature 256:495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991)). For various other antibody production techniques, see Antibodies: A Laboratory Manual, eds. Harlow et al., *Cold Spring Harbor Laboratory*, 1988 as well as other techniques that are well known to those skilled in the art.

A "monoclonal antibody" as defined herein is an antibody produced by a single clone of cells (specifically, a single clone of hybridoma cells) and therefore a single pure homogeneous type of antibody. All monoclonal antibodies produced from the same clone are identical and have the same antigen specificity. Monoclonal antibodies are a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (Fab, Fab', F(ab')2, Fv, scFv, Fd, dAb, diabodies, their antigen-recognizing fragments, small modular immunopharmaceuticals (SMIPs) nanobodies, IgNAR molecules and the like), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

Figure 2:
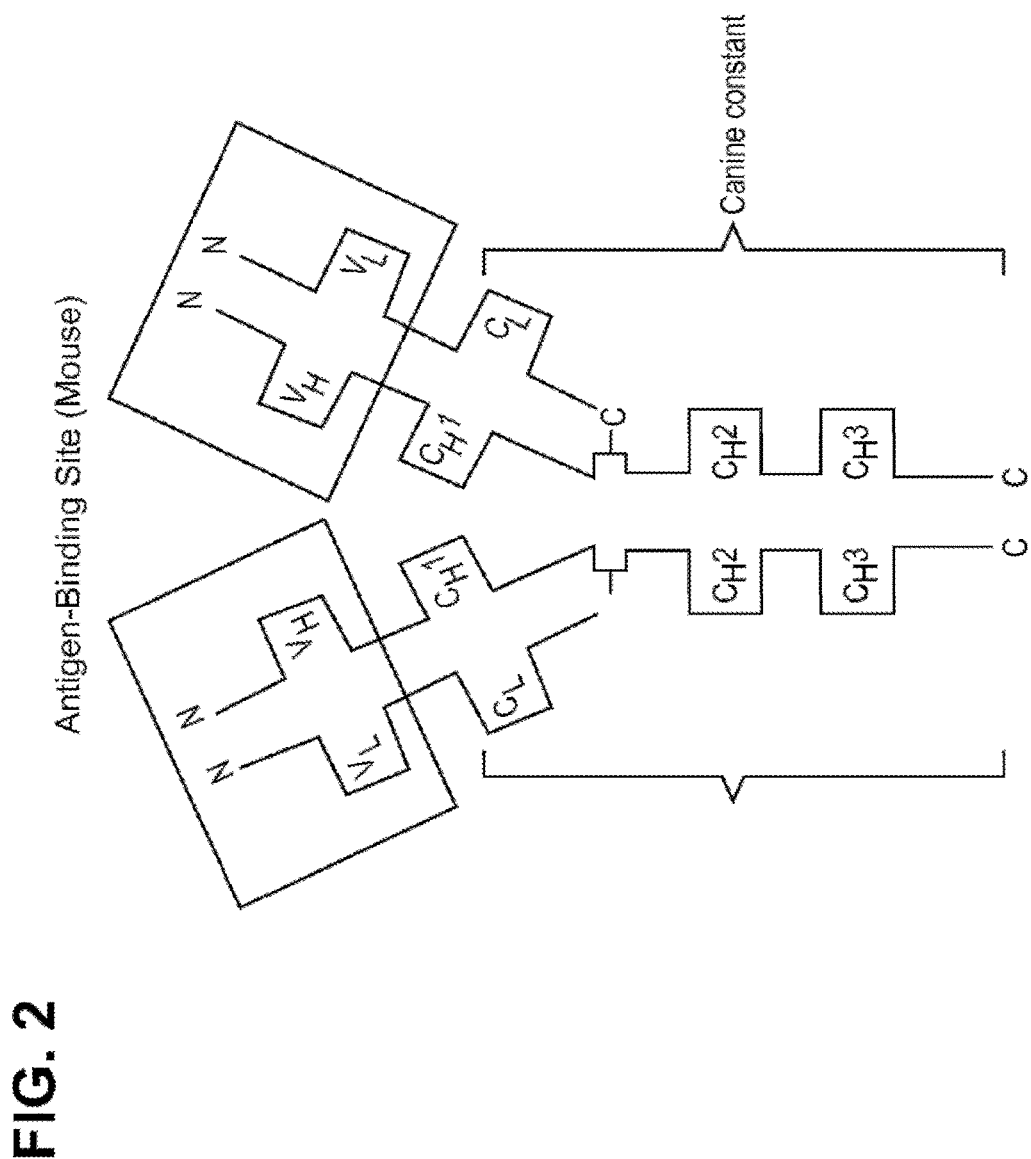
FIG. 2: is a schematic representation of the general structure of a mouse/canine chimeric IgG.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity. Typically, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to canine constant segments. FIG. 2 is a schematic representation of the general structure of one embodiment of a mouse: canine IgG. In this embodiment, the antigen binding site is derived from mouse while the Fc portion is canine.

Figure 4:
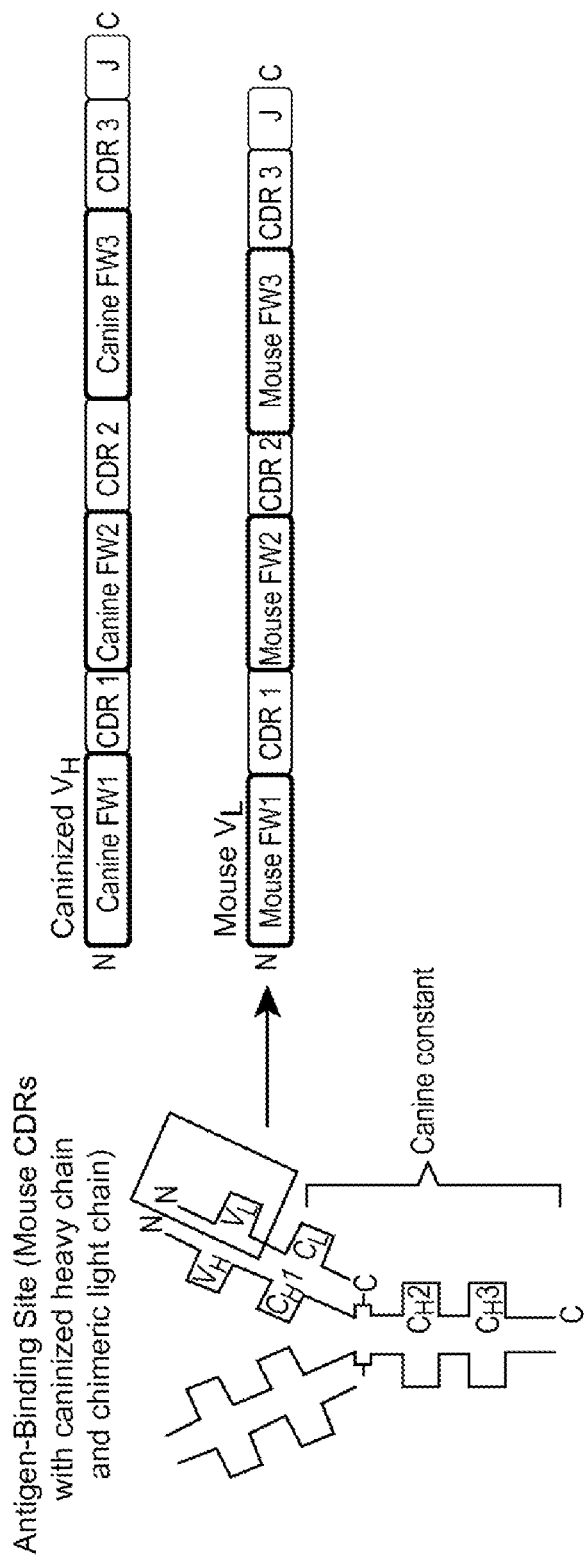
FIG. 4 is an illustration of a "heterochimeric monoclonal antibody paring the chimeric light chain with a fully caninized heavy chain.
Figure 5:
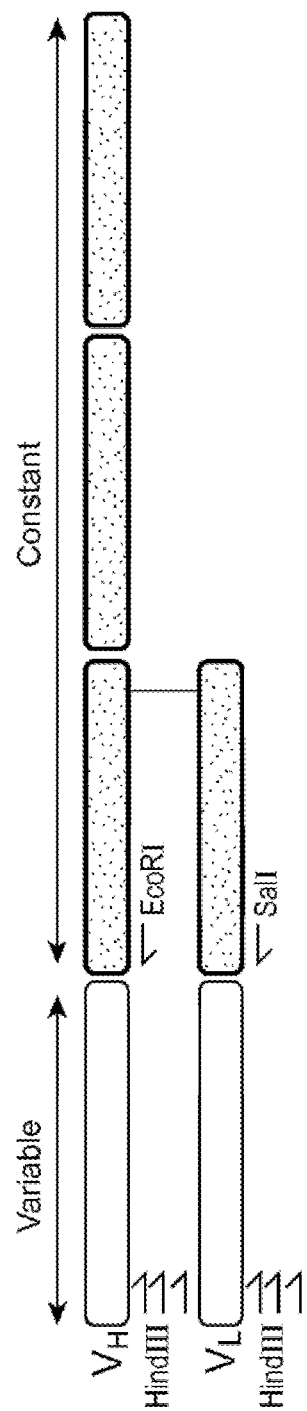
FIG. 5 is an illustration of antibody variable chains showing primers to constant regions and degenerate primers directed at mouse variable regions.

The term "heterochimeric" as defined herein, refers to an antibody in which one of the antibody chains (heavy or light) is caninized while the other is chimeric. FIG. 4 depicts one embodiment of a heterochimeric molecule. In this embodiment, a caninized variable heavy chain (where all of the CDRs are mouse and all FRs are canine) is paired with a chimeric variable light chain (where all of the CDRs are mouse and all FRs are mouse. In this embodiment, both the variable heavy and variable light chains are fused to a canine constant region.

Figure 3:
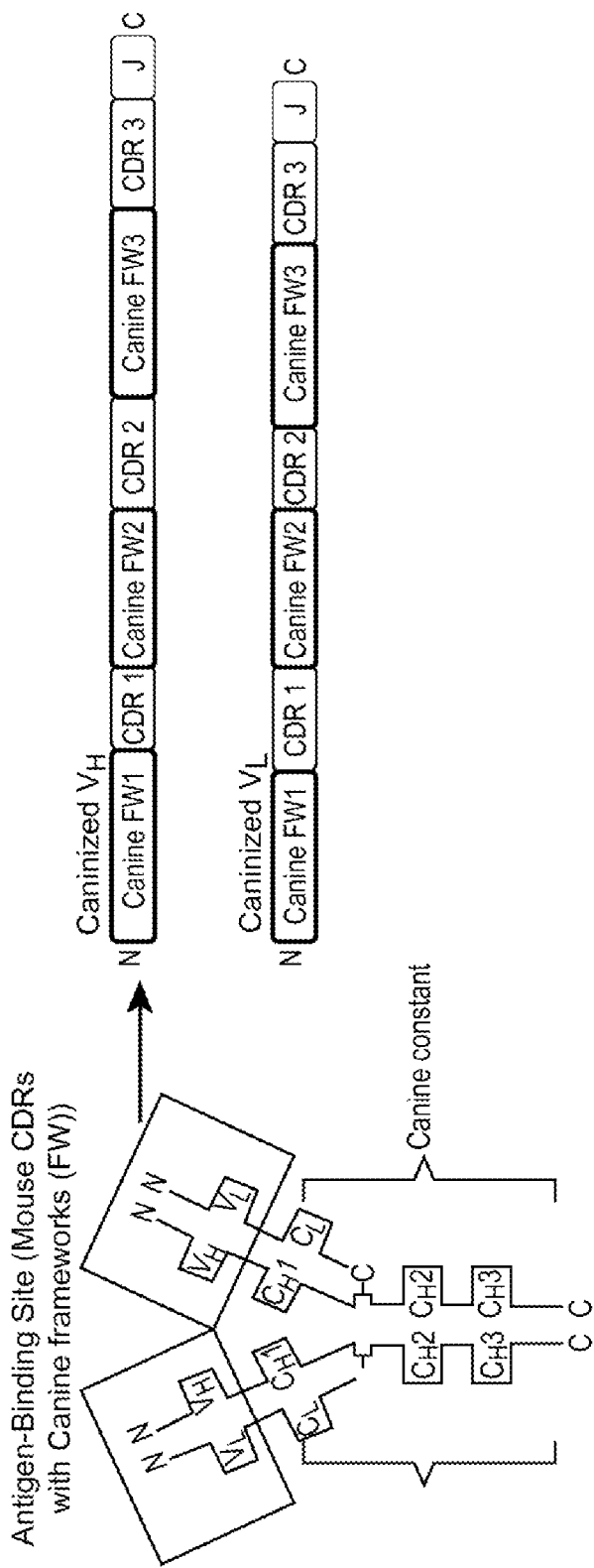
FIG. 3: is an illustration showing speciation or "caninization" of a mouse IgG, mouse CDRs are grafted onto canine frameworks.

"Caninized" forms of non-canine (e.g., murine) antibodies are genetically engineered antibodies that contain minimal sequence derived from non-canine immunoglobulin. "Caninization" is defined as a method for transferring non-canine antigen-binding information from a donor antibody to a less immunogenic canine antibody acceptor to generate treatments useful as therapeutics in dogs. Caninized antibodies are canine immunoglobulins (recipient antibody) in which hypervariable region residues of the recipient are replaced by hypervariable region residues from a non-canine species (donor antibody) such as such as mouse, rat, rabbit, cat, dogs, goat, chicken, bovine, horse, llama, camel, dromedaries, sharks, non-human primates, human, humanized, recombinant sequence, or an engineered sequence having the desired properties, specificity, affinity, and capacity. In some instances, framework region (FR) residues of the canine immunoglobulin are replaced by corresponding non-canine residues. Furthermore, caninized antibodies may include residues that are not found in the recipient antibody or in the donor antibody. These modifications are made to further refine antibody performance. The modifications to the hypervariable regions and/or the framework regions, as described herein, are determined for each separately engineered speciated (caninized) antibody based on experimentation known to those in the art and cannot be predicted prior to said experimentation. In general, the caninized antibody will include substantially all of at least one, and typically two, variable domains, in which all or substantially all of the hypervariable regions correspond to those of a non-canine immunoglobulin and all or substantially all of the FRs are those of a canine immunoglobulin sequence. The caninized antibody optionally also will comprise a complete, or at least a portion of an immunoglobulin constant region (Fc), typically that of a canine immunoglobulin. FIG. 3 is an illustration of one embodiment showing speciation or caninization of a mouse IgG. In this embodiment, mouse CDRs are grafted onto canine frameworks. In some cases, mouse frameworks or residues therein that are outside of the hypervariable region are maintained.

The phrase "recombinant canine antibody" includes canine antibodies that are prepared, expressed, created or isolated by recombinant means, such as antibodies expressed using a recombinant expression vector transfected into a host cell, antibodies isolated from a recombinant, combinatorial canine antibody library, antibodies isolated from an animal (e.g., a mouse) that is transgenic for canine immunoglobulin genes (see e.g., Taylor, L. D., et al. (1992) Nucl. Acids Res. 20:6287-6295) or antibodies prepared, expressed, created or isolated by any other means that involves splicing of canine immunoglobulin gene sequences to other DNA sequences.

The term "canine antibody", as used herein, refers to a canine antibody that is generated against a target and is prepared by hybridoma methods well known to one skilled in the art and described herein.

"Native antibodies" and "native immunoglobulins" are usually heterotetrameric glycoproteins of about 150,000 Daltons, composed of two identical light (l) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. FIG. 1 is an example of the general structure of a native mouse immunoglobulin G (IgG) highlighting the antigen binding site.

The "parent" antibody herein is one that is encoded by an amino acid sequence used for the preparation of the variant. Preferably, the parent antibody has a canine framework region and, if present, has canine antibody constant region(s). For example, the parent antibody may be a caninized or canine antibody.

Depending on the amino acid sequence of the constant domain of the heavy chains of antibodies, immunoglobulins can be assigned to different classes. Presently there are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, IgA, and $IgA_2$ (as defined by mouse and human designation). The heavy-chain constant domains that correspond to the different classes of immunoglobulins are called alpha, delta, epsilon, gamma, and mu, respectively. The subunit structures and three-dimensional configurations of different classes of immunoglobulins are well known in multiple species. The prevalence of individual isotypes and functional activities associated with these constant domains are species-specific and must be experimentally defined.

The "light chains" of antibodies (immunoglobulins) from any vertebrate species can be assigned to one of two clearly distinct types, called kappa (K) and lambda (λ), based on the amino acid sequences of their constant domains.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (I) an approach based on cross-species sequence variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Chothia et al. (1989) *Nature* 342:877; AI-Iazikani et al (1997) *J. Molec. Bioi.* 273:927-948)). As used herein, a CDR may refer to CDRs defined by either approach or by a combination of both approaches.

The term "hypervariable region" when used herein refers to the amino acid residues of an antibody which are responsible for antigen binding. The hypervariable region comprises amino acid residues from a "complementarity determining region" or "CDR" (Kabat, et al. (1991), above) and/or those residues from a "hypervariable loop" (Chothia and Lesk *J. Mol. Biol.* 196:901-917 (1987). "Framework" or "FR" residues are those variable domain residues other than the hypervariable region residues as herein defined.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues.

A "functional Fc region" possesses at least one effector function of a native sequence Fc region. Exemplary "effector functions" include C1q binding; complement dependent cytotoxicity (CDC); Fc receptor binding; neonatal receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" or a "mutated" or "mutant" Fc region comprises an amino acid sequence which differs from that of a native sequence Fc region by virtue of at least one amino acid modification, and may or may not retain at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith. A variant or mutated Fc region may also essentially eliminate the function of the Fc region of the antibody. For example Fc region mutations may eliminate effector function of the antibody. In one embodiment of the invention the antibody of the invention comprises a mutated Fc region.

As used herein, "Fc receptor" and "FcR" describe a receptor that binds to the Fc region of an antibody. The preferred FcR is a native sequence FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, *PNAS* (USA), 95:652-656.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods,* 202: 163 (1996), may be performed.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab') 2 antibody fragments originally were produced as pairs of Fab' fragments which have hinge cysteines between them. Other chemical couplings of antibody fragments are also known.

"Fv" is the minimum antibody fragment that contains a complete antigen-recognition and binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

An "antigen", as used herein, refers to the antigenic determinant recognized by the CDRs of the antigen binding protein or antibody as described herein. In other words, epitope refers to that portion of any molecule capable of being recognized by, and bound by, an antibody. Unless indicated otherwise, the term "epitope" as used herein, refers to the region of NGF to which an anti-NGF antigen binding protein/antibody/agent binds.

The term "antigen binding domain," "active fragments of an antibody" or the like refers to the part of an antibody or antigen binding protein that comprises the area specifically binding to or complementary to a part or all of an antigen. Where an antigen is large, an antibody may only bind to a particular part of the antigen. The "epitope," "active fragments of an epitope," or "antigenic determinant" or the like is a portion of an antigen molecule that is responsible for specific interactions with the antigen binding domain of an antibody. An antigen binding domain may be provided by one or more antibody variable domains (e.g., a so-called Fd antibody fragment consisting of a VH domain). An antigen binding domain may comprise an antibody light chain variable domain (VL) and an antibody heavy chain variable domain (VH) (U.S. Pat. No. 5,565,332).

The terms "binding portion" of an antibody (or "antibody portion") or antigen-binding polypeptide or the like includes one or more complete domains, e.g., a pair of complete domains, as well as fragments of an antibody that retain the ability to specifically bind to an antigen, e.g., NGF. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab') 2, Fabc, Fd, dAb, Fv, single chains, single-chain antibodies, e.g., scFv, and single domain antibodies (Muyldermans et al., 2001, 26:230-5), and an isolated complementarity determining region (CDR). Fab fragment is a monovalent fragment consisting of the VL, VH, CL and CH1 domains. F(ab)$_2$ fragment is a bivalent fragment comprising two Fab fragments linked by a disulfide bridge at the hinge region. Fd fragment consists of the VH and CH1 domains, and Fv fragment consists of the VL and VH domains of a single arm of an antibody. A dAb fragment consists of a VH domain (Ward et al., (1989) Nature 341:544-546). While the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv) (Bird et al., 1988, Science 242:423-426). Such single chain antibodies are also intended to be encompassed within the term "binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, et al., 1993, Proc. Natl. Acad. Sci. USA 90:6444-6448). An antibody or binding portion thereof also may be part of a larger immunoadhesion molecules formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Binding fragments such as Fab and F(ab') 2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein and as known in the art. Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. A bispecific antibody can also include two antigen binding regions with an intervening constant region. Bispecific antibodies can be produced by a variety of methods including fusion of hybridomas or linking of Fab' fragments. See, e.g., Songsivilai et al., *Clin. Exp. Immunol.* 79:315-321, 1990.; Kostelny et al., 1992, J. Immunol. 148, 1547-1553.

The term "backmutation" refers to a process in which some or all of the somatically mutated amino acids of a canine antibody are replaced with the corresponding germline residues from a homologous germline antibody sequence. The heavy and light chain sequences of the canine antibody of the invention are aligned separately with the germline sequences to identify the sequences with the highest homology. Differences in the canine antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the canine antibody should not be included in the final canine antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and colinear to the sequence of the canine antibody of the invention. Back mutation of selected target framework residues to the corresponding donor residues might be required to restore and or improved affinity.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins). An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an NGF epitope is an antibody that binds this epitope with greater affinity, avidity, more readily, and/or with greater duration than it binds to other NGF epitopes or non-NGF epitopes. It is also understood by reading this definition that, for example, an antibody (or moiety or epitope) that specifically or preferentially binds to a first target mayor may not specifically or preferentially bind to a second target. As such, "specific binding" or "preferential binding" does not necessarily require (although it can include) exclusive binding. Generally, but not necessarily, reference to binding means preferential binding.

The term "specifically" in the context of antibody binding, refers to high avidity and/or high affinity binding of an antibody to a specific antigen, i.e., a polypeptide, or epitope. Antibody specifically binding an antigen is stronger than binding of the same antibody to other antigens. Antibodies which bind specifically to a polypeptide may be capable of binding other polypeptides at a weak, yet detectable level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to an antigen with a binding affinity with a $K_d$ of $10^{-7}$ M or less, e.g., $10^{-8}$ M or less e.g., $10^{-9}$ M or less, $10^{-10}$ or less, $10^{-11}$ or less, $10^{-12}$ or less, or $10^{-13}$ or less etc.

As used herein, the term "affinity" refers to the strength of the binding of a single antigen-combining site with an antigenic determinant. Affinity depends on the closeness of stereochemical fit between antibody or antigen binding protein combining sites and antigen determinants, on the size of the area of contact between them, on the distribution of charged and hydrophobic groups, etc. Antibody affinity can be measured by equilibrium analysis or by the Surface Plasmon Resonance—"SPR" method (for example BIA-CORE™. The SPR method relies on the phenomenon of surface plasmon resonance (SPR), which occurs when surface plasmon waves are excited at a metal/liquid interface. Light is directed at, and reflected from, the side of the surface not in contact with sample, and SPR causes a reduction in the reflected light intensity at a specific combination of angle and wavelength. Bimolecular binding events cause changes in the refractive index at the surface layer, which are detected as changes in the SPR signal.

The term "Kd', as used herein, is intended to refer to the dissociation constant of an antibody-antigen interaction. The dissociation constant, Kd, and the association constant, Ka, are quantitative measures of affinity. At equilibrium, free antigen (Ag) and free antibody (Ab) are in equilibrium with antigen-antibody complex (Ag-Ab), and the rate constants, ka and kd, quantitate the rates of the individual reactions. At equilibrium, ka [Ab][Ag]=kd [Ag-Ab]. The dissociation constant, Kd, is given by: Kd=kd/ka=[Ag][Ab]/[Ag-Ab]. Kd has units of concentration, most typically M, mM, µM, nM, pM, etc. When comparing antibody affinities expressed as Kd, having greater affinity for NGF is indicated by a lower value. The association constant, Ka, is given by: Ka=ka/kd= [Ag-Ab]/[Ag][Ab]. Ka has units of inverse concentration, most typically $M^{-1}$, $mM^{-1}$, $.\mu M^{-1}$, $nM^{-1}$, $pM^{-1}$, etc. As used herein, the term "avidity" refers to the strength of the antigen-antibody bond after formation of reversible complexes. Anti-NGF antibodies may be characterized in terms of the Kd for their binding to a NGF protein, as binding "with a dissociation constant (Kd) in the range of from about (lower Kd value) to about (upper Kd value)."

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, un-natural amino acids, etc.), as well as other modifications known in the art. It is understood that, because the polypeptides of this invention are based upon an antibody, the polypeptides can occur as single chains or associated chains.

The term 'conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. Nos. 6,790,639, 6,774,107, 6,194,167, or 5,350,576. In a preferred embodiment, a conservative amino acid substitution will be anyone that occurs within one of the following six groups:
1. Small aliphatic, substantially non-polar residues: Ala, Gly, Pro, Ser, and Thr;
2. Large aliphatic, non-polar residues: lie, Leu, and Val; Met;
3. Polar, negatively charged residues and their amides: Asp and Glu;
4. Amides of polar, negatively charged residues: Asn and Gin; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gin; His); Asp (Glu); Gin (Asn); Glu (Asp); Gly (Pro); His (Asn;Gin); lie (Leu; Val); Leu (lie; Val); Lys (Arg; Gin; Glu); Met (Leu; lie); Phe (Met; Leu; Tyr); Ser (Thr); Thr (Ser); Trp (Tyr); Tyr (Trp; Phe); and Val (lie; Leu).

The terms "nucleic acid", "polynucleotide", "nucleic acid molecule" and the like may be used interchangeably herein and refer to a series of nucleotide bases (also called "nucleotides") in DNA and RNA. The nucleic acid may contain deoxyribonucleotides, ribonucleotides, and/or their analogs. The term "nucleic acid" includes, for example, single-stranded and double-stranded molecules. A nucleic acid can be, for example, a gene or gene fragment, exons, introns, a DNA molecule (e.g., cDNA), an RNA molecule (e.g., mRNA), recombinant nucleic acids, plasmids, and other vectors, primers and probes. Both 5' to 3' (sense) and 3' to 5' (antisense) polynucleotides are included. The nucleotides can be deoxyribonucleotides, ribonucleotides, modified nucleotides or bases, and/or their analogs, or any substrate that can be incorporated into a polymer by DNA or RNA polymerase. A poly-nucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-0-allyl, 2'-fluoro- or 2'-azido-ribose, carbocyclic sugar analogs, anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (-0-) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Vectors, as described herein, have expression control sequences meaning that a nucleic acid sequence that directs transcription of a nucleic acid. An expression control sequence can be a promoter, such as a constitutive or an inducible promoter, or an enhancer. The expression control sequence is 'operably linked' to the nucleic acid sequence to be transcribed. A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Just as a polypeptide may contain conservative amino acid substitution(s), a polynucleotide thereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

A "variant" anti-NGF antibody, refers herein to a molecule which differs in amino acid sequence from a "parent" anti-NGF antibody amino acid sequence by virtue of addition, deletion, and/or substitution of one or more amino acid residue(s) in the parent antibody sequence and retains at least one desired activity of the parent anti-NGF-antibody. The variant anti-NGF may comprise conservative amino acid substitutions in the hypervariable region of the antibody, as described herein. Desired activities can include the ability to bind the antigen specifically, the ability to reduce, inhibit or neutralize NGF activity in an animal. In one embodiment, the variant comprises one or more amino acid substitution(s) in one or more hypervariable and/or framework region(s) of the parent antibody. For example, the variant may comprise at least one, e.g. from about one to about ten, and preferably from about two to about five, substitutions in one or more hypervariable and/or framework regions of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity.

None of N-terminal, C-terminal, or internal extensions, deletions, or insertions into the antibody sequence shall be construed as affecting sequence identity or homology. The variant retains the ability to bind NGF and preferably has desired activities which are equal to or superior to those of the parent antibody. For example, the variant may have a stronger binding affinity, enhanced ability to reduce, inhibit or neutralize NGF activity in an animal, and/or enhanced ability to inhibit NGF binding to Trk A and p75.

Trk A, considered the high affinity NGF receptor is a member of the neurotrophic tyrosine kinase receptor (NTKR) family. This kinase is a membrane-bound receptor that, upon neurotrophin binding, phosphorylates itself (autophosphorylation) and members of the MAPK pathway. The presence of this kinase leads to cell differentiation and may play a role in specifying sensory neuron subtypes. The p75 receptor is considered the low affinity NGF receptor.

A 'variant" nucleic acid, refers herein to a molecule which differs in sequence from a "parent" nucleic acid. Polynucleotide sequence divergence may result from mutational changes such as deletions, substitutions, or additions of one or more nucleotides. Each of these changes may occur alone or in combination, one or more times in a given sequence.

The term "isolated" means that the material (e.g., antibody or nucleic acid) is separated and/or recovered from a component of its natural environment. Contaminant components of its natural environment are materials that would interfere with diagnostic or therapeutic uses for the material, and may include enzymes, hormones, and other proteinaceous or non-proteinaceous solutes. With respect to nucleic acid, an isolated nucleic acid may include one that is separated from the 5' to 3' sequences with which it is normally associated in the chromosome. In preferred embodiments, the material will be purified to greater than 95% by weight of the material, and most preferably more than 99% by weight. Isolated material includes the material in situ within recombinant cells since at least one component of the material's natural environment will not be present. Ordinarily, however, isolated material will be prepared by at least one purification step.

As used herein, the terms "cell", "cell line", and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells, yeast cells, mammalian cells, and insect cells) whether located in vitro or in vivo. For example, host cells may be located in a transgenic animal. Host cell can be used as a recipient for vectors and may include any transformable organism that is capable of replicating a vector and/or expressing a heterologous nucleic acid encoded by a vector.

The word "label" when used herein refers to a detectable compound or composition that is conjugated directly or indirectly to the antibody or nucleic acid. The label may itself be detectable by itself (e.g., radioisotope labels or fluorescent labels) or, in the case of an enzymatic label, may catalyze chemical alteration of a substrate compound or composition that is detectable.

A "subject" or "patient" refers to an animal in need of treatment that can be affected by molecules of the invention. Animals that can be treated in accordance with the invention include vertebrates, with mammals such as canine being particularly preferred examples.

A "composition" is intended to mean a combination of active agent, whether chemical composition, biological composition or biotherapeutic (particularly antigen binding proteins as described herein) and another compound or composition which can be inert (e.g., a label), or active, such as an adjuvant.

As defined herein, "pharmaceutically acceptable carriers" suitable for use in the invention are well known to those of skill in the art. Such carriers include, without limitation, water, saline, buffered saline, phosphate buffer, alcohol/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, pub!., 2000; and The Handbook of Pharmaceutical Excipients, 4.sup.th edit., eds. R. C. Rowe et al, APhA Publications, 2003.

A "therapeutically effective amount" (or "effective amount") refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated NGF related condition sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent pain, including post-surgical pain, rheumatoid arthritis pain, and/or osteoarthritis pain. In some embodiments, the "effective amount" may reduce pain at rest (resting pain) or mechanically-induced pain (including pain following movement), or both, and it may be administered before, during or after a painful stimulus. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. Of course, the therapeutically effective amount will vary depending upon the particular subject and condition being treated, the weight and age of the subject, the severity of the condition, the particular compound chosen, the dosing regimen to be followed, timing of administration, the manner of administration and the like, all of which can readily be determined by one of ordinary skill in the art.

As used herein, the term "therapeutic" encompasses the full spectrum of treatments for a disease, condition or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

In a further aspect, the invention features veterinary compositions in which antibodies of the present invention are provided for therapeutic or prophylactic uses. The invention features a method for treating a dog subject having a particular antigen, for example, one associated with a disease or condition. The method includes administering a therapeutically effective amount of a recombinant antibody specific for the particular antigen, with the recombinant antibody described herein.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. The route of administration of the antibody or antigen-binding moiety of the invention may be oral, parenteral, by inhalation or topical. In a preferred embodiment the route of administration is parenteral. The term parenteral as used herein includes intravenous, intramuscular, subcutaneous, rectal, vaginal or intraperitoneal administration.

"Pain" as used herein refers to pain of any etiology, including acute and chronic pain, and any pain with an inflammatory component. Examples of pain include including inflammatory pain, post-operative incision pain, neuropathic pain, fracture pain, osteoporotic fracture pain, post-herpetic neuralgia, cancer pain, pain resulting from burns, pain associated with burn or wound, pain associated with trauma (including traumatic head injury), neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

As used herein, "treatment" is an approach for obtaining beneficial or desired clinical results. For purposes of this invention, beneficial or desired clinical results include, but are not limited to, one or more of the following: improvement or alleviation of any aspect of pain, including acute, chronic, inflammatory, neuropathic, post-surgical pain, rheumatoid arthritis pain, or osteoarthritis pain. For purposes of this invention, beneficial or desired clinical results include, but are not limited to, one or more of the following: including lessening severity, alleviation of one or more symptoms associated with pain including any aspect of pain (such as shortening duration of pain, reduction of pain sensitivity or sensation).

NGF Related Disorder, as described herein, refers to a disorder including cardiovascular diseases, atherosclerosis, obesity, type 2 diabetes, metabolic syndrome, pain and inflammation. In some embodiments of the present invention an NGF related disorder refers to pain, in particular chronic pain, inflammatory pain, post-operative incision pain, neuropathic pain, fracture pain, osteoporotic fracture pain, post-herpetic neuralgia, cancer pain, pain resulting from burns, pain associated with burn or wound, pain associated with trauma (including traumatic head injury), neuropathic pain, pain associated with musculoskeletal disorders such as rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

"Reducing incidence" of pain means any of reducing severity (which can include reducing need for and/or amount of (e.g., exposure to) other drugs and/or therapies generally used for this conditions, including, for example, opiates), duration, and/or frequency (including, for example, delaying or increasing time to post-surgical pain in an individual). As is understood by those skilled in the art, individuals may vary in terms of their response to treatment, and, as such, for example, a "method of reducing incidence of rheumatoid arthritis pain or osteoarthritis pain in an individual" reflects administering the anti-NGF antagonist antibody based on a reasonable expectation that such administration may likely cause such a reduction in incidence in that particular individual.

"Ameliorating" a pain or one or more symptoms of a pain (such as rheumatoid arthritis pain or osteoarthritis pain) means a lessening or improvement of one or more symptoms of a pain as compared to not administering an anti-NGF antagonist antibody. "Ameliorating" also includes shortening or reduction in duration of a symptom.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with an anti-NGF antagonist antibody in accordance with the invention.

As used therein, "delaying" the development of pain means to defer, hinder, slow, retard, stabilize, and/or postpone progression of pain, such as post-surgical pain, rheumatoid arthritis pain, or osteoarthritis pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain. The pain can be primary or secondary pain, as is well-known in the art.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

The invention disclosed herein concerns antibodies, which is used interchangeably with the term "antigen binding protein" as described herein, that specifically bind to Nerve Growth Factor (NGF) and in particular antibodies, whether it be canine antibodies produced by hybridoma or phage display technology or fully "caninized" monoclonal antibodies that specifically bind to canine NGF and thus prevent canine NGF from binding to canine TrkA and to a lesser extent canine p75 receptors, thus serving as an antagonist in that the signaling pathway is prevented from being activated by NGF.

NGF was the first neurotrophin to be identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne et al. (1994) Nature 368:246-249; Crowley et al. (1994) Cell 76:1001-1011). NGF upregulates expression of neuropeptides in sensory neurons (Lindsay et al. (1989) Nature 337:362-364) and its activity is mediated through two different membrane-bound receptors, the TrkA receptor and what is considered the low affinity p75 common neurotrophin receptor.

NGF has been shown to be elevated in NGF related disorders in which an elevated amount of NGF is present in injured or diseased tissues. An NGF related disorder, can be defined as an increase in pain due to the elevation of NGF in an injured, diseased or damaged tissue. Pain, as used herein, is defined as described herein, refers to a disorder including chronic pain, inflammatory pain, post-operative incision pain, neuropathic pain, fracture pain, osteoporotic fracture pain, post-herpetic neuralgia, cancer pain, pain resulting from burns, pain associated with burn or wound, pain associated with trauma (including traumatic head injury), neuropathic pain, pain associated with musculoskeletal disorders such as chronic pain, rheumatoid arthritis, osteoarthritis, ankylosing spondylitis, seronegative (non-rheumatoid) arthropathies, non-articular rheumatism and periarticular disorders, and pain associated with cancer (including "break-through pain" and pain associated with terminal cancer), peripheral neuropathy and post-herpetic neuralgia.

In an embodiment of the present invention, an NGF disorder is defined as osteoarthritis in canines. Osteoarthritis (OA) is a slowly-progressive degenerative joint disease characterized by a loss of joint cartilage and the subsequent exposure of subchondral bone in canines. This eventually results in a self-perpetuating insidious disorder characterized by joint pain. New bone formation occurs in response to the chronic inflammation, and local tissue damage in an attempt to limit both movement and pain. Macroscopically, there is loss of joint cartilage, a narrowing of the joint space, sclerosis of subchondral bone, and the production of joint osteophytes (Veterinary Focus: Vol 17 No 3; 2007)

In canines, the onset of primary OA depends on breed. The onset mean age is 3.5 years in Rottweilers and 9.5 years in Poodles for examples, with a wide range of onset for other breeds as well as mixed breeds. The developmental orthopedic diseases and associated osteoarthritis are the most common articular diseases in dogs, they account for some 70% of medical visits for articular disease and related problems within the appendicular skeleton. Twenty two percent of cases were dogs aged one year or under. The incidence of OA is increased by trauma as well as obesity, aging and genetic abnormalities. In particular, age can be a factor in OA incidence wherein >50% of arthritis cases are observed in dogs aged between 8-13 years. The musculoskeletal diseases are very common in geriatric patients, and nearly 20% of elderly dogs show orthopedic disorders. In Labrador Retrievers aged >8 years, OA in several joints (elbow, shoulder, hip, knee) is typical. Additionally the size of the canine plays a role in OA onset as well. 45% of dogs with arthritis are large breed dogs. Among these, >50% are giant breed dogs, while only 28% are medium breed dogs and 27% are small breed dogs. The need for pharmaceutical intervention for the alleviation of OA pain in canines is very high.

As stated herein, elevated levels of NGF are indicative of a NGF related disorder, particularly in OA. Elevated levels of NGF have been reported in transgenic arthritic mice along with an increase in the number of mast cells (Aloe, et al., *Int. J. Tissue Reactions-Exp. Clin. Aspects* 15:139-143 (1993)). PCT Publication No. WO 02/096458 discloses use of anti NGF antibodies of certain properties in treating various NGF related disorders such as inflammatory condition (e.g., rheumatoid arthritis). It has been reported that a purified anti-NGF antibody injected into arthritic transgenic mice carrying the human tumor necrosis factor gene caused reduction in the number of mast cells, as well as a decrease in histamine and substance P levels within the synovium of arthritis mice (Aloe et al., *Rheumatol. Int.* 14: 249-252 (1995)). It has been shown that exogenous administration of an NGF antibody reduced the enhanced level of TNFα, occurring in arthritic mice (Marmi et al., *Rheumatol. Int.* 18: 97-102 (1998)). Rodent anti-NGF antagonist antibodies have been reported. See, e.g., Hongo et al., *Hybridoma* (2000) 19(3): 215-227; Ruberti et al. (1993) Cell. Molec. Neurobiol. 13(5): 559-568. However, when rodent antibodies are used therapeutically in non-murine mammals, an anti-murine antibody response develops in significant numbers of treated individuals. Thus, there is a serious need for anti-NGF antagonist antigen binding proteins, including anti-NGF antagonist antibodies of the present invention for canine use particularly for use in treating OA.

While the properties of antibodies make them very attractive therapeutic agents, there are a number of limitations. The vast majority of monoclonal antibodies (mAbs) are of rodent origin, as previously noted. When such antibodies are administered in a different species, patients can mount their own antibody response to such xenogenic antibodies. Such response may result in the eventual neutralization and elimination of the antibody. As described above mice are used extensively in the production of monoclonal antibodies. One problem in the use of using antibodies produced by a particular species, generally initially in the mouse, is that a non-murine subjects being treated with said antibodies react to the mouse antibodies as if they were a foreign substance thus creating a new set of antibodies to the mouse antibodies. Mouse antibodies are "seen" by the non-murine, for example canine, immune system as foreign, and the subject then mounts an immune response against the molecule. Those skilled in the field will recognize the need to be able to treat a subject with an antigen specific antibody, but have that antibody species specific. Part of the reaction generated from cross species antibody administration, for example a mouse monoclonal antibody being administered to a canine, can range from a mild form, like a rash, to a more extreme and life-threatening response, such as renal failure. This immune response can also decrease the effectiveness of the treatment, or create a future reaction if the subject is given a subsequent treatment containing mouse antibodies. Accordingly, we set forth to overcome this disadvantage by "caninization" of an antibody. In particular, this process focuses on the framework regions of the immunoglobulin variable domain, but could also include the compliment determinant regions (CDR's) of the variable domain. The enabling steps and reduction to practice for this process are described in this disclosure.

The process of modifying a monoclonal antibody from an animal to render it less immunogenic for therapeutic administration to species has been aggressively pursued and has been described in a number of publications (e.g. Antibody Engineering: A practical Guide. Carl A. K. Borrebaeck ed. W. H. Freeman and Company, 1992). However, this process has not been applied for the development of therapeutic or diagnostics for non-humans, particularly canines, until recently. In fact, very little has been published with regard to canine variable domains at all. Wasserman and Capra, Biochem. 6, 3160 (1977), determined the amino acid sequence of the variable regions of both a canine IgM and a canine IgA heavy chain. Wasserman and Capra, *Immunochem.* 15, 303 (1978), determined the amino acid sequence of the K light chain from a canine IgA. McCumber and Capra, *Mol. Immunol.* 16, 565 (1979), disclose the complete amino-acid sequence of a canine mu chain. Tang et al., *Vet. Immunology Immunopathology* 80, 259 (2001), discloses a single canine IgG-A γ chain cDNA and four canine IgG-A γ chain protein sequences. It describes PCR amplification of a canine spleen cDNA library with a degenerate oligonucleotide primer designed from the conserved regions of human, mouse, pig, and bovine IgGs. The paucity of information available on canine antibodies has prevented their development as therapeutics for the treatment canine disease.

These noted limitations have prompted the development of engineering technologies known as "speciation" and is well known to those in the art in terms of "humanization" of therapeutic antibodies. Humanized antibodies can be generated as chimeric antibodies or fragments thereof which contain minimal sequence derived from non-human immunoglobulin. For the most part, humanized antibodies are human antibodies (i.e. "recipient antibody" or "target species antibody") in which residues from a complementarity determining region (CDR) of the recipient are replaced by residues from a CDR of a non-human species (i.e. "donor antibody" or "originating species antibody") such as mouse, having the desired. properties such as specificity, affinity, and potency. In some instances, framework region (FR) residues of the human immunoglobulin are replaced by corresponding non-human residues. This humanization strategy is referred to as "CDR grafting" as reported for the making of humanized antibodies (Winter, U.S. Pat. No. 5,225,539). Back mutation of selected target framework residues to the corresponding donor residues might be required to restore and or improved affinity. Structure-based methods may also be employed for humanization and affinity maturation, for example as described for humanization in U.S. patent application Ser. No. 10/153,159 and related applications. Comparison of the essential framework residues required in humanization of several antibodies, as well as computer modeling based on antibody crystal structures revealed a set of framework residues termed as "Vernier zone residues" (Foote, *J. Mol. Biol.* 224:487-499 (1992)). In addition, several residues in the VH-VL interface zone have been suggested to be important in maintaining affinity for the antigen (Santos, *Prog Nucleic Acid Res Mol Biol.* 60: 169-94 (1998); Kettleborough, et al., *Protein Engin.,* 4:773-783 (1991)). Similar strategies for "caninization" of antibodies for use in dogs are described in U.S. Pat. No. 7,261,890.

Alternatively, humanized antibodies may contain the CDRs from a non-human sequence grafted into pools (e.g.

libraries) of individual human framework regions. This newly engineered antibody is able to bind to the same antigen as the original antibody. The antibody constant region is derived from a human antibody. The methodology for performing this aspect is generally described as framework shuffling (Dall'Acqua, *Methods,* 36:43-60 (2005)). Furthermore, the humanized antibody may contain sequences from two or more framework regions derived from at least two human antibody germline sequences with high homology to the donor species. Antibodies designed using this method are described as hybrid antibodies (Rother et al., U.S. Pat. No. 7,393,648) and may be applicable to speciation outside of humanization, for example for caninization.

The approaches described above utilize essentially entire framework regions from one or more antibody variable heavy chains or variable light chains of the target species which are engineered to receive CDRs from the donor species. In some cases, back mutation of selected residues in the variable region is used to enhance presentation of the CDRs. Designing antibodies that minimize immunogenic reaction in a subject to non-native sequences in the antibody, while at the same time preserving antigen binding regions of the antibody sufficiently to maintain efficacy, has proven challenging.

Another challenge for developing therapeutic antibodies targeting proteins is that epitopes on the homologous protein in a different species are frequently different, and the potential for cross-reactivity with other proteins is also different. As a consequence, antibodies have to be made, tested and developed for the specific target in the particular species to be treated.

Antibodies target an antigen through its binding of a specific epitope on an antigen by the interaction with the variable region of the antibody molecule. Furthermore, antibodies have the ability to mediate, inhibit (as in the case of the antagonistic anti-NGF antigen binding protein of the present invention) and/or initiate a variety of biological activities. There are a wide range of functions for therapeutic antibodies, for example, antibodies can modulate receptor-ligand interactions as agonists or antagonists. Antibody binding can initiate intracellular signaling to stimulate cell growth, cytokine production, or apoptosis. Antibodies can deliver agents bound to the Fe region to specific sites. Antibodies also elicit antibody-mediated cytotoxicity (ADCC), complement-mediated cytotoxicity (CDC), and phagocytosis. There are also antibodies that have been altered where the ADCC, CDC, C1q binding and phagocytosis functions have been eliminated. In one embodiment of the present invention the antibody of the present invention comprises alterations in the Fc region of the antibody that alters effector function of said antibody.

Caninization

As used herein, "caninized antibody" means an antibody having an amino acid sequence corresponding to that of an antibody produced by a canine and/or has been made using any of the techniques known in the art or disclosed herein. This definition of a caninized antibody includes antibodies comprising at least one canine heavy chain polypeptide or at least one canine light chain polypeptide. "Speciation", per se, of antibodies, and in particular the humanization of antibodies is a field of study well known to one skilled in the art. It has been unknown until recently whether the speciation of antibodies beyond humanization would yield a therapeutic antibody that could be efficacious in any other species. The present invention exemplifies the caninization of an anti-NGF antibody for therapeutic use in dogs.

Chimeric antibodies comprise sequences from at least two different species. As one example, recombinant cloning techniques may be used to include variable regions, which contain the antigen-binding sites, from a non-canine antibody (i.e., an antibody prepared in a non-canine species immunized with the antigen) and constant regions derived from a canine immunoglobulin.

Caninized antibodies are a type of chimeric antibody wherein variable region residues responsible for antigen binding (i.e., residues of a complementarity determining region, abbreviated complementarity determining region, or any other residues that participate in antigen binding) are derived from a non-canine species, while the remaining variable region residues (i.e., residues of the framework regions) and constant regions are derived, at least in part, from canine antibody sequences. A subset of framework region residues and constant region residues of a caninized antibody may be derived from non-canine sources. Variable regions of a caninized antibody are also described as caninized (i.e., a caninized light or heavy chain variable region). The non-canine species is typically that used for immunization with antigen, such as mouse, rat, rabbit, non-human primate, or other non-canine mammalian species.

Complementarity determining regions (CDRs) are residues of antibody variable regions that participate in antigen binding. Several numbering systems for identifying CDRs are in common use. The Kabat definition is based on sequence variability, and the Clothia definition is based on the location of the structural loop regions. The AbM definition is a compromise between the Kabat and Clothia approaches. A caninized antibody of the invention may be constructed to comprise one or more CDRs. Still further, CDRs may be used separately or in combination in synthetic molecules such as SMIPs and small antibody mimetics.

Framework residues are those residues of antibody variable regions other than hypervariable or CDR residues. Framework residues may be derived from a naturally occurring canine antibody, such as a canine framework that is substantially similar to a framework region of the antibody of the invention. Artificial framework sequences that represent a consensus among individual sequences may also be used. When selecting a framework region for caninization, sequences that are widely represented in canines may be preferred over less populous sequences. Additional mutations of the canine framework acceptor sequences may be made to restore murine residues believed to be involved in antigen contacts and/or residues involved in the structural integrity of the antigen-binding site, or to improve antibody expression.

Grafting of CDRs is performed by replacing one or more CDRs of an acceptor antibody (e.g., a caninized antibody or other antibody comprising desired framework residues) with CDRs of a donor antibody (e.g., a non-canine antibody). Acceptor antibodies may be selected based on similarity of framework residues between a candidate acceptor antibody and a donor antibody. For example, canine framework regions are identified as having substantial sequence homology to each framework region of the relevant non-canine antibody, and CDRs of the non-canine antibody are grafted onto the composite of the different canine framework regions.

Analysis of the three-dimensional structures of antibody-antigen complexes, combined with analysis of the available amino acid sequence data may be used to model sequence variability based on structural dissimilarity of amino acid residues that occur at each position within the CDR. CDRs of the present invention can also be utilized in small antibody mimetics, which comprise two CDR regions and a framework region (Qui et al. Nature Biotechnology Vol 25; 921-929; August 2007).

Acceptor frameworks for grafting of CDRs or abbreviated CDRs may be further modified to introduce desired residues. For example, acceptor frameworks may comprise a heavy chain variable region of a canine consensus sequence, optionally with non-canine donor residues at one or more of positions. Following grafting, additional changes may be made in the donor and/or acceptor sequences to optimize antibody binding and functionality. See e.g., International Publication No. WO 91/09967.

The present invention further provides cells and cell lines expressing antibodies of the invention. Representative host cells include bacterial, yeast, mammalian and human cells, such as CHO cells, HEK-293 cells, HeLa cells, CV-1 cells, and COS cells. Methods for generating a stable cell line following transformation of a heterologous construct into a host cell are known in the art. Representative non-mammalian host cells include insect cells (Potter et al. (1993) Int. Rev. Immunol. 10(2-3):103-112). Antibodies may also be produced in transgenic animals (Houdebine (2002) Curr. Opin. Biotechnol. 13(6):625-629) and transgenic plants (Schillberg et al. (2003) Cell Mol. Life Sci. 60(3):433-45).

As discussed above, monoclonal, chimeric and caninized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others. In one embodiment of the present invention the antibody of the invention comprises an altered Fc region that alters effector function of the antibody.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference).

For example, it is possible to alter the affinity of an Fc region of an antibody for an FcR (e.g., Fc.gamma.R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821). The antibody or binding fragment thereof may be conjugated with a cytotoxin, a therapeutic agent, or a radioactive metal ion. In one embodiment, the protein that is conjugated is an antibody or fragment thereof. A cytotoxin or cytotoxic agent includes any agent that is detrimental to cells. Non-limiting examples include, calicheamicin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and analogs, or homologs thereof. Therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP), cisplatin), anthracyclines (e.g., daunorubicin and doxorubicin), antibiotics (e.g., dactinomycin, bleomycin, mithramycin, and anthramycin), and anti-mitotic agents (e.g., vincristine and vinblastine). Techniques for conjugating such moieties to proteins are well known in the art.

Compositions, Derived Compositions, and Methods of Making the Compositions

This invention encompasses compositions, including pharmaceutical compositions, comprising antibodies, polypeptides and polynucleotides comprising sequences encoding antibodies or polypeptides of the invention.

As used herein, compositions comprise one or more antibodies, antigen binding proteins or polypeptides (which may or may not be an antibody) that bind to canine NGF, and/or one or more polynucleotides comprising sequences encoding one or more antibodies or polypeptides that bind to NGF. These compositions may further comprise suitable excipients, such as pharmaceutically acceptable excipients including buffers, which are well known in the art. The invention also encompasses isolated antibody, polypeptide and polynucleotide embodiments. The invention also encompasses substantially pure antibody, polypeptide and polynucleotide embodiments.

In some embodiments, the present invention provides for novel caninized monoclonal antibodies that specifically bind to canine NGF. In one embodiment, a monoclonal antibody of the invention binds to NGF and prevents its binding to, and activation of, its receptors Trk A and to a lesser extent p75, thus preventing the signaling cascade as described herein. The monoclonal antibodies of the present invention are identified herein as "SM57", "SM58", "SM66", "CanE3M65-12" and "CANSSM-QC23-VL/CANSSM57-VH" ("SSMQC23HCLC")

In one or more embodiments, the present invention provides an isolated caninized antigen binding protein wherein the variable light chain comprises SEQ ID NO. 16 (CAN-E3M-VL) and the variable heavy chain comprises SEQ ID NO. 17 (CAN-N2G9-VH).

In one or more embodiments, the present invention provides an isolated caninized antigen binding protein comprising a variable light chain comprising SEQ ID NO. 26 (CAN-SSME3M-VL) and the variable heavy chain comprising SEQ ID NO. 27 (CAN-SSM57-VH).

In one or more embodiments, the present invention provides an isolated caninized antigen binding protein comprising a variable light chain comprising SEQ ID NO. 30 (CAN-QC23-VL) and a variable heavy chain comprising SEQ ID NO. 27 (CAN-SSM57-VH).

A further embodiment of the invention provides the nucleic acids that encode the various antigen binding proteins as previously described.

The present invention provides for recombinant monoclonal antibodies and peptides and their uses in clinical administrations and scientific procedures, including diagnostic procedures. With the advent of methods of molecular biology and recombinant technology, it is possible to produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as H2L2 and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or 'V' regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

The present invention further provides a vector including at least one of the nucleic acids described above. Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an anti-NGF antibody or portion. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding anti-NGF sequences can be identified. It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-NGF antibodies or peptides.

For example, one class of substitutions is conservative amino acid substitutions. Such substitutions are those that substitute a given amino acid in an anti-NGF antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-NGF antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W. H. Freeman & Co., N.Y., 1993). Many detailed reviews are available on this subject, such as by Wold, Posttranslational Covalent Modification of proteins, 1-12 (Johnson, ed., Academic Press, N.Y., 1983); Seifter et al. 182 Meth. Enzymol. 626-46 (1990); and Rattan et al. 663 Ann. NY Acad. Sci. 48-62 (1992).

Accordingly, the antibodies and peptides of the present invention also encompass derivatives or analogs in which a substituted amino acid residue is not one encoded by the genetic code. Similarly, the additions and substitutions in the amino acid sequence as well as variations, and modifications just described may be equally applicable to the amino acid sequence of the NGF antigen and/or epitope or peptides thereof, and are thus encompassed by the present invention. As mentioned above, the genes encoding a monoclonal antibody according to the present invention is specifically effective in the recognition of NGF.

Antibody Derivatives

Included within the scope of this invention are antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (251,1311), carbon (4C), sulfur (35S), indium, tritium ($H^3$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. No. 20030031671.

Recombinant Expression of Antibodies

In some embodiments, the nucleic acids encoding a subject monoclonal antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing. Traditionally, monoclonal antibodies have been produced as native molecules in murine hybridoma lines. In addition to that technology, the present invention provides for recombinant DNA expression of monoclonal antibodies. This allows the production of caninized antibodies, as well as a spectrum of antibody derivatives and fusion proteins in a host species of choice.

A nucleic acid sequence encoding at least one anti-NGF antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, NY, 1982 and 1989), and Ausubel et al. 1993 supra, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-NGF peptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an anti-NGF antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

In one embodiment, the nucleotide sequence of the invention will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli (such as, for example, pBR322, CoIE1, pSC101, pACYC 184, .pi.vX). Such plasmids are, for example, disclosed by Maniatis et aI., 1989 supra; Ausubel et al, 1993 supra.

Bacillus plasmids include pC194, pC221, pT127, etc. Such plasmids are disclosed by Gryczan, in THE MOLEC. BIO. OF THE BACILLI 307-329 (Academic Press, NY, 1982). Suitable *Streptomyces* plasmids include p1J101 (Kendall et al., 169 J. Bacteriol. 4177-83 (1987), and *Streptomyces* bacteriophages such as phLC31 (Chater et al., in SIXTH INT'L SYMPOSIUM ON ACTINOMYCETALES BIO. 45-54 (Akademiai Kaido, Budapest, Hungary 1986). Pseudomonas plasmids are reviewed in John et aI., 8 Rev. Infect. Dis. 693-704 (1986); lzaki, 33 Jpn. J. Bacteriol. 729-42 (1978); and Ausubel et aI., 1993 supra.

Alternatively, gene expression elements useful for the expression of cDNA encoding anti-NGF antibodies or peptides include, but are not limited to (a) viral transcription promoters and their enhancer elements, such as the SV40 early promoter (Okayama et aI., 3 Mol. Cell. Biol. 280 (1983), Rous sarcoma virus LTR (Gorman et aI., 79 Proc. Natl. Acad. Sci., USA 6777 (1982), and Moloney murine leukemia virus LTR (Grosschedl et aI., 41 Cell 885 (1985); (b) splice regions and polyadenylation sites such as those derived from the SV40 late region (Okayarea et aI., 1983), and (c) polyadenylation sites such as in SV40 (Okayama et aI., 1983).

Immunoglobulin cDNA genes can be expressed as described by Weidle et aI., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements. For immunoglobulin genes comprised of part cDNA, part genomic DNA (Whittle et aI., 1 Protein Engin. 499 (1987>, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with an anti-NGF peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-NGF peptide or chimeric H and L chains, or portions thereof are assembled in separate expression vectors that are then used to cotransfect a recipient cell. Alternatively the fused genes encoding the chimeric H and L chains can be assembled on the same expression vector. For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of human or nonhuman origin, hybridoma cells of human or non-human origin, or interspecies heterohybridoma cells.

The expression vector carrying a chimeric, caninized antibody construct or anti-NGF polypeptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et at, 240 Science 1538 (1988).

Yeast can provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of anti-NGF peptides, antibody and assembled murine and chimeric, heterochimeric, caninized, antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.,) IRL Press, Oxford, UK 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine, chimeric, heterochimeric, caninized antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, N.Y. (1994-2001); Colligan et al., eds. Current Protocols in Protein Science, John Wiley & Sons, NY, N.Y. (1997-2001).

Host mammalian cells may be grown in vitro or in vivo. Mammalian cells provide posttranslational modifications to immunoglobulin protein molecules including leader peptide removal, folding and assembly of Hand L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Many vector systems are available for the expression of cloned anti-NGF peptides Hand L chain genes in mammalian cells (see Glover, 1985 supra). Different approaches can be followed to obtain complete H2L2 antibodies. It is possible to co-express Hand L chains in the same cells to achieve intracellular association and linkage of H and L chains into complete tetrameric H2L2 antibodies and/or anti-NGF peptides. The co-expression can occur by using either the same or different plasmids in the same host. Genes for both Hand L chains and/or anti-NGF peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. cell lines producing anti-NGF peptides and/or H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Pharmaceutical and Veterinary Applications

The anti-NGF antibodies or peptides of the present invention can be used for example in the treatment of NGF related disorders in dogs. More specifically, the invention further provides for a pharmaceutical composition comprising a pharmaceutically acceptable carrier or diluent and, as active ingredient, an antibody or peptide according to the invention. The antibody can be a chimeric, heterochimeric, caninized, or antibody according to the present invention. Intact immunoglobulins or their binding fragments, such as Fab, are also envisioned. The antibody and pharmaceutical compositions thereof of this invention are useful for parenteral administration, e.g., subcutaneously, intramuscularly or intravenously.

Anti-NGF antibodies and/or peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice. Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed.

In some desired embodiments, the antibodies are administered by parenteral injection. For parenteral administration, anti-NGF antibodies or peptides can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate. The compositions containing the present antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art. In therapeutic application, compositions are administered to a subject already suffering from a disease, in an amount sufficient to cure or at least partially arrest or alleviate the disease and its complications. An amount adequate to accomplish this is defined as a "therapeutically effective dose" or a "therapeutically effective amount". Amounts effective for this use will depend upon the severity of the disease and the general state of the subject's own immune system, but generally range from about 0.1 mg antibody per kg body weight to about 10 mg antibody per kg body weight, preferably about 0.3 mg antibody per kg of body weight to about 5 mg of antibody per kg of body weight. In view of the minimization of extraneous substances and the lower probability of "foreign substance" rejections which are achieved by the present canine-like and antibodies of this invention, it may be possible to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms kind of concurrent treatment, frequency of treatment, and the effect desired.

As a non-limiting example, treatment of NGF-related pathologies in dogs can be provided as a biweekly or monthly dosage of anti-NGF antibodies of the present invention in the dosage range described above. Example antibodies for canine therapeutic use are high affinity (these may also be high avidity) antibodies, and fragments, regions and derivatives thereof having potent in vivo anti-NGF activity, according to the present invention. Single or multiple administrations of the compositions can be carried out with dose levels and pattern being selected by the treating veterinarian. In any event, the pharmaceutical formulations should provide a quantity of the antibody(ies) of this invention sufficient to effectively treat the subject.

Diagnostic Applications

The present invention also provides the above anti-NGF antibodies and peptides for use in diagnostic methods for detecting NGF in canines known to be or suspected of having an NGF related disorder. In an embodiment of the invention the NGF related disorder is pain. In another embodiment the NGF related disorder is osteoarthritis Anti-NGF antibodies and/or peptides of the present invention are useful for immunoassays which detect or quantitate NGF, or anti-NGF antibodies, in a sample. An immunoassay for NGF typically comprises incubating a clinical or biological sample in the presence of a detectably labeled high affinity (or high avidity) anti-NGF antibody or polypeptide of the present invention capable of selectively binding to NGF, and detecting the labeled peptide or antibody which is bound in a sample. Various clinical assay procedures are well known in the art. See, ex. IMMUNOASSAYS FOR THE 80'S (Voller et al., eds., Univ. Park, 1981). Such samples include tissue biopsy, blood, serum, and fecal samples, or liquids collected from animal subjects and subjected to ELISA analysis as described below. Thus, an anti-NGF antibody or polypeptide can be fixed to nitrocellulose, or another solid support which is capable of immobilizing cells, cell particles or soluble proteins. The support can then be washed with suitable buffers followed by treatment with the detectably labeled NGF specific peptide, antibody or antigen binding protein. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to NGF or an anti-NGF antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation. Well known method steps can determine binding activity of a given lot of anti-NGF peptide and/or antibody or antigen binding protein. Those skilled in the art can determine operative and optimal assay conditions by routine experimentation.

Detectably labeling an NGF-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the NGF-specific antibodies of the present invention include, but are not limited to, malate dehydrogenase, staphylococcal nuclease, delta)-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. By radioactively labeling the NGF-specific antibodies, it is possible to detect NGF through the use of a radioimmunoassay (RIA). See Work et al., LAB. TECHNIQUES & BIOCHEM. IN MOLEC. BIO(No. Holland Pub. Co., NY, 1978). The radioactive isotope can be detected by such means as the use of a gamma counter or a scintillation counter or by autoradiography. Isotopes which are particularly useful for the purpose of the present invention include: $^3$H, $^{125}$I, $^{131}$I, $^{35}$S, and $^{14}$C.

It is also possible to label the NGF-specific antibodies with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The NGF-specific antibodies or antigen binding proteins can also be delectably labeled using fluorescence-emitting metals such a $^{125}$Eu, or others of the lanthanide series. These metals can be attached to the NGF specific antibody using such metal chelating groups as diethylenetriaminepentaacetic acid (DTPA) or ethylenediamine-tetraacetic acid (EDTA).

The NGF-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the NGF-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the NGF-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the NGF which is detected by the above assays can be present in a biological sample. Any sample containing NGF may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from an animal subject, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of NGF but also the distribution of NGF in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid phase antibody, antigen, and labeled antibody.

The antibodies may be used to quantitatively or qualitatively detect the NGF in a sample or to detect presence of cells that express the NGF. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the antibody, such as antibodies specific for canine immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art. Importantly, the antibodies of the present invention may be helpful in diagnosing an NGF related disorder in canines. More specifically, the antibody of the present invention may identify the overexpression of NGF in companion animals. Thus, the antibody of the present invention may provide an important immunohistochemistry tool. The antibodies of the present invention may be used on antibody arrays, highly suitable for measuring gene expression profiles.

Kits

Also included within the scope of the present invention are kits for practicing the subject methods. The kits at least include one or more of the antibodies of the present invention, a nucleic acid encoding the same, or a cell containing the same. An antibody of the present invention may be provided, usually in a lyophilized form, in a container. The antibodies, which may be conjugated to a label or toxin, or unconjugated, are typically included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about, 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

The invention will now be described further by the non-limiting examples below.

EXAMPLES

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

Example 1

Identification of Mouse Monoclonal Antibody Recognizing Canine Nerve Growth Factor (NGF)

A series of murine mAbs were produced against mature, human ß-NGF (U.S. Pat. No. 7,727,527). Once these mAbs were generated, they were subjected to a variety of analyses, including epitope mapping and in vitro tests for 1) binding to NGF and 2) ability to block binding of NGF to its receptors TrkA and to a lesser extent p75 and 3) assessment of functional antagonism associated with NGF blockade (blockade of TrkA autophosphorylation, blockade of NGF-dependent survival of neurons). Based on these results, it was found that mAbs that bind to variable regions 1 (ß-hairpin turn A'→A"), 4 (ß-strands C and D) and the carboxy-terminus are capable of blocking TrkA and p75 binding. Molecular modeling of the binding epitope on NGF of one of these murine mAbs, RN911, is shown in FIG. 6A. RN911 was shown to be efficacious in preclinical rodent models of pain associated with arthritis, cancer, surgical incision as well as neuropathic pain and visceral pain.

Anti-NGF Therapy for Joint Pain in Dogs

Amino acid sequence identity is 100% conserved within the binding epitope of RN911 on B-NGF across dogs, mice and humans (FIG. 6B, above). High affinity binding of RN911 to recombinant canine NGF ($K_D$=755 pM) was experimentally verified and efficacy of the anti-NGF mAb in a canine synovitis pain model that is routinely used by one skilled in the art in evaluating pain models and described below, was evaluated using RN911. RN911 was produced in sufficient quantities using techniques of one skilled in the art, for both pharmacokinetics/toleration and efficacy studies in purpose-bred beagles. An efficacy study was designed that involved induction of synovitis at 3 days and 7 days after IV injection of RN911 and evaluation of lameness/pain at multiple timepoints post-synovitis induction. A pharmacokinetics/toleration study, described in the next section, was performed prior to the efficacy study to gain confidence in the safety of RN911 in beagles and to collect data that would help guide dose selection for the efficacy study.

DMPK

Metabolism and Disposition

As with all proteins, it can be assumed that RN911 is catabolized to amino acids and other endogenous components. Unchanged RN911 is unlikely to be excreted.

Pharmacokinetics

The pharmacokinetics (PK) of murine anti-NGF mAb RN911 in dogs were studied following single IV administration. Three dogs were dosed with placebo, 4 dogs at 1.2 mg/kg, 4 dogs at 3.5 mg/kg, and 1 dog at 9.8 mg/kg. Only one dog was utilized at the highest dose. The pharmacokinetic data exhibited low variability and the similar shape of the profiles of 'free' RN911 at all doses suggested that target-mediated disposition was not a factor in the PK. The data exhibited excellent dose proportionality. $T_{1/2}$ was similar at all doses, averaging 102±27 hours (n=9). Clearance, at 0.00051±0.00005 L/h/kg, was very slow. Volume of distribution, at 0.072±0.021 L/kg, was close to what would be expected for a protein which is confined to the blood volume of the dog. FIG. 7 shows data from serum analysis of markers analyzed from the synovitis efficacy study described below. It is clear that the serum concentrations and pharmacokinetics at 3 mg/kg in the efficacy study were nearly identical to the values at 3.5 mg/kg in the PK study.

Figure 8:
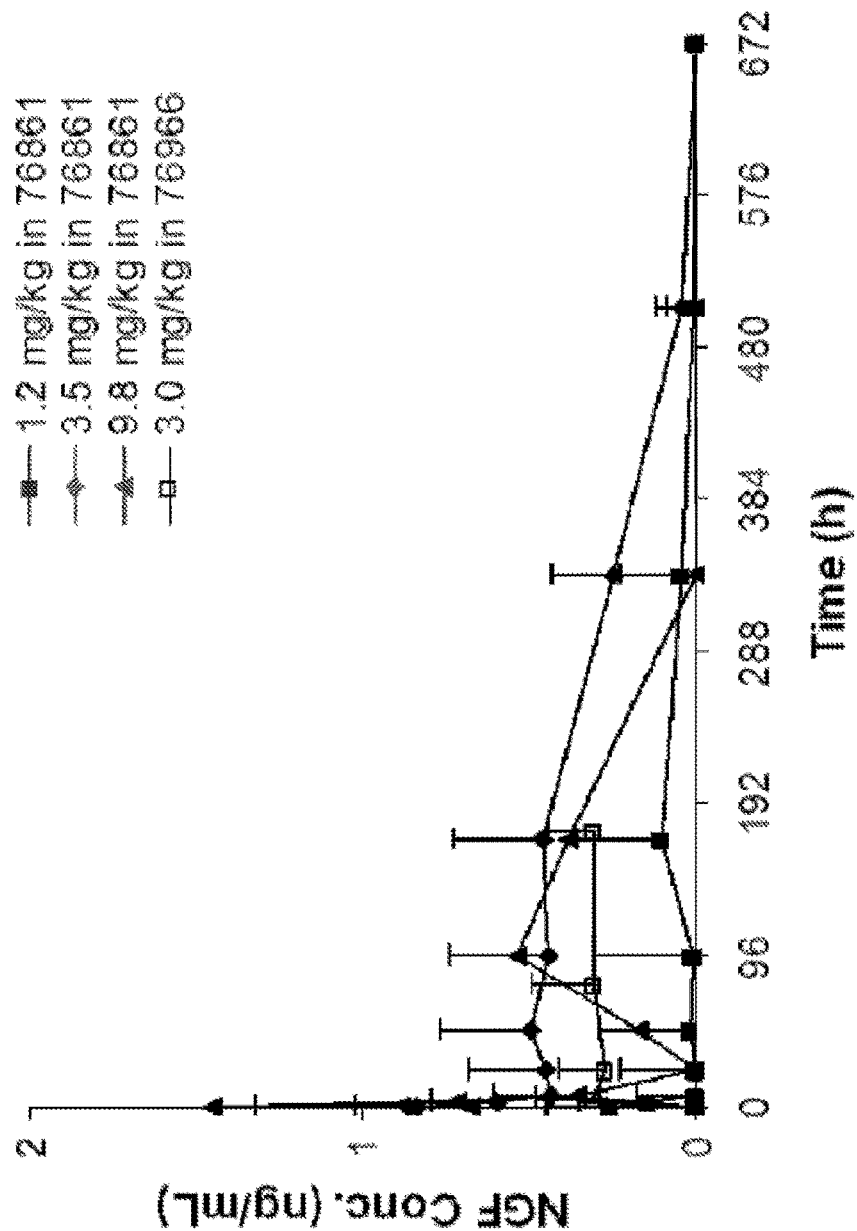

"Bound" RN911 was assayed in both studies using an ELISA method (FIG. 8) The concentrations are reported as NGF-equivalents. The typical RN911-NGF concentrations, which remained near peak levels for at least one week, were approximately 0.5 ng/mL in NGF-equivalents. This is roughly 10-fold higher than endogenous NGF concentrations in canine serum (~40-60 pg/mL).

The typical RN911-NGF serum concentration, when converted to RN911-equivalents, was approximately 5 ng/mL (0.5 ng/mL*molecular weight ratio, 150,000/13,425). This is far below the measured free RN911 concentrations shown in the first figure and suggest that the mAb may remain in excess (as compared with NGF concentrations) for several weeks at doses≥3 mg/kg.

Immunogenicity

Anti-drug antibody (ADA) titers were determined before dosing and at the end of the study. As shown in Table 1, there was evidence of a rise in ADA titers in at least two of the beagles (see dogs 8 and 12). It is not surprising that RN911 would generate an immune response in beagles given that it is a murine mAb; no attempt was made to perform repeated dosing studies with this mAb.

TABLE 1

Table 1. Anti-drug antibody (ADA) titers after IV injection of RN911

| Dog | Dose (mg/kg) | ADA Titer (-fold dilution) Day 0 | Day 28 |
|---|---|---|---|
| Control sample | — | 400 | 800 |
| 1 | 0 | 100 | <50 |
| 2 | 0 | 50 | 50 |
| 3 | 0 | <50 | <50 |
| 5 | 1.2 | 50 | 200 |
| 6 | 1.2 | 50 | 50 |
| 7 | 1.2 | <50 | 50 |
| 8 | 1.2 | 50 | ≥1600 |
| 9 | 3.5 | <50 | 50 |
| 10 | 3.5 | <50 | 200 |
| 11 | 3.5 | <50 | 100 |
| 12 | 3.5 | 50 | 800 |
| 13 | 9.8 | <50 | <50 |

Bioanalytical Assay Methodology

The free RN911 ELISA was based on the use of recombinant canine NGF as the capture agent and peroxidase-conjugated donkey anti-mouse IgG as the detection antibody. QCs as well as standards were included in the assay run.

The bound RN911-NGF ELISA was based on the use of biotinylated rabbit anti-human NGF adsorbed on a strepavidin plate. This antibody captured both NGF-RN911 and free NGF, but the NGF-RN911 was selectively detected using peroxidase-conjugated donkey anti-mouse IgG. Standards were prepared by incubating a known concentration of canine NGF with a slight molar excess of RN911.

The anti-drug antibody ELISA utilized RN911 as the capture agent. ADAs in the dog serum samples were captured on the plate and detected using a mixture of peroxidase-conjugated goat anti-dog antibodies which were able to detect all four canine IgG subclasses.

Pharmacokinetics/Pharmacodynamics (PK/PD)

PK/PD data were generated with RN911 in the target species in a synovitis efficacy study. In the synovitis pain model, transient inflammation of the synovial membrane in a single stifle is induced via intra-articular injection of bacterial lipopolysaccharide (LPS). Quantifiable lameness occurs within 2h of synovitis induction, peaks at 3-4h, is waning by 6h and is fully resolved after 24h. From an IACUC perspective, it is acceptable to induce synovitis on two separate occasions (i.e., once in each stifle), provided the lameness associated with the first synovitis induction has fully resolved. Therefore we designed a study in which synovitis was induced in the same beagle 3 days and 7 days after IV treatment (RN911 or PBS vehicle). After each synovitis induction, lameness was quantified using a visual analogue scale (VAS).

Figure 9:
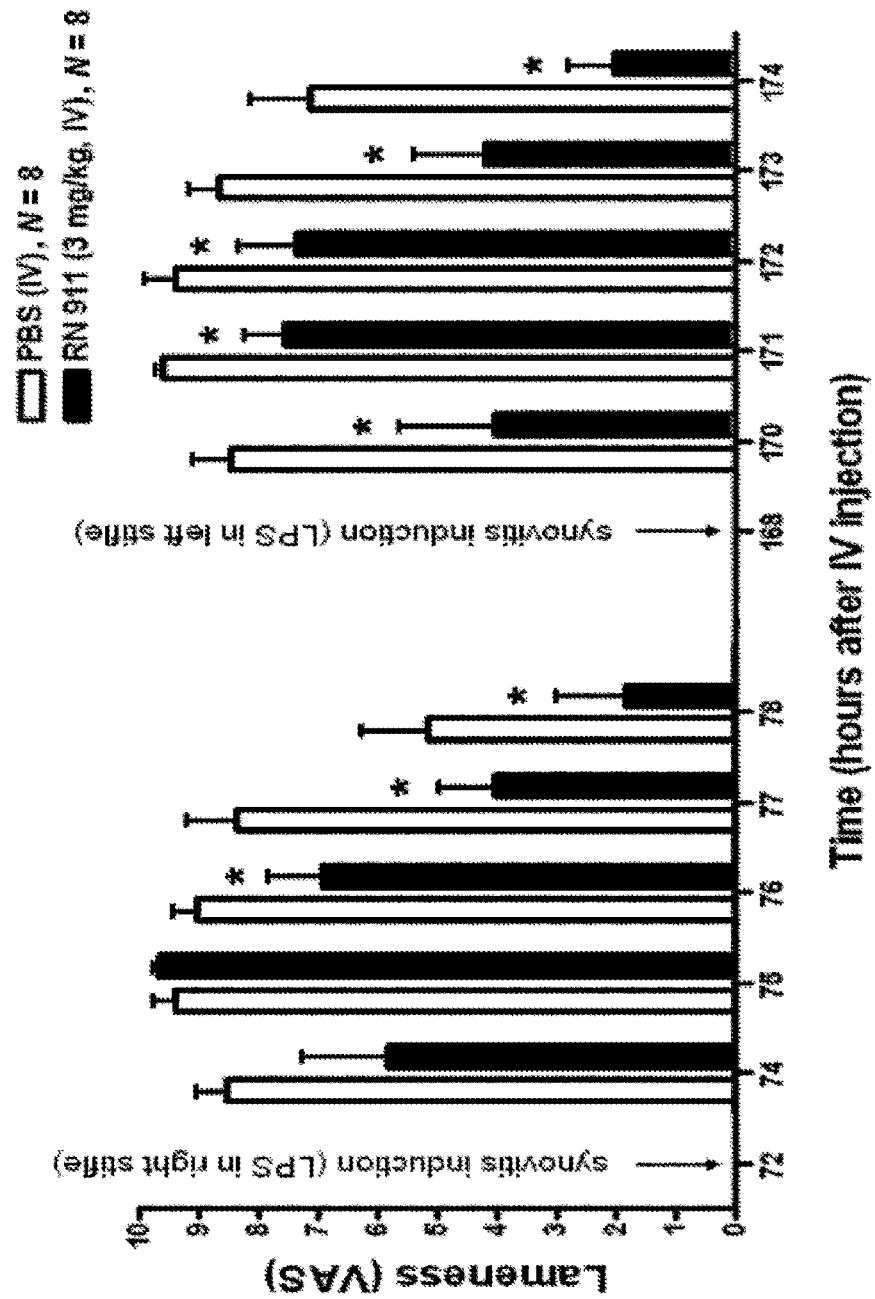

The results of this study show that RN911 (3 mg/kg, IV) caused a statistically significant decrease in synovitis-associated lameness at 3 days after dosing (FIG. 4). At this time, the free RN911 serum concentrations averaged 24400±3900 ng/mL (170±27 nM; FIG. 2). RN911 was even more effective at 7 days (FIG. 9) when the free RN911 serum concentration averaged 13200±3500 ng/mL (91±24 nM; FIG. 7).

Example 2

Caninization Strategy

The generation of anti-drug antibodies (ADAs) can be associated with loss of efficacy for any biotherapeutic protein including monoclonal antibodies. Comprehensive evaluation of the literature has shown that speciation of monoclonal antibodies can reduce the propensity for mAbs to be immunogenic although examples of immunogenic fully human mAbs and non-immunogenic chimeric mAbs can be found. To help mitigate risks associated with ADA formation for the mouse anti-NGF, RN911, monoclonal antibody provided herein, a caninization strategy was employed. This caninization strategy is based on identifying the most appropriate canine germline antibody sequence for CDR grafting (FIG. 3). Following extensive analysis of all available canine germline sequences for both the heavy and light chains, germline candidates were selected on their homology to RN911, and the CDRs from RN911 were used to replace native canine CDRs. The objective was to retain high affinity and cell-based activity using fully canine frameworks to minimize the potential of immunogenicity in vivo. Caninized mAbs were optimized for mammalian expression, expressed and characterized for their ability to bind NGF via SPR. These results are described below in Example 3. Only mAbs that retained both reliable expression levels and the ability to bind NGF following caninization were advanced for further characterization. Those mAbs that did not express transiently or lost the ability to bind NGF were systematically dissected to identify: 1) the chain responsible for loss of function of lack of expression, 2) the framework responsible for the loss of expression or function and 3) the amino acid(s) responsible for loss of expression or function.

Example 3

Caninization of RN911 Antibody

Synthetic constructs representing the caninized variable heavy and light chains of mAb RN911 were made. Following subcloning of each variable chain into plasmids containing the respective canine heavy or kappa constant region, plasmids were co-transfected for antibody expression in HEK 293 cells. The canine heavy chain constant region of the present invention are not limited to any particular subtype, however in some embodiments the canine heavy chain is described as SEQ ID. NO. 45 or SEQ ID NO. 48. The canine kappa light chain constant regions are not limited to any particular sequences, however in some embodiments of the present invention the canine kappa constant region is described as SEQ ID. NO. 47. Frameworks used for mAb "canE3M65" expressed in HEK 293 transient expression system and retained NGF binding upon caninization. (Seq ID NO.33 "CAN-E3M-VL", SEQ ID NO. 34. "CAN-N2G9-VH").

Figure 10:
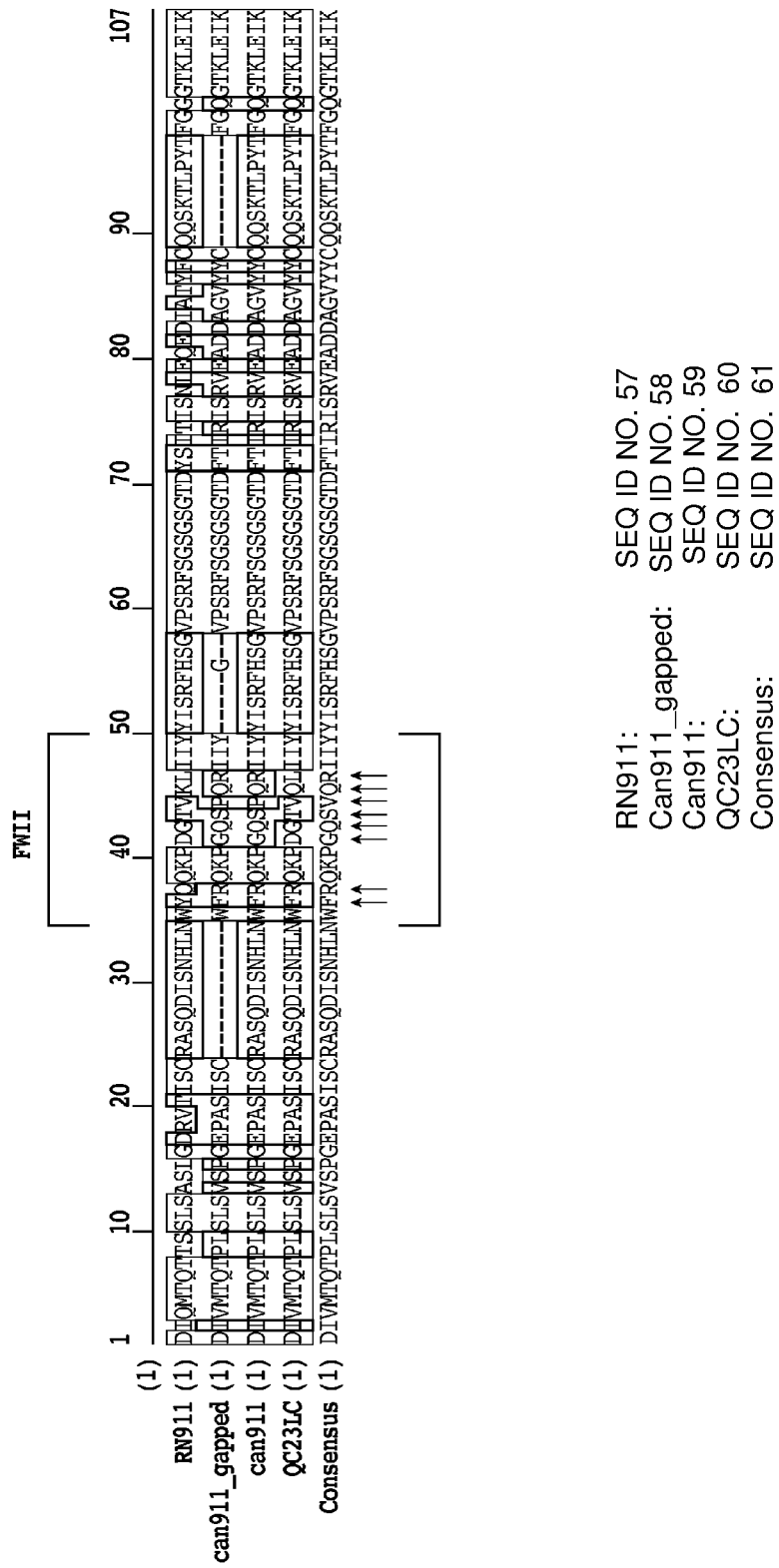

In contrast, the germline sequences used for the can618 (CAN-618-VL; CAN-N2G9-VH) caninization efforts resulted in certain non-expressing mAbs. Chimeric, heterochimeric, and caninized versions of mAb RN911 were expressed and characterized for their ability to bind canine NGF via SPR. These results demonstrated that the caninized antibody did not express. Also, with respect to the heterochimeras, the chimeric heavy chain paired with the caninized light chain lost expression, while the caninized heavy chain paired with the chimeric light chain retained expression in HEK293 cells. Based on the results obtained from the heterochimeras, it was deduced that the caninized light chain was responsible for the loss of expression. In an effort to restore expression of the caninized versions of RN911 in which expression was lost, the caninized light chain was modified by swapping framework sequences. FIG. 10 provides an overview of the can911 light chain framework substitution work. This work identified an antibody replacing residues within the canine framework II (FWII) with mouse framework II sequence and restoring expression in HEK293 cells (SEQ ID NO.35 "CAN-618-VL", SEQ ID NO. 36 "CAN-QC23-VL", and variable heavy chain SEQ ID NO.34 "CAN-N2G9-VH").

Figure 11:
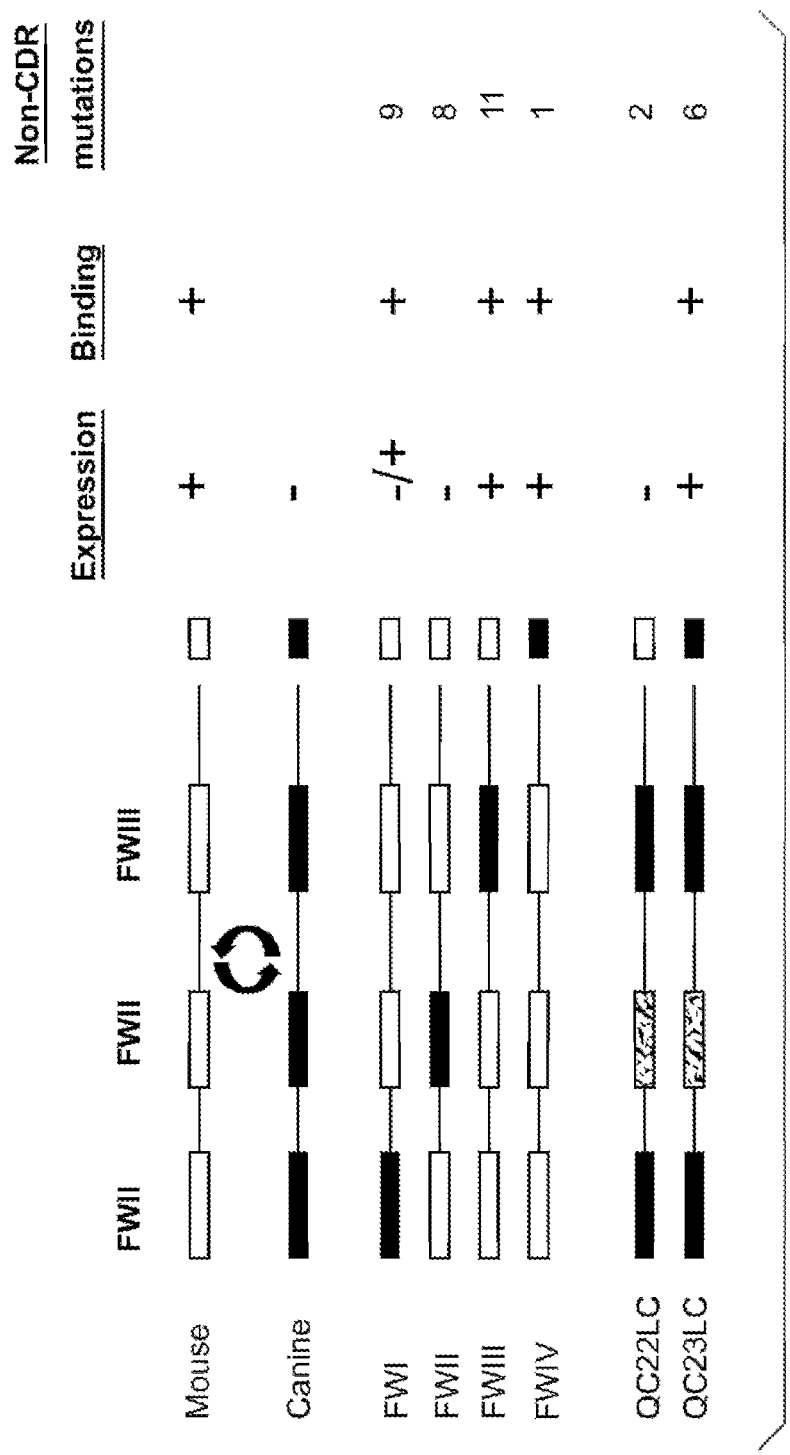

FIG. 11 summarizes the results of both the expression and respective mutations. These data demonstrate that the caninized derivatives using frameworks 3 and 4 both retain HEK expression levels comparable to their precursor molecule and show binding to canine NGF. Framework 1 retained expression to a lesser extent, but also maintained binding to canine NGF.

Example 4

Characterization of Canine NGF Binding to Caninized Anti-NGF mAbs

Figure 12A:
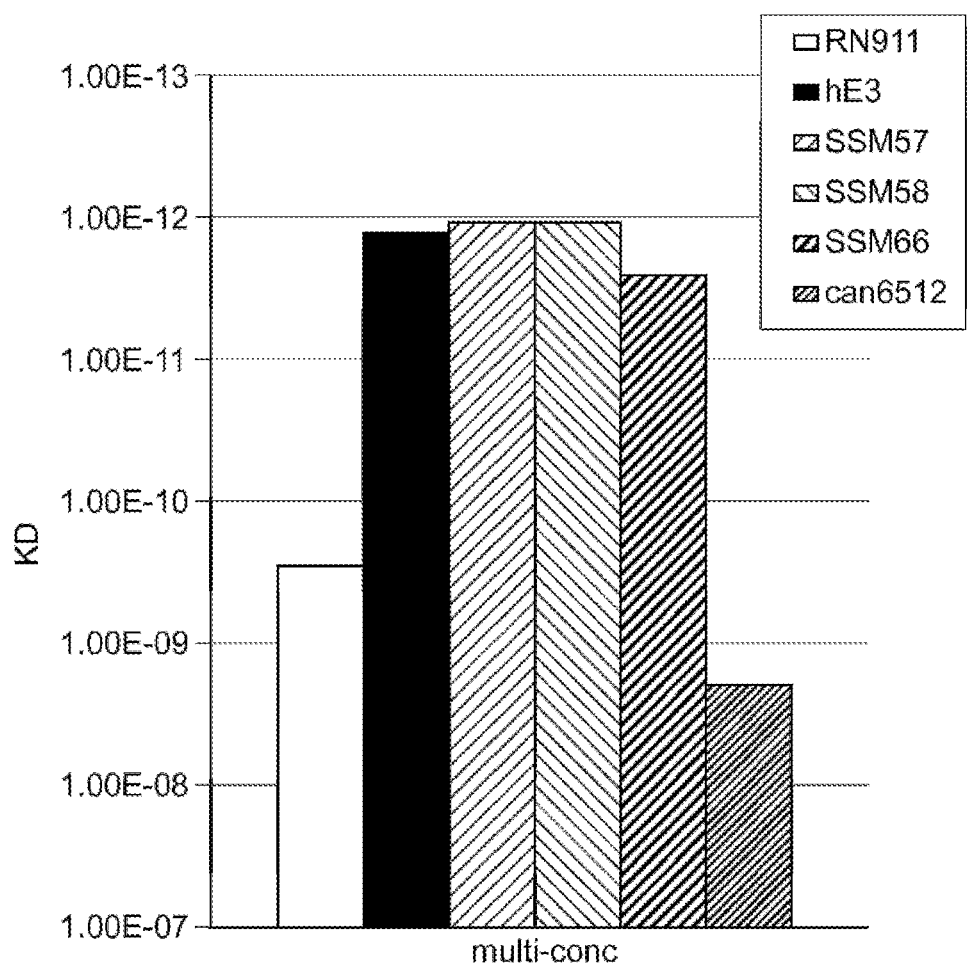
Figure 12B:
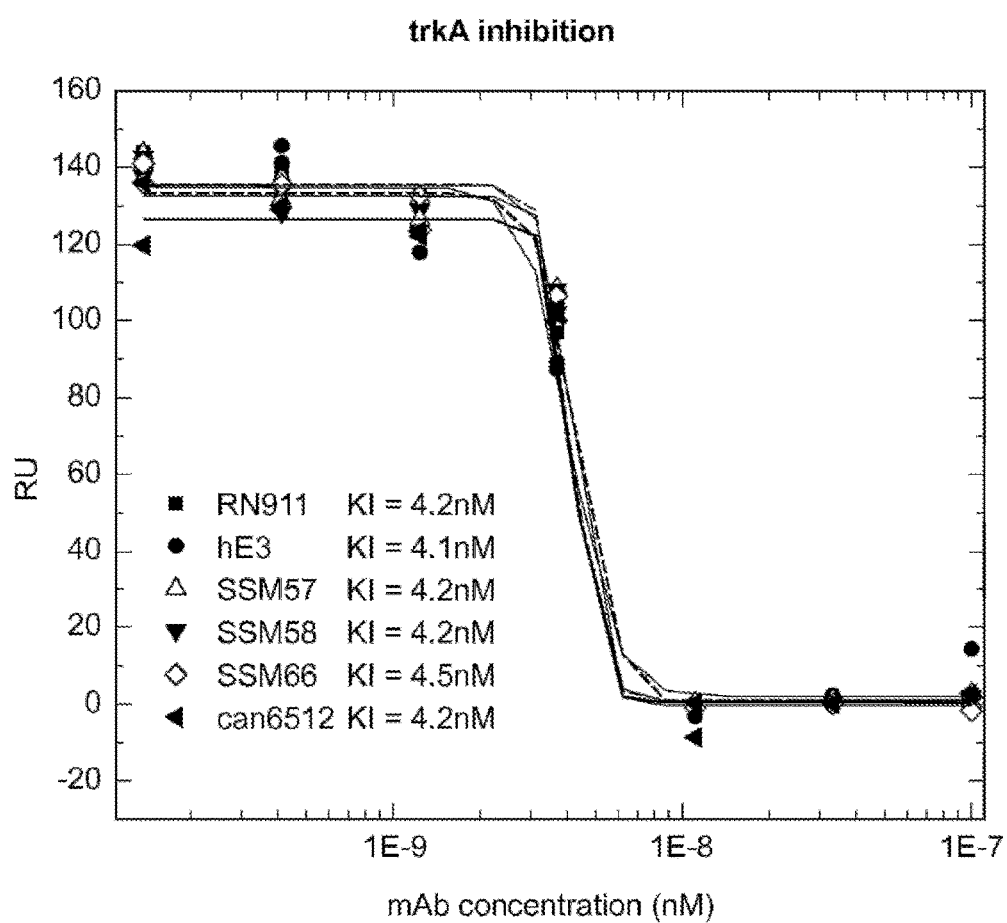
Figure 13:
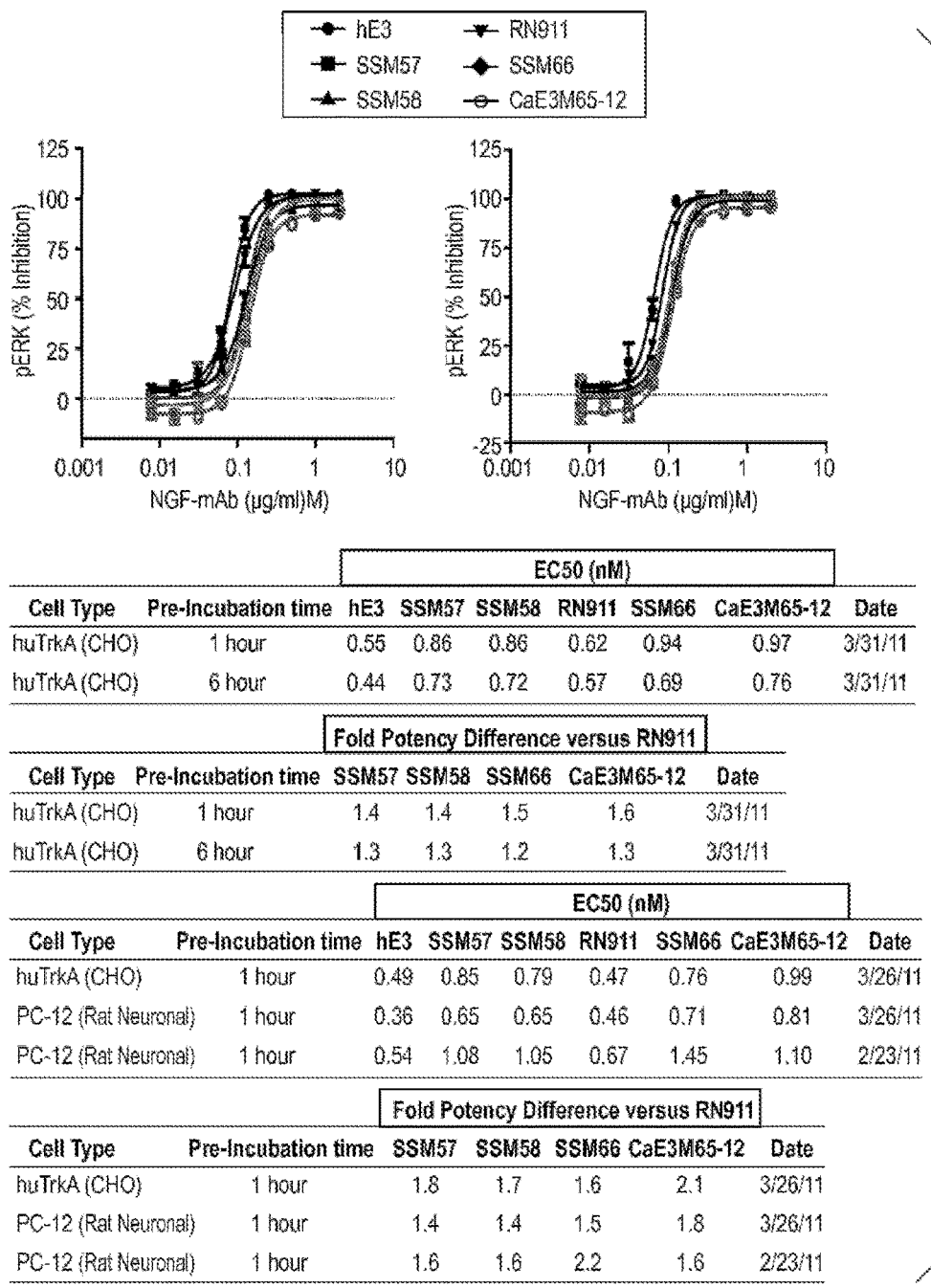

Affinities of each caninized anti-NGF antibody to canine NGF were measured using SPR (Surface Plasmon Resonance). In addition, a functional in vitro assay was developed to measure inhibition constants for the mAbs ability to inhibit binding of NGF to TrkA. Data shown in FIGS. 12 and 13 for can6512 (CAN-N2G9-VH, CAN-E3M-VL, CAN-65E-HC, CAN-KAPPA-LC) and RN911 illustrate high affinity binding of mAbs to NGF and potent inhibition by mAbs of NGF binding to receptor trkA. Some affinity was lost, however, upon caninization to mAb CAN-N2G9-VH, CAN-E3M. Due to this loss of affinity, the caninized mAb was affinity matured (see Example 5 for details) to regain potency. Included in FIGS. 12 and 13 are the results of the affinity matured products, SSM57 (SEQ ID NO. 27 "CAN-SSM57-VH", SEQ ID NO. 26 "CAN-SSME3M-VL"), SSM58 (SEQ ID NO. 28 CAN-SSM58-VH, SEQ ID NO. 26 "CAN-SSME3M-VL"), and SSM66 (SEQ ID NO.29 CAN-SSM66, SEQ ID NO. 26 CAN-SSME3M-VL) on each SPR assay.

Example 5

Affinity Maturation of Caninized Anti-NGF mAb

Figure 15:
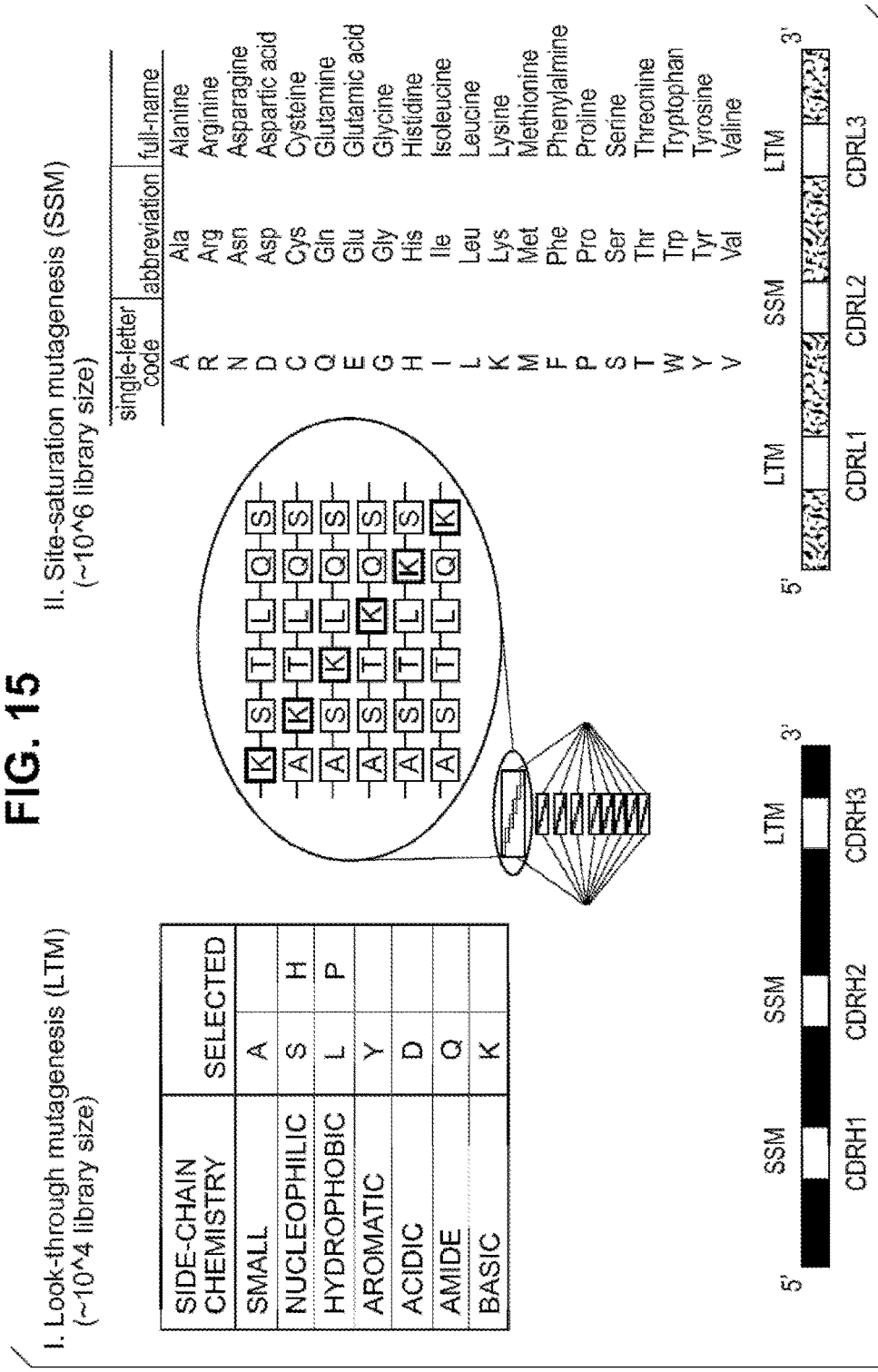

Affinity maturation of canE3M65 (SEQ ID NO. 16 "CAN-E3M-VL", SEQ ID NO. 17 "CAN-N2G9-VH") was necessary to return the affinity of the caninized mAb to that of the progenitor mouse antibody. Two antibody libraries were designed to contain individual point mutations within the antibody sequence in CDR regions only. FIG. 15 outlines the design strategy of each Fab library in which the Look-Through Mutagenesis (LTM) library comprises individual site mutations limited to one of nine representative amino acid residues, while the Site-Saturation Mutagenesis (SSM) library can sample any natural amino acid (Cys and Met were excluded here). The LTM library was constructed to identify beneficial mutations in CDRH3, CDRL1, and CDRL3. Alternatively, the SSM library mutations are located in CDRH1, CDRH2, and CDRL2, allowing us to combine beneficial mutations from each library.

The LTM library was constructed from a series of primers designed using an oligonucleotide design program commonly used by those of skill in the art. PCR products were combined to achieve a Fab library comprised of single mutations on each of the three specified CDRs, as well as combinations including variations on CDRH3, CDRL1, and/or CDRL3. A 93% ligation efficiency was achieved with a library size of ~10^4. Four rounds of panning with decreasing amounts of biotinylated canine NGF were run and extended off-rates were selected for by extended overnight wash steps. Amount of NGF antigen used ranged from 1 ng/µL beads to 10 pg/µL beads and Fabs were eluted using non-biotinylated NGF in excess. After the fourth round of panning, outputs were cloned into a TOPO vector and sequenced. Enriched mutations are shown in Table 2.

Indicated constructs were converted into full IgGs and expressed transiently in HEK293 cells. Results of expression for individual and combined mutations are shown below in Tables 3 and 4

TABLE 3

| # | HC | LC | expression |
|---|-----|-----|------------|
| 1 | N2G9_6512 | E3M | 8.15 |
| 2 | N2G9_6512 | S91Y | 6.04 |
| 3 | N2G9_6512 | D28S | 6.18 |
| 4 | N2G9_6512 | D28S, NH31 HN (1) | 4.75 |
| 5 | N2G9_6512 | D28S, H32N | 5.42 |
| 6 | N2G9_6512 | D28S, H32N, K92H | 8.79 |
| 7 | N2G9_6512 | K92D | 6.64 |
| 8 | N2G9_6512 | D28S, NH31 HN, S91Y (2) | 4.7 |
| 9 | N2G9_6512 | D28S, NH31 HN, K92D | 8.95 |
| 10 | N2G9_6512 | D28S, S91Y | Too Low |
| 11 | N2G9_6512 | D28, K92D | 8.91 |

TABLE 2

| | Frequency of mutation; | | | | | | | | | | | | |
|---|---|---|---|---|---|---|---|---|---|---|---|---|---|
| HC CDR3 | 98 | 99 | 100 | 101 | 102 | 103 | 104 | 105 | 106 | 107 | 108 | 109 | 110 |
| E3 | G | G | Y | W | Y | A | T | S | Y | Y | F | D | Y |
| 911 | G | G | Y | Y | Y | G | T | S | Y | Y | F | D | Y |
| | | | A(1) | K(4) | D(5) | S(4) | W(3) | S(3) | W(2) | | | A(1) | |
| | | | | S(3) | K(3) | D(2) | S(2) | D(2) | H(2) | | | V(1) | |
| | | | | W(2) | S(2) | K(2) | Y(2) | Q(1) | A(2) | | | | |
| | | | | P(2) | Q(2) | W(1) | L(2) | H(1) | P(1) | | | | |
| | | | | D(2) | W(1) | Q(1) | Q(1) | A(1) | D(1) | | | | |
| | | | | L(1) | P(1) | P(1) | P(1) | | Q(1) | | | | |
| | | | | H(1) | L(1) | H(1) | A(1) | | | | | | |
| | | | | | H(1) | | | | | | | | |

| LC CDR1 | 24 | 25 | 26 | 27 | 28 | 29 | 30 | 31 | 32 | 33 | 34 |
|---|---|---|---|---|---|---|---|---|---|---|---|
| E3 | R | A | S | Q | S | I | S | N | N | L | N |
| 911 | R | A | S | Q | D | I | S | N | H | L | N |
| | P(1) | G(2) | N(1) | P(2) | S(2) | H(1) | P(3) | H(3) | K(2) | Q(2) | A(2) |
| | | | Q(1) | A(1) | G(1) | Y(1) | Y(1) | D(3) | Y(1) | D(1) | 5(1) |
| | | | R(1) | | N(1) | S(1) | T(1) | S(2) | S(1) | H(1) | |
| | | | W(1) | | A(1) | | Q(1) | P(2) | P(1) | Y(1) | |
| | | | P(1) | | | | | K(2) | N(1) | P(1) | |
| | | | D(1) | | | | | Q(1) | | N(1) | |
| | | | | | | | | L(1) | | K(1) | |
| | | | | | | | | A(1) | | | |

| LC CDR3 | 89 | 90 | 91 | 92 | 93 | 94 | 95 | 96 | 97 |
|---|---|---|---|---|---|---|---|---|---|
| E3 | Q | Q | E | H | T | L | P | Y | T |
| 911 | Q | Q | S | K | T | L | P | Y | T |
| | | | K(2) | D(3) | P(2) | K(1) | S(1) | | A(1) |
| | | | Y(2) | Q(1) | K(1) | E(1) | K(1) | | |
| | | | D(1) | H(1) | A(1) | Y(1) | A(1) | | |
| | | | I(1) | Y(1) | L(1) | W(1) | Y(1) | | |
| | | | P(1) | P(1) | H(1) | Q(1) | | | |
| | | | | L(1) | Y(1) | H(1) | | | |
| | | | | E(1) | W(1) | | | | |

TABLE 3-continued

| # | HC | LC | expression |
|---|---|---|---|
| 12 | N2G9_6512 | D28S, H32N, SK91EH | 4.41 |
| 13 | N2G9_6512 | SK91EH | 4.2 |
| 14 | N2G9_6512 | K92H | 11.7 |
| 15 | N2G9_6512 | S91E | 4.56 |
| 16 | N2G9_6512 | H32N | 8.23 |
| 17 | Y100W | E3M | 10.7 |
| 18 | Y101W | E3M | 11.8 |
| 19 | Y102W | E3M | 9.81 |
| 20 | Y101D | E3M | 4.92 |
| 21 | YY100WD | E3M | 12.1 |
| 22 | Y101W, G103A | E3M | 7.14 |
| 23 | G103A | E3M | Too Low |
| 24 | Y100W | S91Y | 4.7 |
| 25 | Y101W | S91Y | 4.11 |
| 26 | Y102W | S91Y | 4.78 |
| 27 | Y101D | S91Y | Too Low |
| 28 | YY100WD | S91Y | 5.58 |
| 29 | Y101W, G103A | S91Y | 4.4 |
| 30 | G103A | S91Y | 4.62 |
| 31 | N2G9_6512 | E3M | 13.1 |
| 32 | Y100W | D28S | 7.35 |
| 33 | Y100W | D28S, NH31HN (1) | 6.37 |
| 34 | Y100W | D28S, H32N | 5.88 |
| 35 | Y100W | D28S, H32N, K92H | 6.66 |
| 36 | Y100W | K92D | 13.5 |
| 37 | Y100W | D28S, NH31HN, S91Y (2) | 7.45 |
| 38 | Y100W | D28S, NH31HN, K92D | 11.7 |
| 39 | Y100W | D28S, S91Y | 6.57 |
| 40 | Y100W | D28, K92D | 10.1 |
| 41 | Y100W | D28S, H32N, SK91EH | 5.91 |
| 42 | Y100W | SK91EH | Too Low |
| 43 | Y100W | K92H | 10.6 |
| 44 | Y100W | S91E | 3.03 |
| 45 | Y100W | H32N | 11.2 |
| 46 | Y101W | D28S | 6.76 |
| 47 | Y101W | D28S, NH31HN (1) | 5.04 |
| 48 | Y101W | D28S, H32N | 5.5 |
| 49 | Y101W | D28S, H32N, K92H | 9.21 |
| 50 | Y101W | K92D | 12.3 |
| 51 | Y101W | D28S, NH31HN S91Y (2) | 5.38 |
| 52 | Y101W | D28S, NH31HN, K92D | 5.43 |
| 53 | Y101W | D28S, S91Y | 5.85 |
| 54 | Y101W | D28, K92D | 8.41 |
| 55 | Y101W | D28S, H32N, SK91EH | 5.4 |
| 56 | Y101W | SK91EH | Too Low |
| 57 | Y101W | K92H | 12 |
| 58 | Y101W | S91E | Too Low |
| 59 | Y101W | H32N | 11.2 |
| 60 | Negative control; no DNA | | Too Low |
| 61 | N2G9_6512 | E3M | 15.8 |
| 62 | Y102W | D28S | 9.39 |
| 63 | Y102W | D28S, NH31HN (1) | 4.8 |
| 64 | Y102W | D28S, H32N | Too Low |
| 65 | Y102W | D28S, H32N, K92H | 8.74 |
| 66 | Y102W | K92D | 11.5 |
| 67 | Y102W | D28S, NH31HN, S91Y (2) | 5.12 |
| 68 | Y102W | D28S, NH31HN, K92D | 15.4 |
| 69 | Y102W | D28S, S91Y | 6.19 |
| 70 | Y102W | D28, K92D | 13.8 |
| 71 | Y102W | D28S, H32N, SK91EH | 4.89 |
| 72 | Y102W | SK91E H | 7.37 |
| 73 | Y102W | K92H | 10.3 |
| 74 | Y102W | S91E | Too Low |
| 75 | Y102W | H32N | 12.7 |
| 76 | Y101D | D28S | 12.6 |
| 77 | Y101D | D28S NH31HN (1) | Too Low |
| 78 | Y101D | D28S, H32N | 8.55 |
| 79 | Y101D | D28S, H32N, K92H | 9.95 |
| 80 | Y101D | K92D | 13.4 |
| 81 | Y101D | D28S, NH31HN, S91Y (2) | 5.55 |
| 82 | Y101D | D28S, NH31HN, K92D | 17.4 |
| 83 | Y101D | D28S, S91Y | 6.02 |
| 84 | Y101D | D28, K92D | 14.5 |
| 85 | Y101D | D28S, H32N, SK91EH | 4.65 |
| 86 | Y101D | SK91EH | 8.18 |
| 87 | Y101D | K92H | 11.1 |
| 88 | Y101D | S91E | Too Low |
| 89 | Y101D | H32N | 13.9 |
| 90 | Negative control; no DNA | | Too Low |

TABLE 4

| # | HC | LC | expression |
|---|---|---|---|
| 91 | N2G9_6512 | E3M | 12.9 |
| 92 | YY100WD | D28S | 7.2 |

TABLE 4-continued

| # | HC | LC | expression |
|---|---|---|---|
| 93 | YY100WD | D28S,NH31H (1) | Too Low |
| 94 | YY100WD | D28S, H32N | Too Low |
| 95 | YY100WD | D28S, H32N, K92H | 6.01 |
| 96 | YY100WD | K92D | 11.6 |
| 97 | YY100WD | D28S, NH31HN, S91Y (2) | 6.53 |
| 98 | YY100WD | D28S, NH31HN, K92D | 15.3 |
| 99 | YY100WD | D28S, S91Y | 4.22 |
| 100 | YY100WD | D28, K92D | 11.3 |
| 101 | YY100WD | D28S, H32N, SK91EH | Too Low |
| 102 | YY100WD | SK91EH | Too Low |
| 103 | YY100WD | K92H | 16.5 |
| 104 | YY100WD | S91E | Too Low |
| 105 | YY100WD | H32N | 5.31 |
| 106 | Y101W, G103A | D28S | 4.57 |
| 107 | Y101W, G103A | D28S,NH31HN (1) | Too Low |
| 108 | Y101W, G103A | D28S, H32N | Too Low |
| 109 | Y101W, G103A | D28S, H32N, K92H | 5.62 |
| 110 | Y101W, G103A | K92D | 13.2 |
| 111 | Y101W, G103A | D28S, NH31HN, S91Y (2) | 4.48 |
| 112 | Y101W, G103A | D28S, NH31HN, K92D | 6.88 |
| 113 | Y101W, G103A | D28S, S91Y | 5.26 |
| 114 | Y101W, G103A | D28, K92D | 5.89 |
| 115 | Y101W, G103A | D28S, H32N, SK91EH | Too Low |
| 116 | Y101W, G103A | SK91EH | Too Low |
| 117 | Y101W, G103A | K92H | Too Low |
| 118 | Y101W, G103A | S91E | Too Low |
| 119 | Y101W, G103A | H32N | Too Low |
| 120 | Y101W, G103A | D28S, H32N, SK91EH | Too Low |
| 121 | N2G9_6512 | E3M | 10.2 |
| 122 | G103A | D28S | Too Low |
| 123 | G103A | D28S, NH31HN (1) | Too Low |
| 124 | G103A | D28S, H32N | 3.6 |
| 125 | G103A | D28S, H32N, K92H | 12.2 |
| 126 | G103A | K92D | 15.9 |
| 127 | G103A | D28S, NH31HN, S91Y (2) | 6.36 |
| 128 | G103A | D28S, NH31HN, K92D | 13.9 |
| 129 | G103A | D28S, S91Y | 6.32 |
| 130 | G103A | D28, K92D | 13.5 |
| 131 | G103A | D28S, NH31HN, S91Y (1) | Too Low |
| 132 | G103A | SK91EH | 9.04 |
| 133 | G103A | K92H | 4.88 |
| 134 | G103A | S91E | Too Low |
| 135 | G103A | H32N | 4.01 |
| 136 | repeat 58 | | Too Low |
| 137 | repeat 59 | | 13.3 |
| 138 | repeat 115 | | Too Low |

SPR on the supernatants were performed as an initial screen, good binders were purified, and pure mAb was again run via SPR to measure binding to canine NGF (TABLE 5). Constructs LTM109 and LTM135 were chosen to progress based on binding affinities.

TABLE 5

BiacoreT100: Dog NGF and Abs Binding Kinetics Summary

| Name | HC | LC | 11/8 $K_D$ (M) | 11/22 $K_D$ (M) | 11/24 $K_D$ (M) | 11/29 $K_D$ (M) | Comments |
|---|---|---|---|---|---|---|---|
| hE3 | Y101W,G103A | D28S, H32N, SK91EH | 1.29E−12 | 1.12E−12 | 3.37E−12 | 1.49E−12 | |
| CanE3M 65112 | | | 3.35E−09 | 1.46E−09 | 2.35E−09 | 3.51E−09 | |
| 32 | Y100W | D28S | | | 2.25E−09 | | |
| 33 | Y100W | *D28S,NH31HN | | | no binding | no binding | |
| 34 | Y100W | D28S, H32N | | | 6.39E−10 | 8.85E−10 | ✓/? |
| 35 | Y100W | D28S, H32N, K92H | | | 2.37E−10 | 8.10E−10 | ✓ |
| 36 | Y100W | K92D | | | 5.50E−09 | | |
| 37 | Y100W | *D28S, NH31HN, S91Y | | | 1.91E−09 | | |
| 38 | Y100W | D28S, NH31HN, K92D | | | 2.15E−09 | | |
| 39 | Y100W | D28S, S91Y | | | no binding | no binding | |
| 40 | Y100W | D28S, K92D | | | weak binding | weak binding | |
| 41 | Y100W | D28S, H32N, SK91EH | | | weak binding | weak binding | |
| 43 | Y100W | K92H | | | 5.67E−09 | | |
| 44 | Y100W | S91E | | | no binding | | |
| 45 | Y100W | H32N | | | 2.10E−09 | 4.35E−09 | |
| 109 | Y101W, G103A | D28S, H32N, K92H | | | 5.15E−10 | 7.48E−10 | ✓ |
| 110 | Y101W, G103A | K92D | | | 3.26E−12 | 9.42E−10 | Agg? |
| 111 | Y101W, G103A | *D28S, NH31HN, S91Y | | | 1.46E−10 | 2.88E−11 | Agg? |
| 112 | Y101W, G103A | D28S, NH31HN, K92D | | | 1.65E−12 | 1.52E−11 | Agg? |
| 133 | G103A | K92H | | | 1.33E−12 | 1.10E−11 | Agg? |
| 135 | G103A | H32N | | | 1.38E−10 | 6.10E−12 | Agg? |

Various KD's correspond to different sensors, surface density varies slightly. Agg indicates that a binding curve showing signs of antibody aggregation was seen in at least one run.

Four rounds of phage display using the SSM library were performed using single site mutations on the same wild-type sequence used for LTM. Libraries were panned against biotinylated or free canine NGF and selected for high affinity and slow off-rate after each round. Selections were run as shown below, round 4 outputs were TOPO cloned and sequenced.

Site-Saturation Mutagenesis for NGF Affinity Maturation—Selection Strategy

Samples used:
(1) negative control using streptavidin beads w/o antigen
(2) bioNGF antigen on streptavidin beads.
(3) Immunotube with dNGF immobilized on tube
(4) E33 positive control on streptavidin beads with bioNGF
(5) E33 positive control with immunotube/dNGF antigen
  * note positive controls will verify appropriate stringency Note: Using chemical elution only (100 mM TEA) to assure that we don't screen out the tightest binders.
Negative selection for immunotube=tube w/o dNGF immobilized.
Negative selection for strep beads=beads w/o bioNGF immobilized.
extended washes select for very slow off-rates; stringency increased with rounds.

Round 1: Samples (1), (2), (3)
Immunotube: 50 ug/mL dNGF

| | | | |
|---|---|---|---|
| Block | | | 2 hours |
| Negative selection | | | 1 hour |
| Bind | | | 1 hour |
| Wash | 10x PBST | wash # 4 | 1 hour |
| | 10x PBS | wash #17 | 2 hours |
| Elute | | | 30 min |

Strep Beads: 100 nM bioNGF (negative control=PBS only)

| | | | |
|---|---|---|---|
| Block phage | | | 1 hour |
| Block beads | | | 2 hours |
| Negative selection | | | 1 hour |
| Bind antigen/phage | | | 1 hour |
| Bind complex/beads | | | 15 min |
| Wash | 6x MPBST | wash #4 | 1 hour |
| | 6x MPBST | wash #11 | 2 hours |
| | 2x PBS | | |
| * each line represents transfer to new tube | | | |
| Elute | | | 5 min |

Round 2: Samples (1), (2), (3), (4), (5)
Immunotube: 20 ug/mL dNGF

| | | | |
|---|---|---|---|
| Block | | | 2 hours |
| Negative selection | | | 1 hour |
| Bind | | | 1 hour |
| Wash | 15x PBST | wash # 4 | 2 hours |
| | 15x PBS | wash #25 | 2.5 hours |
| Elute | | | 30 min |

Strep Beads: 50 nM bioNGF (negative control=PBS only)

| | | | |
|---|---|---|---|
| Block phage | | | 1 hour |
| Block beads | | | 2 hours |
| Negative selection | | | 1 hour |
| Bind antigen/phage | | | 1 hour |
| Bind complex/beads | | | 15 min |
| Wash | 10x MPBST | wash #4 | 2 hours |
| | 10x MPBST | wash #18 | 2 hours |
| | 4x PBS | PBS wash #2 | 30 min |
| * each line represents transfer to new tube | | | |
| Elute | | | 5 min |

Round 3: Samples (1), (2), (3), (4), (5)
Immunotube: 20 ug/mL dNGF

| | | | |
|---|---|---|---|
| Block | | | 2 hours |
| Negative selection | | | 1 hour |
| Bind | | | o/n |
| Wash | 15x PBST | wash # 4 | 2 hours |
| | 15x PBS | wash #25 | 6 hours |
| Elute | | | 30 min |

Strep Beads: 30 nM bioNGF (negative control=PBS only)

| | | | |
|---|---|---|---|
| Block phage | | | 1 hour |
| Block beads | | | 2 hours |
| Negative selection | | | 1 hour |
| Bind antigen/phage | | | 1 hour |
| Bind complex/beads | | | o/n |
| Wash | 10x MPBST | wash #4 | 2 hours |
| | 10x MPBST | wash #18 | 30 min |
| | 4x PBS | PBS wash #2 | 6 hours |
| * each line represents transfer to new tube | | | |
| Elute | | | 5 min |

Round 4: Samples (1), (2), (3), (4), (5)
Immunotube: 10 ug/mL dNGF

| | | | |
|---|---|---|---|
| Block | | | 2 hours |
| Negative selection | | | 1 hour |
| Bind | | | 1 hour |
| Wash | 20x PBST | wash # 4 | 3 hours |
| | 20x PBS | wash #32 | 13 hours |
| Elute | | | 30 min |

Strep Beads: 15 nM bioNGF (negative control=PBS only)

| | | | |
|---|---|---|---|
| Block phage | | | 1 hour |
| Block beads | | | 2 hours |
| Negative selection | | | 1 hour |
| Bind antigen/phage | | | 1 hour |
| Bind complex/beads | | | 15 min |
| Wash | 15x MPBST | wash #4 | 3 hours |
| | 15x MPBST | | |
| | 5x PBS | PBS wash #2 | 13 hours |
| * each line represents transfer to new tube | | | |
| Elute | | | 5 min |

TABLE 6

| sample | \multicolumn{15}{c}{position} |
| --- | --- | --- | --- | --- | --- | --- | --- | --- | --- | --- | --- | --- | --- | --- | --- |
|  | 50 | 51 | 52 | 53 | 54 | 55 | 56 | 29 | 30 | 31 | 32 | 33 | 34 | 35 | 50 | 51 |
| RN911 | Y | I | S | R | F | H | S | L | I | G | Y | D | I | N | M | I |
| E3 | Y | T | S | R | F | H | S | L | I | G | Y | D | L | N | I | I |
| A01 | Y | I | S | R | F | H | S | L | I | G | Y | D | I | N | M | I |
| B01 | Y | I | S | R | F | H | S | L | I | G | Y | D | I | N | M | I |
| B06 | Y | I | S | R | F | H | S |  |  |  |  |  |  |  |  |  |
| P03 | Y | I | S | R | W | H | S | L | I | G | Y | D | I | N | M | I |
| F06 | Y | I | S | R | F | H | S | L | I | G | Y | D | I | P | M | I |
| D10 | Y | V | S | R | F | H | S | L | I | G | Y | D | I | N | M | I |
| E07 | Y | I | S | R | V | H | S | L | I | G | Y | D | I | N | M | I |
| C07 | Y | I | S | R | F | H | S | L | I | G | Y | D | I | N | M | I |
| C09 | Y | I | S | R | F | H | S | L | I | G | Y | D | I | Y | M | I |
| A02 | Y | I | R | R | F | H | S | L | I | G | X | D | I | N | M | I |
| D08 | Y | I | S | Q | F | H | S | L | I | G | Y | D | I | N | M | I |
| D09 | Y | I | S | R | F | H | S | L | I | G | Y | D | I | Y | M | I |
| A11 | Y | I | S | R | F | H | S |  |  |  |  |  |  |  |  |  |
| C12 | Y | N | S | R | F | H | S | L | I | G | Y | D | I | N | M | I |
| H11 | Y | I | S | R | F | H | S |  |  |  |  |  |  |  |  |  |
| F11 | Y | I | R | R | F | H | S |  |  |  |  |  |  |  |  |  |
| A08 | Y | I | R | R | F | H | S |  |  |  |  |  |  |  |  |  |
| C06 | Y | I | S | R | F | H | S |  |  |  |  |  |  |  |  |  |
| Apparent pre-Set preference |  |  |  | R |  |  |  |  |  |  | Y |  |  |  |  |  |

| sample | \multicolumn{14}{c}{position} | SEQ ID |
| --- | --- | --- | --- | --- | --- | --- | --- | --- | --- | --- | --- | --- | --- | --- | --- |
|  | 52 | 53 | 54 | 55 | 56 | 57 | 58 | 59 | 60 | 61 | 62 | 63 | 64 | 65 |  |
| RN911 | W | G | D | G | T | T | D | Y | N | S | A | L | K | S | 62 |
| E3 | W | G | D | G | T | T | D | Y | N | S | A | Y | K | S | 63 |
| A01 | W | G | D | G | T | T | D | K | N | S | A | L | K | S | 64 |
| B01 | W | G | D | G | T | T | D | Y | N | S | N | L | K | S | 65 |
| B06 |  |  |  |  |  |  |  |  |  |  |  |  |  | S | 66 |
| P03 | W | G | D | G | T | T | D | Y | N | S | A | L | K | S | 67 |
| F06 | W | G | D | G | T | T | D | Y | N | S | A | L | K | S | 68 |
| D10 | W | G | D | G | T | T | D | Y | N | S | A | L | W | S | 69 |
| E07 | W | G | D | G | T | T | D | Y | N | K | A | L | K | S | 70 |
| C07 | W | G | D | G | T | T | D | Y | N | S | A | L | K | S | 71 |
| C09 | W | G | D | G | T | T | D | Y | N | S | A | L | K | S | 72 |
| A02 | W | G | D | G | T | T | D | K | N | S | A | L | K | S | 73 |
| D08 | W | G | D | I | T | T | D | Y | N | S | A | L | K | S | 74 |
| D09 | W | G | D | G | T | T | D | Y | N | S | A | L | K | S | 75 |
| A11 |  |  |  |  |  |  |  |  |  |  |  |  |  |  | 76 |
| C12 | W | G | D | G | T | T | D | Y | N | S | A | L | K | S | 77 |
| H11 |  |  |  |  |  |  |  |  |  |  |  |  |  |  | 78 |
| F11 |  |  |  |  |  |  |  |  |  |  |  |  |  |  | 79 |
| A08 |  |  |  |  |  |  |  |  |  |  |  |  |  |  | 80 |
| C06 |  |  |  |  |  |  |  |  |  |  |  |  |  |  | 81 |
| Apparent pre-Set preference |  |  |  |  |  | K |  |  |  |  |  |  |  |  |  |

Table 6 above shows the sequenced outputs from SSM-library display as well as initial diversity. Enriched sites were selected for both single-site and multi-site (combinations of enriched sites) mutations and subsequent IgG conversion. SSM mutations for both heavy and light chains were generated on three templates: (1) wild-type mAb, (2) LTM109 (3) LTM135.

Mutated antibodies were expressed in HEK293 cells and evaluated for binding affinities to canine NGF (results below; expression results in Tables 7-9). Antibodies SSM57 (SEQ ID NO. 27 "CAN-SSM57-VL, SEQ ID NO 26 "CAN-SSM-E3M-VL"), SSM58 (SEQ ID NO. 28 "CAN-SSM58-VH", SEQ ID NO. 26 "CAN-SSM-E3M-VL"), and SSM66 (SEQ ID NO. 29 "CAN-SSM66-VH", SEQ ID NO. 26 "CAN-SSM-E3M-VL") showed highest affinities.

TABLE 7

| | \multicolumn{16}{c}{PHASE DISPLAY OUTPUT} |
| --- | --- | --- | --- | --- | --- | --- | --- | --- | --- | --- | --- | --- | --- | --- | --- | --- |
| | \multicolumn{16}{c}{POSITION} |
| SAMPLE | 50 | 51 | 52 | 53 | 54 | 55 | 56 | 29 | 30 | 31 | 32 | 33 | 34 | 35 | 50 | 51 |
| RN911 | Y | I | S | R | F | H | S | L | I | G | Y | D | I | N | M | I |
| E3 | Y | T | S | R | F | H | S | L | I | G | Y | D | L | N | I | I |
| ImP2_E06 | Y | I | S | R | F | H | S | L | I | G | Y | D | I | N | M | I |
| ImP2_C08 | Y | I | S | R | F | H | S | L | I | G | Y | D | I | N | M | I |

TABLE 7-continued

PHASE DISPLAY OUTPUT

| | | | | | | | | | | | | | | |
|---|---|---|---|---|---|---|---|---|---|---|---|---|---|---|
| ImP2_H06 | Y | I | S | R | F | H | S | L | I | E | Y | D | I | N | M | I |
| ImP1_G12 | Y | I | S | R | F | H | S | L | I | G | Y | D | Q | N | M | I |
| ImP1_B02 | Y | I | S | R | F | H | S | L | I | G | Y | D | I | N | M | I |
| ImP1_G12 | Y | I | S | S | F | H | S | L | I | G | Y | D | I | N | M | I |
| ImP2_G02 | Y | I | S | S | F | H | S | L | I | G | Y | D | I | N | M | I |
| ImmRB11 | Y | I | S | R | F | H | S | L | I | G | Y | D | I | N | M | I |
| ImmRD07 | Y | I | S | R | F | H | S | L | I | G | Y | H | I | N | M | I |
| ImmRC08 | Y | I | S | R | F | H | S | L | I | G | Y | D | I | N | M | I |
| ImmRE08 | Y | I | S | R | F | H | S | L | I | E | Y | D | I | N | M | I |
| ImmRA06 | Y | I | S | R | F | H | S | L | I | G | Y | D | I | N | M | I |
| ImmRA10 | Y | I | S | R | F | H | S | L | I | G | Y | D | I | N | M | I |
| ImmRH02 | Y | I | S | K | F | H | S | L | I | G | Y | D | I | N | M | I |
| ImmRG09 | Y | I | S | R | F | H | S | L | I | G | Y | D | I | N | M | I |
| ImmRD12 | Y | I | S | S | F | H | S | L | I | G | Y | D | I | N | M | I |
| ImmRE04 | Y | I | S | R | F | H | S | L | I | G | Y | D | Q | N | M | I |
| ImmRC06 | Y | I | S | R | F | H | S | L | I | G | Y | D | I | N | M | I |
| ImmRG02 | Y | I | R | R | F | H | S | L | I | G | Y | D | I | N | M | I |
| ImmRA11 | Y | I | S | R | F | H | S | L | I | G | Y | D | I | N | M | I |
| ImmRC02 |   |   |   |   |   |   |   | L | I | G | Y | D | I | N | M | I |
| ImmRG05 | Y | I | S | R | F | H | S | L | I | G | Y | D | Q | N | M | I |

| SAMPLE | POSITION | | | | | | | | | | | | | | SEQ ID NO. |
|---|---|---|---|---|---|---|---|---|---|---|---|---|---|---|---|
| | 52 | 53 | 54 | 55 | 56 | 57 | 58 | 59 | 60 | 61 | 62 | 63 | 64 | 65 | |
| RN911 | W | G | D | G | T | T | D | Y | N | S | A | L | K | S | 62 |
| E3 | W | G | D | G | T | T | D | Y | N | S | A | V | K | S | 63 |
| ImP2_E06 | W | G | T | G | T | T | D | Y | N | S | A | L | K | S | 82 |
| ImP2_C08 | W | G | D | I | T | T | D | Y | N | S | A | L | K | S | 83 |
| ImP2_H06 | W | G | D | G | T | T | D | Y | N | S | A | L | K | S | 84 |
| ImP1_G12 | W | G | D | G | T | T | D | Y | N | S | A | L | K | S | 85 |
| ImP1_B02 | W | G | T | G | T | T | D | Y | N | S | A | L | K | S | 86 |
| ImP1_G12 | W | G | D | G | T | T | D | Y | N | S | A | L | K | S | 87 |
| ImP2_G02 | W | G | D | G | T | T | D | Y | N | S | A | L | K | S | 88 |
| ImmRB11 | W | G | T | G | T | T | D | Y | N | S | A | L | K | S | 89 |
| ImmRD07 | W | G | D | G | T | T | D | Y | N | S | A | L | K | S | 90 |
| ImmRC08 | W | G | T | G | T | T | D | Y | N | S | A | L | K | S | 91 |
| ImmRE08 | W | G | D | G | T | T | D | Y | N | S | A | L | K | S | 92 |
| ImmRA06 | W | G | D | I | T | T | D | Y | N | S | A | L | K | S | 93 |
| ImmRA10 | W | G | S | G | T | T | D | Y | N | S | A | L | K | S | 94 |
| ImmRH02 | W | G | D | G | T | T | D | Y | N | S | A | L | K | S | 95 |
| ImmRG09 | W | G | D | G | T | T | D | Y | N | S | A | I | K | S | 96 |
| ImmRD12 | W | G | D | G | T | T | D | Y | N | S | A | L | K | S | 97 |
| ImmRE04 | W | G | D | G | T | T | D | Y | N | S | A | L | K | S | 98 |
| ImmRC06 | W | G | T | G | T | T | D | Y | N | S | A | L | K | S | 99 |
| ImmRG02 | W | G | D | G | T | T | D | Y | N | S | A | L | K | S | 100 |
| ImmRA11 | W | G | T | G | T | T | D | Y | N | S | A | L | K | S | 101 |
| ImmRC02 | W | G | D | G | T | T | D | Y | N | S | A | L | K | S | 102 |
| ImmRG05 | W | G | D | G | T | T | D | Y | N | S | A | L | K | S | 103 |

TABLE 8

| # | LIGHT CHAIN | HEAVY CHAIN | EXPRESSION |
|---|---|---|---|
| 1' | E3M | N2G96512 | Too Low |
| 2' | E3M | SSMwtHCG31Q | 8.02 |
| 3' | E3M | SSMwtHCG31E | 25 |
| 4' | E3M | SSMwtHCD33H | Too Low |
| 5' | E3M | SSMwtHCI34Q | Too Low |
| 6' | E3M | SSMwtHCD54T | Too Low |
| 7' | E3M | SSMwtHCDG54TI | Too Low |
| 8' | E3M | SSMwtHCD54T, L63I | 4.94 |
| 9' | E3M | SSMwtHCD54T, D33H | Too Low |
| 10' | E3M | SSMwtHCD54T, I34Q | Too Low |
| 11' | E3M | SSMwtHCD54T, G31E | 5.75 |
| 1b' | E3M | N2G96512 | 11.5 |
| 12' | SSMwtLCR53S | N2G96512 | 17.3 |

TABLE 8-continued

| # | LIGHT CHAIN | HEAVY CHAIN | EXPRESSION |
|---|---|---|---|
| 13' | SSMwtLCR53S | SSMwtHCG31Q | 23.5 |
| 14' | SSMwtLCR53S | SSMwtHCG31E | 27.3 |
| 15' | SSMwtLCR53S | SSMwtHCD33H | Too Low |
| 16' | SSMwtLCR53S | SSMwtHCI34Q | Too Low |
| 17' | SSMwtLCR53S | SSMwtHCD54T | 11.9 |
| 18' | SSMwtLCR53S | SSMwtHCDG54TI | Too Low |
| 19' | SSMwtLCR53S | SSMwtHCD54T, L63I | 14.5 |
| 20' | SSMwtLCR53S | SSMwtHCD54T, D33H | 4.15 |
| 21' | SSMwtLCR53S | SSMwtHCD54T, I34Q | Too Low |
| 22' | SSMwtLCR53S | SSMwtHCD54T, G31E | 15.5 |

| # | LIGHT CHAIN | HEAVY CHAIN | EXPRESSION | 2ND TRY EXPRESSION |
|---|---|---|---|---|
| 1c' | E3M | N2G96512 | 5.35 | 16 |
| 23' | E3M H32N | HC135 (G103A) | Too Low | 11.4 |
| 24' | E3M H32N | SSM135HCG31Q | Too Low | 3.7 |
| 25' | E3M H32N | SSM135HCG31E | 3 | 3.8 |
| 26' | E3M H32N | SSM135HCD33H | Too Low | Too Low |
| 27' | E3M H32N | SSM135HCI34Q | Too Low | Too Low |
| 28' | E3M H32N | SSM135HCD54T | Too Low | Too Low |
| 29' | E3M H32N | SSM135HCDG54TI | Too Low | Too Low |
| 30' | E3M H32N | SSM135HCD54T, L63I | Too Low | Too Low |
| 31' | E3M H32N | SSM135HCD54T, D33H | Too Low | Too Low |
| 32' | E3M H32N | SSM135HCD54T, I34Q | Too Low | Too Low |
| 33' | E3M H32N | SSM135HCD54T, G31E | Too Low | Too Low |
| 34' | SSM135LCR53S | HC135 (G103A) | 5.55 | 12.4 |
| 35' | SSM135LCR53S | SSM135HCG31Q | 3 | 16.5 |
| 36' | SSM135LCR53S | SSM135HCG31E | 6.06 | 11.7 |
| 37' | SSM135LCR53S | SSM135HCD33H | Too Low | 12.3 |
| 38' | SSM135LCR53S | SSM135HCI34Q | Too Low | Too Low |
| 39' | SSM135LCR53S | SSM135HCD54T | Too Low | 7.36 |
| 40' | SSM135LCR53S | SSM135HCDG54TI | Too Low | Too Low |
| 41' | SSM135LCR53S | SSM135HCD54T, L63I | Too Low | 8.14 |
| 42' | SSM135LCR53S | SSM135HCD54T, D33H | Too Low | Too Low |
| 43' | SSM135LCR53S | SSM135HCD54T, I34Q | Too Low | Too Low |
| 44' | SSM135LCR53S | SSM135HCD54T, G31E | 3.17 | 13.6 |
| 1d' | E3M | N2G96512 | Too Low | |
| 45' | E3M D28S, H32N, K92H | HC109 (Y101W, G103A) | Too Low | 4.12 |
| 46' | E3M D28S, H32N, K92H | SSM109HCG31Q | Too Low | 5.27 |
| 47' | E3M D28S, H32N, K92H | SSM109HCG31E | Too Low | 6.67 |
| 48' | E3M D28S, H32N, K92H | SSM109HCD33H | Too Low | Too Low |
| 49' | E3M D28S, H32N, K92H | SSM109HCI34Q | Too Low | Too Low |
| 50' | E3M D28S, H32N, K92H | SSM109HCD54T | Too Low | Too Low |
| 51' | E3M D28S, H32N, K92H | SSM109HCDG54TI | Too Low | Too Low |
| 52' | E3M D28S, H32N, K92H | SSM109HCD54T, L63I | Too Low | Too Low |
| 53' | E3M D28S, H32N, K92H | SSM109HCD54T, D33H | Too Low | Too Low |
| 54' | E3M D28S, H32N, K92H | SSM109HCD54T, I34Q | Too Low | Too Low |
| 55' | E3M D28S, H32N, K92H | SSM109HCD54T, G31E | Too Low | 5.97 |
| 56' | SSM109LCR53S | HC109 (Y101W, G103A) | Too Low | 14.5 |
| 57' | SSM109LCR53S | SSM109HCG31Q | Too Low | 12.1 |
| 58' | SSM109LCR53S | SSM109HCG31E | Too Low | 15.3 |
| 59' | SSM109LCR53S | SSM109HCD33H | Too Low | 11.7 |
| 60' | SSM109LCR53S | SSM109HCI34Q | Too Low | Too Low |
| 61' | SSM109LCR53S | SSM109HCD54T | Too Low | Too Low |
| 62' | SSM109LCR53S | SSM109HCDG54TI | Too Low | Too Low |
| 63' | SSM109LCR53S | SSM109HCD54T, L63I | Too Low | 3.11 |
| 64' | SSM109LCR53S | SSM109HCD54T, D33H | Too Low | Too Low |
| 65' | SSM109LCR53S | SSM109HCD54T, I34Q | Too Low | Too Low |
| 66' | SSM109LCR53S | SSM109HCD54T, G31E | Too Low | 11.6 |

TABLE 9

| Ligand | Samples | Fit | ka (M-1 s-1) | kd (s-1) | KD (M) |
|---|---|---|---|---|---|
| A1 | HBS-EP | 1:1 Binding | 1.39E+07 | 6.61E-08 | no binding |
| A2 | CanE3M 65112 | 1:1 Binding | 1.72E+04 | 8.11E-05 | 4.70E-09 |
| A3 | hE3 | 1:1 Binding | 8.75E+04 | 1.67E-07 | 1.91E-12 |
| A4 | LTM135 | 1:1 Binding | 2.51E+04 | 4.23E-05 | 1.69E-09 |
| A5 | SSM-2 | 1:1 Binding | 8.08E+03 | 1.14E-04 | 1.42E-08 |
| A6 | SSM-3 | 1:1 Binding | 4.04E+03 | 1.67E-04 | 4.14E-08 |
| A7 | SSM-8 | 1:1 Binding | 4.13E+03 | 1.73E-04 | 4.18E-08 |
| A8 | SSM-12 | 1:1 Binding | 9.57E+02 | 4.13E-03 | 4.32E-06 |
| A9 | SSM-13 | 1:1 Binding | 7.75E+03 | 2.41E-03 | 3.11E-07 |
| A10 | SSM-14 | 1:1 Binding | 3.44E+05 | 8.12E-03 | 2.36E-08 |
| A11 | SSM-17 | 1:1 Binding | 2.03E+04 | 1.40E-03 | 6.91E-08 |
| A12 | SSM-19 | 1:1 Binding | 4.38E+04 | 1.64E-03 | 3.74E-08 |
| A13 | SSM-22 | 1:1 Binding | 1.19E+03 | 2.96E-04 | 2.49E-07 |
| A14 | SSM-34 | 1:1 Binding | 6.24E+04 | 1.92E-04 | 3.08E-09 |
| A15 | SSM-36 | 1:1 Binding | 8.20E+03 | 3.30E-04 | 4.02E-08 |

Example 6

Production of Caninized Antibodies Form Glutamine Synthetase (GS) Plasmids

The genes encoding the caninized RN911 mAbs were cloned into GS plasmids pEE 6.4 and pEE 12.4, respectively (Lonza, Basel, Switzerland). The resulting plasmids were digested according to the manufacturer's protocol and ligated together to form a single mammalian expression plasmid. Each plasmid was used to transfect HEK 293 cells and expression was carried out in 20 L of culture media. Protein was isolated form conditioned HEK medium using Protein A affinity chromatography according to standard protein purification methods. Medium was loaded onto chromatographic resin and eluted by pH shift. Eluted protein was pH adjusted, dialyzed, and sterile filtered prior to use. The resulting antibody was greater than 99 percent monomeric by analytical size exclusion chromatography with no high molecular weight aggregates observed. This antibody was subsequently used for evaluation in the dog synovitis model to evaluate in vivo efficacy.

Example 7

Evaluation of Caninized Antibody in the Dog Synovitis Model

Figure 14:
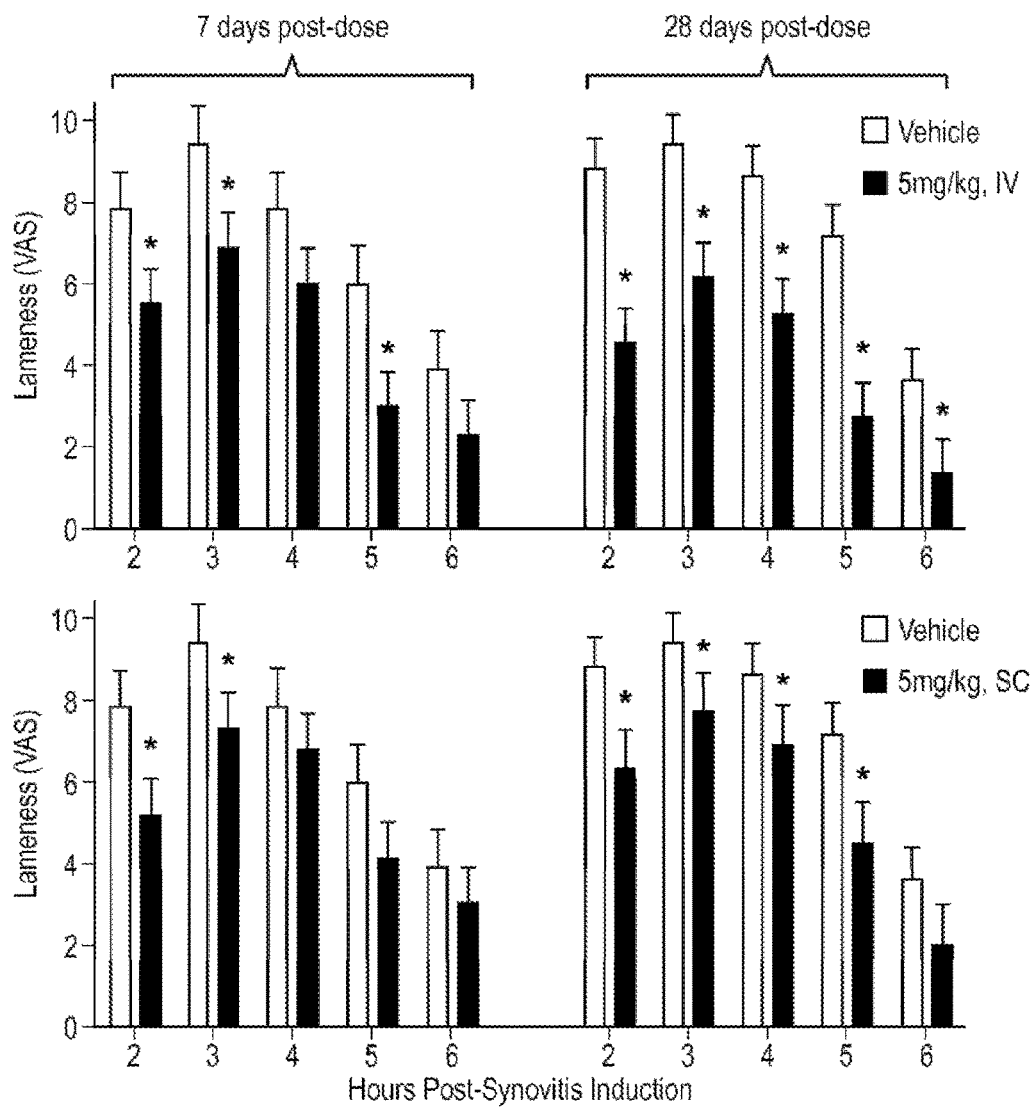

Caninized mAb (CAN-SSME3M-VL, CAN-SSM57-HC) was tested in dog synovitis model at 5 mg/kg IV and 5 mg/kg SC. Results of study are shown in FIG. 14, inducing synovitis at 7 days and 28 days post-dose. Caninized mAb showed efficacy for both SC and IV dosing regimens both 7 and 28 days post-dose.

Example 8

Pharmacokinetics of Caninized Antibody

Figure 16:
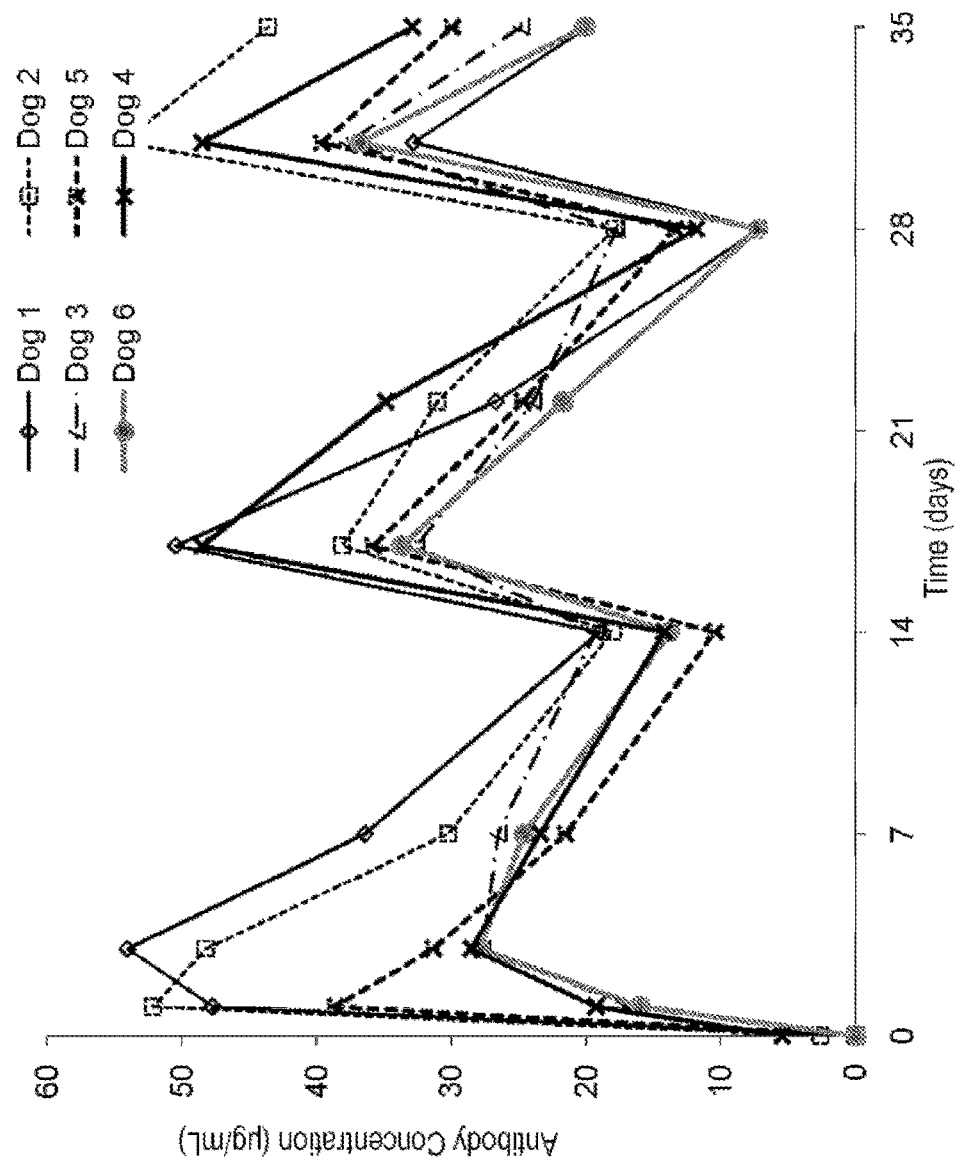

The pharmacokinetics (PK) of the caninized SSM57 mAb (PF-06442591) was studied in six dogs at 5 mg/kg using subcutaneous (SC) administration. Dogs were dosed with mAb at 5 mg/kg SC once every 14 days (Day 0, Day 14, Day 28) for a total of three injections and were euthanized on Day 35 for a full safety assessment (see Safety information below). Serum samples from each dog were collected prior to each dose and periodically over 35 days. Antibody concentration was measured in an ELISA based format in which canine NGF was used to capture mAb from the serum. The antibody was then detected using a labeled anti-dog antibody recognizing the Fc portion of the antibody subclass. Results are shown in FIG. 16.

Example 9

Evaluation of Caninized Antibody in Rat MIA Model

Osteoarthritis (OA) is a degenerative joint disease characterized by joint pain and a progressive loss of articular cartilage. Intra-articular injection of MIA induces loss of articular cartilage with progression of subchondral bone lesions that mimic those of OA. This model offers a rapid and minimally invasive method to reproduce OA-like lesions in a rodent species.

Figure 17:
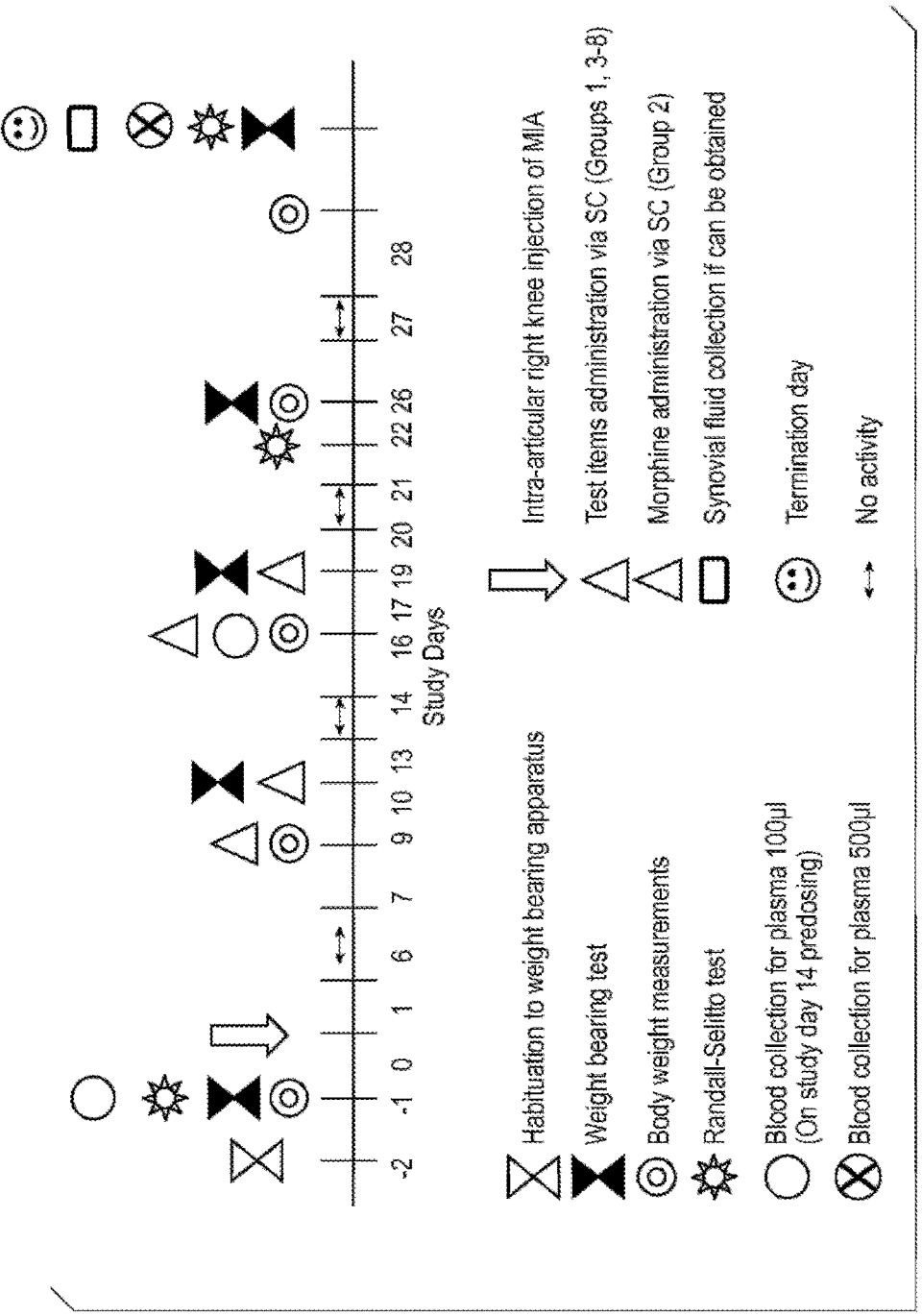
Figure 18:
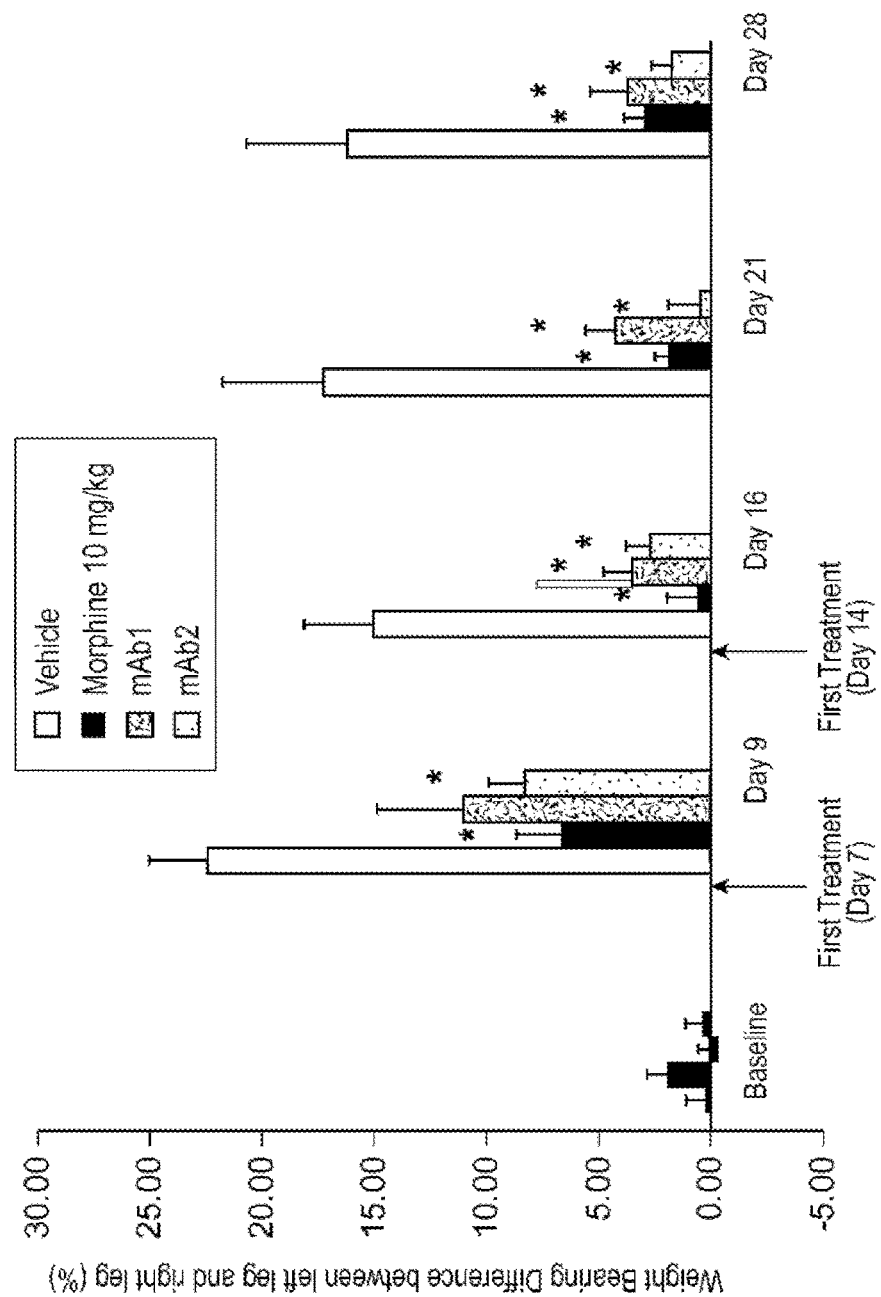
Figure 19:
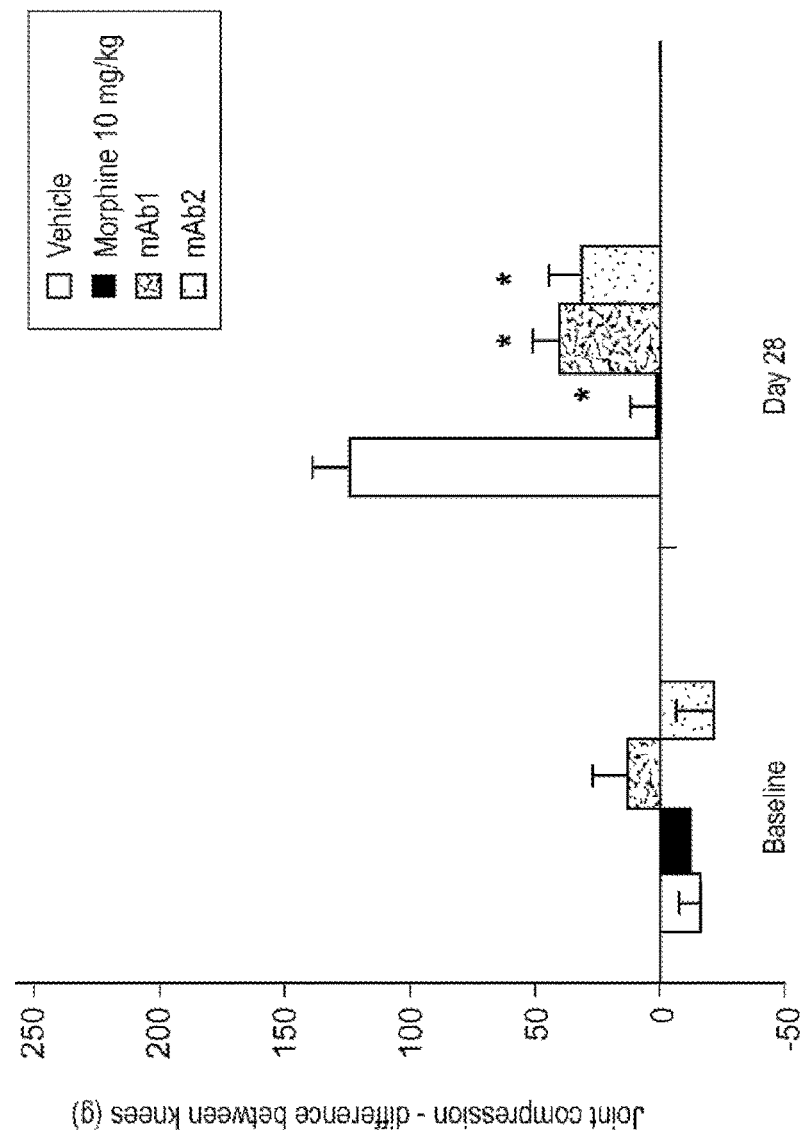

The analgesic effect of caninized anti-NGF antibodies at one dose of MIA in the rat MIA model of osteoarthritis was demonstrated by dosing caninized SSM57 mAb (PF-06442591) twice during the study on study day 7 and study day 14. Pain was assessed using weight bearing test for sustained pain and joint compression (Randall Selitto) test for mechanical hyperalgesia. See FIG. 17 for a schematic of the rat MIA procedure.

TABLE 10

CONSTITUTION OF TEST GROUPS AND DOSE LEVELS
The table lists the experimental groups compared in the study and respective dose levels.

| Group No. | Group Size | Treatment | Volume | Dose (mg/kg) | Route | Dosing Regimen | Testing Regimen |
|---|---|---|---|---|---|---|---|
| 1 | n = 10 | Vehicle | 1.6 ml/kg | 0 | SC | Once on study days 7 and 14 | Weight bearing test on study days −1, 9, 16, 21 and 28. |
| 2 | N = 10 | Positive Control (Morphine) | 5 ml/kg | 10 | SC | Once on study days 9 and 16 1 hour pre weight bearing testing | Randall-Selitto test on study days −1, 20 and 28. |
| 3 | N = 10 | mAb1 | 1.6 ml/kg | 8 | SC | Once on study days 7 and 14 | |
| 4 | N = 10 | mAb2 | 1.6 ml/kg | 8 | SC | | |

Sensitizing Materials Preparation:

A concentration of 60 mg/ml of MIA solution was prepared in saline. Each rat was dosed with 50 μl of prepared solution i.e. 3 mg of MIA.

Vehicle Preparation (Group 1):

The Vehicle control was saline.

Morphine Preparation at a dose of 10 mg/kg (Group 2):

1. Added 13.5 ml saline to 1.5 ml morphine.
2. Injected 1 ml of received solution per rat weighing 200 g.

Test Items Preparation (Groups 3-4):

Antibodies were 5 mg/ml. The compounds were stored at 2-8° C. and protected from light prior to use. No vigorous shaking. The compounds were warmed to room temperature for 1 hour prior to dosing.

Treatment:
Vehicle (Group 1) and Test Item mAb s (Groups 3 and 4) were administered once via SC on testing days 7 and 14.
Morphine (Group 2), the positive control in this study, was administered once via SC on the testing days 7 and 14.
Routes of Administration

| i. | Vehicle Control | SC |
| --- | --- | --- |
| ii | Positive Control (Morphine) at a dose of 10 mg/kg | SC |
| iii. | Test Item mAb | SC |

Statistics/Evaluation
All data are presented as means±SEM. Each treatment group was compared to vehicle group using a one way ANOVA test followed by Tukey test (Prism V 4.0, GraphPad Software). Comparisons between vehicle group and morphine group and within the vehicle group for evaluating the model were performed using T-test. A p value<0.05 is considered to represent a significant difference.
Animal Care and Use
Species/Strain: Rat Ola Wistar.
Gender: Male.
Age/Weight: Young adults; at study initiation (130-180 g).
Animal Health: The health status of the animals used in this study was examined upon their arrival. Only animals in good health were acclimatized to laboratory conditions and used in the study.
Acclimation: At least 5 days.
Housing: During acclimation and throughout the entire study duration, animals were housed within a limited access rodent facility and kept in groups with a maximum of 3 rats per polypropylene cage. The cages were fitted with solid bottoms and filled with sterile wood shavings as bedding material.
Food and Water: Animals are provided ad libitum with a commercial, sterile rodent diet and had free access to drinking water that is supplied to each cage via polyethylene bottles with stainless steel sipper tubes.
Environment: Automatically controlled environmental conditions were set to maintain temperature at 17-23° C. with a relative humidity (RH) of 30-70%, a 12:12 hour light: dark cycle and 15-30 air changes/h in the study room. Temperature and RH were monitored daily.
Randomization: During the acclimation period, animals were randomly assigned to experimental groups. Each dosing group was kept in separate cages to avoid cross-contamination which can occur through consumption of fecal matter.
Termination: At the end of the study, surviving animals were euthanized by pentobarbital sodium.
Study was performed following approval of an application form submitted to the Committee for Ethical Conduct in the Care and Use of Laboratory Animals that stated that the study complied with the rules and regulations set forth.

Weight Bearing Test:
Rat Training—Habituation to Testing Environment:
This training regime was required as it was anticipated that the level of variability within the experiment is relatively high. Therefore, use of this protocol would help to reduce variability and increase the likelihood of a successful study. Each rat was handled for 1 min then placed in the test apparatus (incapacitance meter) for 5 minutes (habituation to test apparatus). This procedure was performed on study day −2.
Weight Bearing Assessment Details:
Weight bearing deficits were measured in all rats on study day −1, this measurement served as a baseline. Weight bearing was then recorded on study days 9, 16, 21 and 28. Incapacitance meter records 3 measurements over a period of 5 seconds and then averages these to obtain 1 value.
Mechanical Hyperalgesia (Randall-Selitto test):
Mechanical thresholds, expressed in grams, was measured in rats with the Randall-Selitto test using an analgesimeter (Ugo Basile). The test was performed by applying a noxious pressure to the hind paw. By pressing a pedal that activated a motor, the force increased at a constant rate on the linear scale. When the animal displayed pain by withdrawal of the paw or vocalization, the pedal was immediately released and the nociceptive threshold read on a scale. The cut-off of 400 g was used to avoid potential tissue injury. Randall-Selitto test was performed on study days −1 (baseline) and 28.
Clinical Signs:
Throughout the 30-day study, careful clinical examinations were performed at least once daily. If any abnormalities were observed they were recorded. Observations include changes in skin, fur, eyes, mucous membranes, occurrence of secretions and excretions (e.g., diarrhea), autonomic activity (e.g., lacrimation, salivation, piloerection, pupil size, unusual respiratory pattern), gait, posture, and response to handling, as well as the presence of unusual behavior, tremors, convulsions, sleep, and coma.
Results
Mean group body weight for all groups (g).

TABLE 11

|  | Baseline | | Day 7 | | Day 14 | | Day 21 | | Day 27 | |
| --- | --- | --- | --- | --- | --- | --- | --- | --- | --- | --- |
| Treatment | Mean | SEM | Mean | SEM | Mean | SEM | Mean | SEM | Mean | SEM |
| 1 Vehicle | 178.9 | 3.04 | 258.5 | 4.43 | 295.3 | 5.92 | 318.2 | 7.21 | 341.4 | 7.57 |
| 2 Morphine 10 mg/kg | 178.5 | 2.97 | 256.2 | 6.12 | 285.1 | 7.45 | 300.6 | 9.04 | 316 | 9.87 |
| 5 mAb1 | 176.8 | 4.57 | 258.7 | 5.98 | 296.4 | 7.01 | 319.2 | 7.8 | 342.9 | 7.66 |
| 6 mAb2 | 178 | 4.35 | 253.4 | 5.8 | 290.7 | 6.66 | 311.6 | 7.07 | 332.6 | 7.71 |

Response to Weight bearing test (difference between legs) (g):
*p<0.05 vs. Vehicle using one-way ANOVA followed by Tukey test.
The weight bearing of each leg was measured separately by weight bearing apparatus (IITC, Series 8, Model 600®). This test quantifies the spontaneous postural changes reflecting spontaneous pain by independently measuring, on two separate sensors, the weight that the animal applies on each hind paw.
Results were calculated and represented as the percentage of weight that the animal leaned on the injected right leg or intact left leg from the total amount of leaned weight on the two hind legs. Then the difference between the two values of intact left leg minus injected right leg is calculated.

Weight bearing test measures the animal ability to carry its weight on the hind legs. In normal condition the animal carries its weight equally on both hind legs (50% on the right leg and 50% on the left leg). Therefore, the difference between the percentages of weight carried on each leg will be close to 0%. As the animal experiences pain, this situation changes. The animal will tend to carry more weight on the nonpainful leg and less weight on the painful leg. As a result, the difference between the percentages of weight carried on both legs increases.

What is claimed is:

1. A method of treating a canine for pain comprising administering a therapeutically effective amount of a veterinary composition comprising a monoclonal antibody that specifically binds to canine Nerve Growth Factor comprising a variable heavy chain comprising SEQ ID NO. 27 and a variable light chain comprising SEQ ID NO. 26 further comprising a pharmaceutically acceptable carrier.

2. The method of claim 1 wherein the type of pain is selected from the group consisting of: chronic pain, inflammatory pain, post-operative incision pain, neuropathic pain, fracture pain, osteoporotic fracture pain, post-herpetic neuralgia, cancer pain, pain resulting from burns, pain associated with wounds, pain associated with trauma, neuropathic pain, pain associated with musculoskeletal disorders, rheumatoid arthritis, osteoarthritis, ankylosing spondylitis, seronegative (non-rheumatoid) arthropathies, non-articular rheumatism and periarticular disorders and peripheral neuropathy.

3. The method of claim 1 wherein the pain is osteoarthritis pain.

* * * * *